United States Patent
Ridky et al.

(10) Patent No.: US 11,369,618 B2
(45) Date of Patent: Jun. 28, 2022

(54) COMPOUNDS, COMPOSITIONS AND METHODS FOR PREVENTION AND/OR TREATMENT OF CANCER

(71) Applicant: THE TRUSTEES OF THE UNIVERSITY OF PENNSYLVANIA, Philadelphia, PA (US)

(72) Inventors: Todd Ridky, Bryn Mawr, PA (US); Christopher Natale, Philadelphia, PA (US); Jeffrey Winkler, Wynnewood, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 171 days.

(21) Appl. No.: 16/310,198

(22) PCT Filed: May 31, 2017

(86) PCT No.: PCT/US2017/035278
§ 371 (c)(1),
(2) Date: Dec. 14, 2018

(87) PCT Pub. No.: WO2017/218191
PCT Pub. Date: Dec. 21, 2017

(65) Prior Publication Data
US 2020/0306261 A1    Oct. 1, 2020

Related U.S. Application Data

(60) Provisional application No. 62/351,599, filed on Jun. 17, 2016, provisional application No. 62/367,174, filed on Jul. 27, 2016.

(51) Int. Cl.
*A61K 31/565* (2006.01)
*A61K 45/06* (2006.01)
(Continued)

(52) U.S. Cl.
CPC .......... *A61K 31/565* (2013.01); *A61K 31/165* (2013.01); *A61K 31/167* (2013.01);
(Continued)

(58) Field of Classification Search
CPC ...... A61K 31/565; A61K 45/06; A61K 31/19; A61P 35/00
See application file for complete search history.

(56) References Cited

U.S. PATENT DOCUMENTS

| | | |
|---|---|---|
| 5,571,534 A | 11/1996 | Jalonen et al. |
| 7,875,721 B2 | 1/2011 | Prossnitz et al. |

(Continued)

FOREIGN PATENT DOCUMENTS

| | | |
|---|---|---|
| WO | 2007019180 A2 | 2/2007 |
| WO | 2012122101 A1 | 9/2012 |
| WO | 2016137985 A1 | 9/2016 |

OTHER PUBLICATIONS

Liu et al., Med Oncol. 2015;32:104 (Year: 2015).*

(Continued)

*Primary Examiner* — San Ming R Hui
(74) *Attorney, Agent, or Firm* — Saul Ewing Arnstein & Lehr LLP; Domingos J. Silva

(57) ABSTRACT

The present invention includes compounds, compositions and methods that are useful for preventing or treating melanoma or any other cancer in a subject, such as a GPCR-expressing cancer. In certain embodiments, the compounds comprise estrogen (including estrogen derivatives or analogues), a selective GPER agonist and/or another G-protein coupled receptor (GPCR) agonist that increases cancer cell differentiation.

18 Claims, 34 Drawing Sheets

(51) Int. Cl.
- A61K 31/19 (2006.01)
- A61P 35/00 (2006.01)
- A61K 38/15 (2006.01)
- A61K 31/165 (2006.01)
- A61K 31/4045 (2006.01)
- A61K 31/167 (2006.01)

(52) U.S. Cl.
CPC .......... *A61K 31/19* (2013.01); *A61K 31/4045* (2013.01); *A61K 38/15* (2013.01); *A61K 45/06* (2013.01); *A61P 35/00* (2018.01)

(56) References Cited

U.S. PATENT DOCUMENTS

| | | | |
|---|---|---|---|
| 8,487,100 | B2 | 7/2013 | Prossnitz et al. |
| 8,735,553 | B1* | 5/2014 | Li ............... A61K 39/39591 530/388.22 |
| 2008/0167334 | A1 | 7/2008 | Prossnitz et al. |
| 2010/0113602 | A1* | 5/2010 | Palmieri ............ A61K 41/00 514/619 |
| 2011/0092533 | A1 | 4/2011 | Prossnitz et al. |
| 2015/0218274 | A1 | 8/2015 | Sabatos-Peyton et al. |

OTHER PUBLICATIONS

Piantelli et al., J invest Dermatol, 105:248-253, 1995 (Year: 1995).*
Mahoney et al., Clinical Therapeutics, 37(4):764-782, 2015 (Year: 2015).*
Abstract of Muthian et al., J Clin Immunol, 24(5):542-552, 2004 (Year: 2004).*
Wangari-Talbot et al., Pharmaceuticals, 3:2821-2837, 2010 (Year: 2010).*
Garbe et al., The Oncologist 2011;16:5-24 (Year: 2011).*
Extended European Search Report for European Patent Application No. 17813776.6 dated Jan. 31, 2020.
Amodio, et al., "Selective G-Protein Estrogen Receptor (GPER) Activation Triggers Anti-Multiple Myeloma Activity and Synergizes with MiR-29b-Inducing Drugs", Blood 124(21), 2014, 4725 (abstract only).
Desimone, et al., "Evaluation of GPER agonist G-1 combined with navitoclax in platinum-resistant and -senistive ovarian cancer cells", American Society of Clinical Oncology Annual Meeting, Chicago, IL, May 31-Jun. 4, 2013, Abstract Only.
Liu, et al., "The BRAF and MEK Inhibitors Dabrafenib and Trametinib: Effects on Immune Function and in Combination with Immunomodulatory Antibodies Targeting PD-1, PD-L1, and CTLA-4", Clin Cancer Res. 21(7), Apr. 2015, 1639-1651.
International Search Report and Written Opinion for PCT International Application No. PCT/US2017/035278 dated Aug. 30, 2017.
Dang, et al.,MYC on the path to cancer, Cell. 149(1) ,2012 ,22-35.
Höglund, et al., Therapeutic implications for the induced levels of Chk1 in Myc-expressing cancer cells, Clin Cancer Res. 17(22) ,Nov. 2011 ,7067-7079.
Hughes, et al.,Targeted Therapy and Checkpoint Immunotherapy Combinations for the Treatment of Cancer, Trends Immunol. 37(7), Jul. 2016, 462-476.
Ignatov, et al.,GPER-1 acts as a tumor suppressor in ovarian cancer, J Ovarian Res. 6(1) ,2013 ,51.
Lam, et al.,Targeting GPR30 with G-1: a new therapeutic target for castration-resistant prostate cancer, Endocr Relat Cancer. 21(6), 2014, 903-914.
Liu, et al.,G protein-coupled receptors as promising cancer targets, Cancer Lett. 376(2) ,Jul. 2016 ,226-239.
Meyer, et al.,Reflecting on 25 years with MYC, Nat Rev Cancer. 8(12) ,2008 ,976-990.
Munster et al.,A phase II study of the histone deacetylase inhibitor vorinostat combined with tamoxifen for the treatment of patients with hormone therapy-resistant breast cancer, Br J Cancer. 104(12), Jun. 2011, 1828-1835.
Weissenborne, et al.,GPER functions as a tumor suppressor in MCF-7 and SK-BR-3 breast cancer cells, J Cancer Res Clin Oncol.140 ,2014 ,663-671.
Bologa, et al., "Virtual and biomolecular screening converge on a selective agonist for GPR30", Nature Chemical Biology, vol. 2, No. 4, Apr. 2006, pp. 207-212.
Prossnitz, et al., "International Union of Basic and Clinical Pharmacology. XCVII. G Protein-Coupled Estrogen Receptor and Its Pharmacologic Modulators", Pharmacological Review, vol. 67, Jul. 2015, pp. 505-540.

* cited by examiner

COMPOUNDS, COMPOSITIONS AND METHODS FOR PREVENTION AND/OR TREATMENT OF CANCER

CROSS-REFERENCE TO RELATED APPLICATIONS

The present application is a 35 U.S.C. § 371 national phase application from, and claims priority to, International Application No. PCT/US2017/035278, filed May 31, 2017, and published under PCT Article 21(2) in English, which claims priority under 35 U.S.C. § 119(e) to U.S. Provisional Patent Applications No. 62/351,599, filed Jun. 17, 2016, and No. 62/367,174, filed Jul. 27, 2016, all of which applications are incorporated herein by reference in their entireties.

STATEMENT REGARDING FEDERALLY SPONSORED RESEARCH OR DEVELOPMENT

This invention was made with government support under F31CA206325 awarded by the National Cancer Institute. The government has certain rights in the invention.

BACKGROUND OF THE INVENTION

Melanoma is the most lethal form of skin cancer and develops from pigment-containing cells known as melanocytes. Melanomas typically occur in the skin, but may also occur in the mouth, intestines or eye. The primary cause of melanoma is DNA damage caused by ultraviolet light exposure, especially in those individuals with light skin with low level of skin pigment (melanin) A large fraction of melanomas develop from preexisting nevi (moles). People with low levels of baseline skin pigment, numerous moles, a history of affected family members, and poor immune function are at a greater risk of developing melanoma. There are over 80,000 cases of melanoma per year in the United States. Treatment options are limited at the moment, with only 30% of patients with melanoma metastasis surviving beyond 5 years.

There is a need in the art for compounds, compositions and methods that can be used to prevent and/or treat melanoma and other cancers in a subject. Such compounds, compositions and methods should exhibit equivalent and/or superior clinical efficacy to current anticancer therapeutics, or alternatively, increase the efficacy of other anticancer therapeutics when used in combination therapy. The present invention satisfies this need.

BRIEF SUMMARY OF THE INVENTION

The invention provides a method of treating or preventing a GPCR-expressing cancer in a subject. The invention further provides a method of treating or preventing a Myc-expressing cancer in a subject. The invention further provides a composition comprising (i) estrogen and/or GPCR agonist and (ii) chemotherapy, an engineered CAR T-cell, and/or an immune checkpoint inhibitor. The invention further provides a kit comprising (i) estrogen and/or GPCR agonist and (ii) chemotherapy, an engineered CART'-cell, an immune checkpoint inhibitor, and/or radiation therapy, and instructional material for use thereof in treating or preventing a cancer in a subject.

In certain embodiments, the method comprises administering to the subject in need thereof a therapeutically effective amount of estrogen and/or a G-protein coupled receptor (GPCR) agonist that increases cellular differentiation in the cancer. In other embodiments, the subject is further co-administered at least one immunotherapeutic agent. In yet other embodiments, the subject is further co-administered at least one histone deacetylase inhibitor (HDAC).

In certain embodiments, the GPCR agonist comprises a selective G protein-coupled estrogen receptor (GPER) agonist.

In certain embodiments, the Myc-expressing cancer is at least one selected from the group consisting of melanoma, Burkitt lymphoma, leukemia, sarcoma, lymphoma, multiple myeloma, brain cancer, neuroblastoma, medulloblastoma, astrocytoma, glioblastoma, ovarian cancer, cervix cancer, uterine cancer, colorectal cancer, breast cancer, pancreatic cancer, lung cancer, stomach cancer, thyroid cancer, liver cancer, prostate cancer, esophagus cancer, kidney cancer, bladder cancer, and gall bladder cancer. In other embodiments, the Myc-expressing cancer is at least one selected from the group consisting of melanoma, pancreatic cancer, and lung cancer.

In certain embodiments, the GPCR-expressing cancer is at least one selected from the group consisting of melanoma, Burkitt lymphoma, leukemia, sarcoma, lymphoma, multiple myeloma, brain cancer, neuroblastoma, medulloblastoma, astrocytoma, glioblastoma, ovarian cancer, cervix cancer, uterine cancer, colorectal cancer, breast cancer, pancreatic cancer, lung cancer, stomach cancer, thyroid cancer, liver cancer, prostate cancer, esophagus cancer, kidney cancer, bladder cancer, and gall bladder cancer. In other embodiments, the GPCR-expressing cancer is at least one selected from the group consisting of melanoma, pancreatic cancer, and lung cancer.

In certain embodiments, the cancer is selected from the group consisting of melanoma, pancreatic cancer, and lung cancer.

In certain embodiments, the immunotherapeutic agent comprises an immune checkpoint inhibitor. In other embodiments, the immune checkpoint inhibitor is selected from the group consisting of a PD-1 inhibitor, PD-L1 inhibitor, CTLA-4 inhibitor, TIGIT inhibitor, LAG3 inhibitor, IDO(1/2) inhibitor, and B7-H3 inhibitor.

In certain embodiments, the at least one HDAC inhibitor is selected from the group consisting of valproic acid, vorinostat, romidepsin, trichostatin A, and panobinostat.

In certain embodiments, the estrogen and/or GPCR agonist, and the at least one immune checkpoint inhibitor, are co-administered to the subject. In other embodiments, the estrogen and/or GPCR agonist, and the at least one immune checkpoint inhibitor, are co-formulated.

In certain embodiments, the estrogen and/or GPCR agonist, and the at least one HDAC, are co-administered to the subject. In other embodiments, the estrogen and/or GPCR agonist, and the at least one HDAC, are co-formulated.

In certain embodiments, the estrogen and/or GPCR agonist is/are the only anticancer agent administered to the subject. In other embodiments, the estrogen and/or GPCR agonist are/is the only anticancer agent administered to the subject in an amount sufficient to treat or prevent the cancer in the subject.

In certain embodiments, the GPCR is selected from the group consisting of G-protein coupled estrogen receptor (GPER), MC1R, CYSLTR2, F2R, HRH2, LPAR2/3/6, PTGER1, $S1PR_2$, $S1PR_3$, and $TBXA_2R$. In other embodiments, the GPCR is selected from the group consisting of GPER, F2R, PTGER1, and $TBXA_2R$.

In certain embodiments, the estrogen comprises at least one selected from the group consisting of estrone (E1), estradiol (E2), estriol (E3), estetrol (E4), 17β-estradiol, 27-hydroxycholesterol, dehydroepiandrosterone (DHEA), 7-oxo-DHEA, 7α-hydroxy-DHEA, 16α-hydroxy-DHEA, 7β-hydroxyepiandrosterone, $\Delta^4$-androstenedione, $\Delta^5$-androstenediol, 3α-androstanediol, 3β-androstanediol, 2-hydroxyestrone, 16-hydroxyestrone, estradiol cypionate, estradiol valerate, estradiol acetate, estradiol benzoate, ethinyl estradiol (EE), mestranol, moxestrol, quinestrol, diethylstilbestrol benzestrol, dienestrol, dienestrol acetate, diethylstilbestrol dipropionate, fosfestrol, hexestrol, methestrol dipropionate, xenoestrogens, phytoestrogens, and mycoestrogens, or a salt, solvate, tautomer, enantiomer or diastereoisomer thereof.

In certain embodiments, the GPER agonist comprises at least one selected from the group consisting of G-1, tamoxifen, fulvestrant, and raloxifene, or a salt, solvate, tautomer, enantiomer or diastereoisomer thereof.

In certain embodiments, the GPER agonist comprises at least one selected from the group consisting of:
a molecule of formula (I):

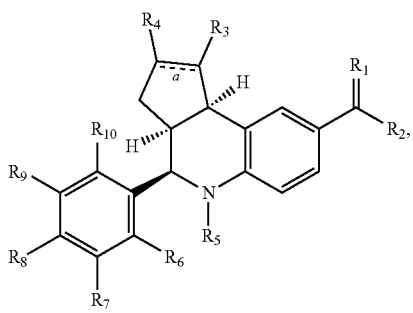

wherein in (I):
$R_1$ is selected from the group consisting of =O, =N—OH, =N—NHC(=O)(p-methoxy phenyl), =N—NHC(=O)CH(OMe)phenyl, and =N—NH(5-iodo-pyrid-2-yl); $R_2$ is selected from the group consisting of $C_1$-$C_4$ alkyl and $C_1$-$C_4$ haloalkyl; bond a is a single or double bond, such that: if bond a is a double bond, $R_3$ and $R_4$ are H, and if bond a is a single bond, $R_3$ is selected from the group consisting of H, —OH, —OAc, and halo; $R_4$ is selected from the group consisting of H, —OH, —OAc, and —S(o-nitrophenyl); or $R_3$ and $R_4$ combine to form a diradical selected from the group consisting of —CH$_2$—, —OCH$_2$O—, —OCH(CH$_3$)O—, and —OC(CH$_3$)$_2$O—; $R_5$ is selected from the group consisting of H, benzyl, $C_1$-$C_4$ alkyl, and acetyl; $R_6$ is selected from the group consisting of H, halo, —NO$_2$, $C_1$-$C_4$ alkyl, —C≡CH, —C≡C—Si(CH$_3$)$_3$ (or —C≡C-TMS), —O-benzyl, —OH, —OAc, $C_1$-$C_4$ alkoxy, —COOH, and —COO($C_1$-$C_4$ alkyl); $R_7$ is selected from the group consisting of H, halo, —NO$_2$, $C_1$-$C_4$ alkyl, —OH, —OAc, and $C_1$-$C_4$ alkoxy; $R_8$ is selected from the group consisting of H, halo, —NO$_2$, $C_1$-$C_4$ alkyl, —O-benzyl, —N(R)(R), —SR, —COOH, —COO($C_1$-$C_4$ alkyl), —OH, —OAc, $C_1$-$C_4$ alkoxy, 3-thietyl-methoxy, —SO$_2$(morpholino), and OCH$_2$CH=CH$_2$, wherein each occurrence of R is independently selected from the group consisting of H and $C_1$-$C_4$ alkyl; $R_9$ is selected from the group consisting of H, halo, —NO$_2$, $C_1$-$C_4$ alkyl, —OH, —OAc, and $C_1$-$C_4$ alkoxy, or $R_8$ and $R_9$ combine to form a diradical selected from the group consisting of —OCH$_2$O—, —OCH(CH$_3$)O—, —OC(CH$_3$)$_2$O—, —O(CH$_2$)$_2$O—, CH=CH and —CH=CH—O—; $R_{10}$ is selected from the group consisting of H, $C_1$-$C_4$ alkyl, and halo; wherein each occurrence of benzyl is independently optionally substituted with at least one group selected from the group consisting of $C_1$-$C_4$ alkyl, —OH, $C_1$-$C_4$ alkoxy, halo, and —NO$_2$; and
a molecule of formula (II):

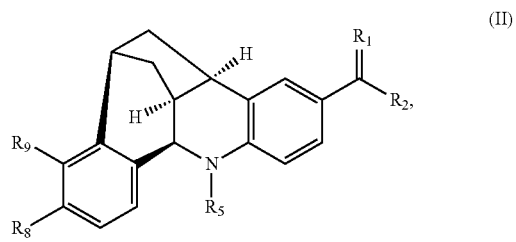

wherein in (II):
$R_1$ is selected from the group consisting of =O and =N—OH; $R_2$ is $C_1$-$C_4$ alkyl; $R_5$ is selected from the group consisting of H, benzyl and $C_1$-$C_4$ alkyl; $R_8$ and $R_9$ are independently selected from the group consisting of H and $C_1$-$C_4$ alkoxy, or $R_8$ and $R_9$ combine to form a diradical selected from the group consisting of —OCH$_2$O—, —OCH(CH$_3$)O— and —OC(CH$_3$)$_2$O—, or a salt, solvate, tautomer, enantiomer or diastereoisomer thereof, or any mixtures thereof.

In certain embodiments, the GPER agonist comprises at least one selected from the group consisting of:
a molecule of Formula (I-1):

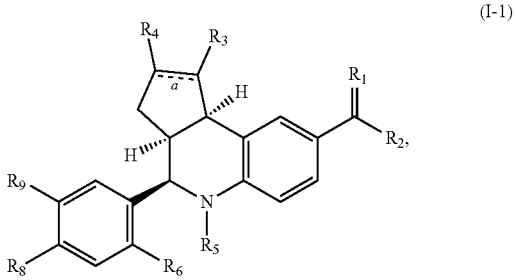

wherein in (I-1):
$R_1$ is selected from the group consisting of =O and =N—OH; $R_2$ is $C_1$-$C_4$ alkyl; bond a is a single or double bond, such that: if bond a is a double bond, $R_3$ and $R_4$ are H, and if bond a is a single bond, $R_3$ and $R_4$ are independently selected from the group consisting of H and —OH, or $R_3$ and $R_4$ combine to form a diradical selected from the group consisting of —OCH$_2$O—, —OCH(CH$_3$)O— and —OC(CH$_3$)$_2$O—; $R_5$ is selected from the group consisting of H, benzyl and $C_1$-$C_4$ alkyl; $R_6$ is selected from the group consisting of H and halo; $R_8$ and $R_9$ are independently selected from the group consisting of H and $C_1$-$C_4$ alkoxy, or $R_8$ and $R_9$ combine to form a diradical selected from the group consisting of —OCH$_2$O—, —OCH(CH$_3$)O— and —OC(CH$_3$)$_2$O—; and a molecule of formula (II):

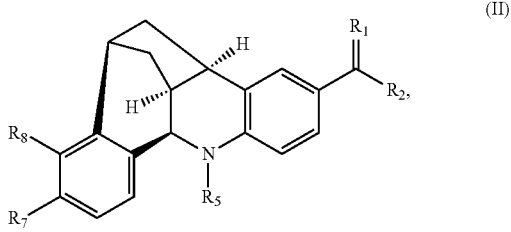

wherein in (II):
R₁ is selected from the group consisting of =O and =N—OH; R₂ is C₁-C₄ alkyl; R₅ is selected from the group consisting of H, benzyl and C₁-C₄ alkyl; R₇ and R₈ are independently selected from the group consisting of H and C₁-C₄ alkoxy, or R₇ and R₈ combine to form a diradical selected from the group consisting of —OCH₂O—, —OCH(CH₃)O— and —OC(CH₃)₂O—, or a salt, solvate, tautomer, enantiomer or diastereoisomer thereof, or any mixtures thereof.

In certain embodiments, the GPER agonist comprises at least one selected from the group consisting of: G-1; CMPD1 (rel-1-((3aS,4R,9bR)-4-(benzo[d][1,3]dioxol-5-yl)-3a,4,5,9b-tetrahydro-3H-cyclopenta[c]quinolin-8-yl)ethan-1-one); CMPD2 (rel-1-((3aS,4R,9bR)-4-(6-bromobenzo[d][1,3]dioxol-5-yl)-5-methyl-3a,4,5,9b-tetrahydro-3H-cyclopenta[c]quinolin-8-yl)ethan-1-one); CMPD3 (rel-1-((3aS,4R,9bR)-4-(6-bromobenzo[d][1,3]dioxol-5-yl)-2,3,3a,4,5,9b-hexahydro-1H-cyclopenta[c]quinolin-8-yl)ethan-1-one); CMPD4 (rel-1-((3aS,4R,9bR)-5-benzyl-4-(6-bromobenzo[d][1,3]dioxol-5-yl)-3a,4,5,9b-tetrahydro-3H-cyclopenta[c]quinolin-8-yl)ethan-1-one); CMPD5 (rel-1-((3aS,4R,9bR)-4-(2-bromophenyl)-3a,4,5,9b-tetrahydro-3H-cyclopenta[c]quinolin-8-yl)ethan-1-one); CMPD6 (rel-1-43aS,4R,9bR)-4-(6-bromobenzo[d][1,3]dioxol-5-yl)-3a,4,5,9b-tetrahydro-3H-cyclopenta[c] quinolin-8-yl)ethan-1-one oxime); CMPD7 (rel-1-((3aS,4R,9bR)-4-(2-bromo-4,5-dimethoxyphenyl)-3a,4,5,9b-tetrahydro-3H-cyclopenta[c]quinolin-8-yl)ethan-1-one); CMPD8 (rel-1-((3aS,4R,9bR)-4-(6-chlorobenzo[d][1,3]dioxol-5-yl)-3a,4,5,9b-tetrahydro-3H-cyclopenta[c]quinolin-8-yl)ethan-1-one); CMPD9 (rel-1-46R,6aS,7aS,10aR,10bR)-6-(6-bromobenzo[d][1,3]dioxol-5-yl)-9,9-dimethyl-6,6a,7,7a,10a,10b-hexahydro-5H-[1,3]dioxolo[4',5':3,4]cyclopenta[1,2-c]quinolin-2-yl)ethan-1-one); CMPD10 (rel-1-41R,2S,3aS,4R,9bR)-4-(6-bromobenzo[d][1,3]dioxol-5-yl)-1,2-dihydroxy-2,3,3a,4,5,9b-hexahydro-1H-cyclopenta[c]quinolin-8-yl)ethan-1-one); CMPD11 (rel-1-43aS,4R,9bR)-4-(2-bromo-4,5-dimethoxyphenyl)-2,3,3a,4,5,9b-hexahydro-1H-cyclopenta[c]quinolin-8-yl)ethan-1-one); and CMPD12 (rel-1-((4S,5aS,6R,11aR)-4,5,5a,6,11,11a-hexahydro-4,6-methano[1,3]dioxolo[4',5':5,6]benzo[1,2-c]acridin-8-yl)ethan-1-one), or a salt, solvate, tautomer, enantiomer or diastereoisomer thereof, or any mixtures thereof.

In certain embodiments, the GPCR agonist is selected from the group consisting of afamelanotide (N-acetyl-L-seryl-L-tyrosyl-L-seryl-L-norleucyl-L-α-glutamyl-L-histidyl-D-phenylalanyl-L-arginyl-L-tryptophylglycyl-L-lysyl-L-prolyl-L-valinamide), N-methyl LTC4 (N-methyl-5S-hydroxy-6R-(S-glutathionyl)-7E,9E,11Z,14Z-eicosatetraenoic acid), TFLLR-NH₂ (Thr-Phe-Leu-Leu-Arg-NH₂), Impromidine (2-[3-(1H-imidazol-5-yl)propyl]-1-[2-[(5-methyl-1H-imidazol-4-yl)methylsulfanyl]ethyl]guanidine), Carbachol (2-[(Aminocarbonyl) oxy]-N,N,N-trimethylethanaminium chloride), Sulprostone ((Z)-7-[(1R,3R)-3-hydroxy-2-[(E,3R)-3-hydroxy-4-phenoxybut-1-enyl]-5-oxocyclopentyl]-N-methylsulfonylhept-5-enamide), FTY720 (2-Amino-2-[2-(4-octyl-phenyl)-ethyl]-propane-1,3-diol hydrochloride) and U46619 ((E)-7-41R,4R,5S,6R)-6-((S,Z)-3-hydroxyoct-1-en-1-yl)-2-oxabicyclo[2.2.1]heptan-5-yl)hept-5-enoic acid).

In certain embodiments, the estrogen or GPCR agonist is administered to the subject as a pharmaceutical composition further comprising at least one pharmaceutically acceptable carrier. In other embodiments, the subject is further administered at least one additional anticancer treatment. In yet other embodiments, the at least one additional anticancer treatment comprises chemotherapy, an engineered chimeric antigen receptor (CAR) T-cell, an immune checkpoint inhibitor, and/or radiation therapy. In yet other embodiments, the chemotherapy is selected from the group consisting of a histone deacetylase inhibitor (HDAC), temozolomide, dacarbazine (DTIC), vemurafenib, dabrafenib and trametinib. In yet other embodiments, the immune checkpoint inhibitor is selected from the group consisting of a PD-1 inhibitor, PD-L1 inhibitor, CTLA-4 inhibitor, LAG3 inhibitor, IDO(1/2) inhibitor, TIGIT inhibitor, and B7-H3 inhibitor. In yet other embodiments, the estrogen or GPCR agonist is administered to the subject by at least one administration route selected from the group consisting of inhalational, oral, rectal, vaginal, parenteral, topical, transdermal, pulmonary, intranasal, buccal, ophthalmic, intrathecal, intracranial, and intravenous. In certain embodiments, the subject is a mammal. In other embodiments, the mammal is human.

In certain embodiments, the subject has the cancer or has been diagnosed as suffering from the cancer. In other embodiments, the subject does not have the cancer or has not been diagnosed as suffering from the cancer. In yet other embodiments, the estrogen and/or GPCR agonist is/are administered to the subject over a period of 3 weeks or less. In other embodiments, the estrogen or GPCR agonist is administered to the subject over a period of 2 weeks or less. In yet other embodiments, the estrogen or GPCR agonist is administered to the subject over a period of 1 week or less.

BRIEF DESCRIPTION OF THE DRAWINGS

The following detailed description of specific embodiments of the invention will be better understood when read in conjunction with the appended drawings. For the purpose of illustrating the invention, depicted in the drawings are certain embodiments. It should be understood, however, that the invention is not limited to the precise arrangements and instrumentalities of the embodiments shown in the drawings.

FIG. 4A: 5 day proliferation assay of B16F10, WM46 (BRAF$^{V600E}$), WM51 (BRAF$^{V600E}$), and WM3702 (NRAS$^{Q61L}$) cells treated with estrogen (E2), * denotes significance by a two-tailed T-test, n=3 per group. FIG. 4B: 5 day melanin assay of B16F10, WM46 (BRAF$^{V600E}$), WM51 (BRAF$^{V600E}$), and WM3702 (NRAS$^{Q61L}$) cells treated with E2, * denotes significance by a two-tailed T-test, n=3 per group. FIG. 4C: 5 day proliferation assay of B16F10, WM46 (BRAF$^{V600E}$), WM51 (BRAF$^{V600E}$) and WM3702 (NRAS$^{Q61L}$) cells treated with GPER agonist (G-1), * denotes significance by a two-tailed T-test, n=3 per group. FIG. 4D: 5 day melanin assay of B16F10, WM46 (BRAF$^{V600E}$), WM51 (BRAF$^{V600E}$), and WM3702 (NRAS$^{Q61L}$) cells treated with G-1, * denotes significance by a two-tailed T-test, n=3 per group. FIG. 4E: 3 day proliferation assay of B16F10 cells treated with a dose response of G-1, * denotes significance One-way ANOVA with Tukey's multiple comparison test, n=5 per group. FIG. 4F: Western blot of B16F10 cells treated for 16 hours with a saturating dose response of G-1. All error bars equal the standard deviation of the samples.

FIG. 7A: Western blot validating the transduction of normal human melanocytes with doxycycline inducible BRAF(V600E), dominant-negative p53(R248W), active CDK4(R24C) and hTERT. FIG. 7B: Representative photo of a SCID mouse with a human engineered melanoma xenograft. FIG. 7C: MITF immunohistochemistry across all non-breeding and breeding mice, * denotes replicates shown in FIG. 1. Scale bars=100 µM.

FIG. 8A: Experimental timeline of genetically-defined human xenograft melanoma on SCID mice, n=5 per group. FIG. 8B: Histologic characterization of representative orthotopic skin and resulting tumors, including hematoxylin and eosin (H/E), melanocyte and proliferation markers MITF, Ki67/MART, and Fontana Masson (Melanin). Scale bars=100 µM. FIGS. 8C-8E: Quantification of epidermal MITF staining (FIG. 8C), Ki67 proliferation index (FIG. 8D) and melanin staining in epidermal keratinocytes (FIG. 8E), * denotes significance by the Mann-Whitney test.

FIG. 10A demonstrates decreased differentiation, while each of FIGS. 10B-10D demonstrates increased differentiation.

FIG. 11A: Long-term melanin assay in which normal human melanocytes were transiently treated with progesterone (P4), or estrogen (E2). Subsets of these groups (Red) were treated with an additional transient pulse of P4 at Day 27. Error bars equal the standard deviation of the samples. FIG. 11B: Western blot of melanocyte differentiation markers after a transient, 4-day treatment with either vehicle or estrogen, followed by an 8 day withdraw period. FIG. 11C: Experimental timeline of estrogen or GPER agonist (G-1) pre-treatment of mouse and human melanoma cells, n=5 per group. FIG. 11D: Relative tumor weights of mouse and human melanomas pre-treated with estrogen, * denotes significance by the Mann-Whitney test. FIG. 11E: Relative tumor weights of mouse and human melanomas pre-treated with G-1, * denotes significance by the Mann-Whitney test.

FIGS. 13A-13C: Western blots of B16F10 (FIG. 13A), WM46 (FIG. 13B), and YUMM 1.7 (FIG. 13C) melanoma cells after transient treatment with a pregnancy-associated concentration of E2 (25 nM) or an optimized concentration of G-1 (500 nM). FIG. 13D: Experimental timeline of vehicle or G-1 pre-treatment of B16F10 cells followed by treatment with either αPD-1 antibody or isotype antibody control (2A3), n=5 per group. FIG. 13E: Tumor volumes of treatment groups at Day 14, * denotes significance One-way ANOVA with Tukey's multiple comparison test. FIG. 13F: Survival curve of mice with tumors pre-treated with vehicle or G-1, followed by isotype antibody control (2A3) or αPD-1 antibody. Significance between groups by the Log-Rank (Mantel-Cox) test is listed in the table below. FIG. 13G: Western blot of luciferase- or c-Myc-transduced WM46 cells treated with G-1 for 16 hours.

FIG. 14A: Experimental timeline of B16F10 bearing mice treated with vehicle or G-1, as well as αPD-1 antibody or isotype antibody control (2A3), n=10 per group. FIG. 14B: Tumor volumes of treatment groups at Day 14, * denotes significance One-way ANOVA with Tukey's multiple comparison test. FIG. 14C: Survival curve of mice treated with vehicle or G-1, as well as isotype antibody control (2A3) or αPD-1 antibody. Significance between groups by the Log-Rank (Mantel-Cox) test is listed in the table below. FIG. 14D: Experimental outline of YUMM1.7 bearing mice treated with vehicle or G-1, as well as isotype antibody control (2A3) or αPD-1 antibody. Treatment was started at day 14 after tumors reached 4-5 mm in diameter. n=5 per group. FIG. 14E: Tumor volumes over time of treatment groups. FIG. 14F: Survival curve of mice treated with vehicle or G-1, as well as αPD-1 antibody or isotype antibody control (2A3). Significance between groups by the Log-Rank (Mantel-Cox) test is listed in the table in FIG. 14F.

FIG. 15A: Experimental timeline for vehicle or G-1 treatment of YUMM 1.7 melanoma bearing mice. FIG. 15B: Heatmap summarizing immune profiling across biological replicates, n=5 per group, * denotes significance by two-way ANOVA assuming each immune population is an independent measurement of immune activation. FIG. 15C: Quantification of individual immune populations from FIG. 15B, n=5 per group.

FIG. 16A: Mass spectrometry of normal human melanocytes treated transiently with estrogen, red data points (*) denote significantly up regulated, CBP/p300 regulated histone acetylations. FIG. 16B: Western blot of p-RB, c-Myc, and H3K56ac in melanoma cells after treatment with G-1, HDACi, or in combination. FIG. 16C: Proliferation assay of B16F10 melanoma cells after treatment with G-1, HDACi, or in combination.

FIG. 17A: Western blot of c-Myc in several PDAC cell lines treated with 500 nM G-1 for 1 hour. FIG. 17B: Proliferation assay of several PDAC cell lines treated with 500 nM G-1 over 5 days. FIG. 17C: Experimental timeline for vehicle or G-1 treatment of PDAC tumor bearing mice. FIG. 17D: Tumor weights of PDAC tumor bearing mice treated with either vehicle or G-1.

FIG. 18A: Western blot for pCREB of LLC1 cells treated with 500 nM G-1 for 30 minutes. FIG. 18B: Proliferation assay of LLC1 treated with 500 nM G-1 for 6 days. FIG. 18C: Western blot for c-Myc of LLC1 cells treated with 500 nM G-1 for 6 days. FIG. 18D: Western blot for c-Myc of LLC1 cells treated with 500 nM G-1 over a time-course. FIG. 18E: Western blot for pCREB and c-Myc of TC-1 cells treated with 500 nM G-1 for 1 hour. FIG. 18F: Tumor volumes over time of LLC1 tumor bearing mice treated with vehicle or G-1, as well as αPD-1 antibody or isotype antibody control (2A3). FIG. 18G: Survival curve of mice treated with vehicle or G-1, as well as αPD-1 antibody or isotype antibody control (2A3). Significance between groups by the Log-Rank (Mantel-Cox) test is listed in the table below.

DETAILED DESCRIPTION OF THE INVENTION

The present invention relates to the unexpected discovery that estrogen and/or small molecule G-protein coupled receptor (GPCR) agonists increase melanocyte differentiation, and can be used to prevent and/or treat a GPCR-expressing (such as a GPER-expressing) and/or Myc-expressing cancer, such as but not limited to melanoma, pancreatic cancer and/or non-small cell lung cancer, in a subject. In certain embodiments, the GPCR is the G-protein coupled estrogen receptor (GPER), the melanocortin receptor (MC1R), or other GPCRs that activate similar downstream signaling events.

Myc protein is a transcription factor that activates expression of several genes by binding enhancer box sequences and/or recruiting histone acetyltransferases. Myc can also act as a transcriptional repressor, inhibiting expression of certain target genes. Myc has a direct role in the control of DNA replication, cell proliferation, differentiation, cancer invasion, angiogenesis, cell survival, and cancer cell escape from immune surveillance. Myc is expressed in many cancer types and is functionally important. It is thus a biologically attractive therapeutic target. However, targeting Myc with pharmacologic compounds has been extremely difficult, and no currently approved cancer drugs directly target Myc.

Myc is activated by various mitogenic signals, such as serum stimulation, or by Wnt, Shh and EGF (via the MAPK/ERK pathway). Myc is a strong oncogenic protein that is often found upregulated in many types of cancers, such as melanoma, Burkitt lymphoma, leukemia, sarcoma, lymphoma, multiple myeloma, brain cancer, neuroblastoma, medulloblastoma, astrocytoma, glioblastoma, ovarian cancer, cervix cancer, uterine cancer, colorectal cancer, breast cancer, pancreatic cancer, lung cancer, stomach cancer, thyroid cancer, liver cancer, prostate cancer, esophagus cancer, kidney cancer, bladder cancer, and/or gall bladder cancer.

Figure 1:
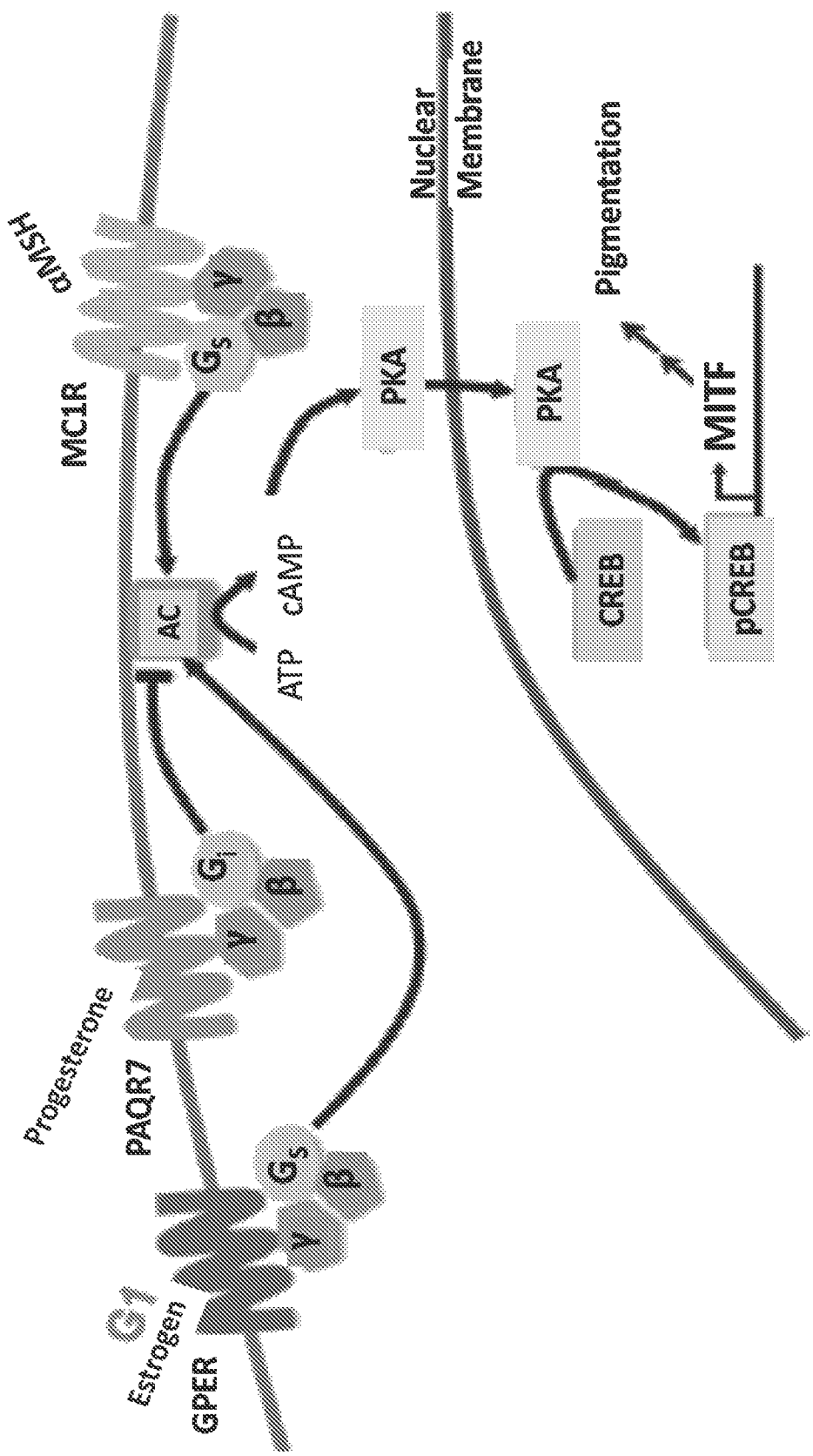
FIG. 1 is a non-limiting schematic model of how sex hormones influence the normal pigment production and/or differentiation program in melanocytes.
Figure 2:
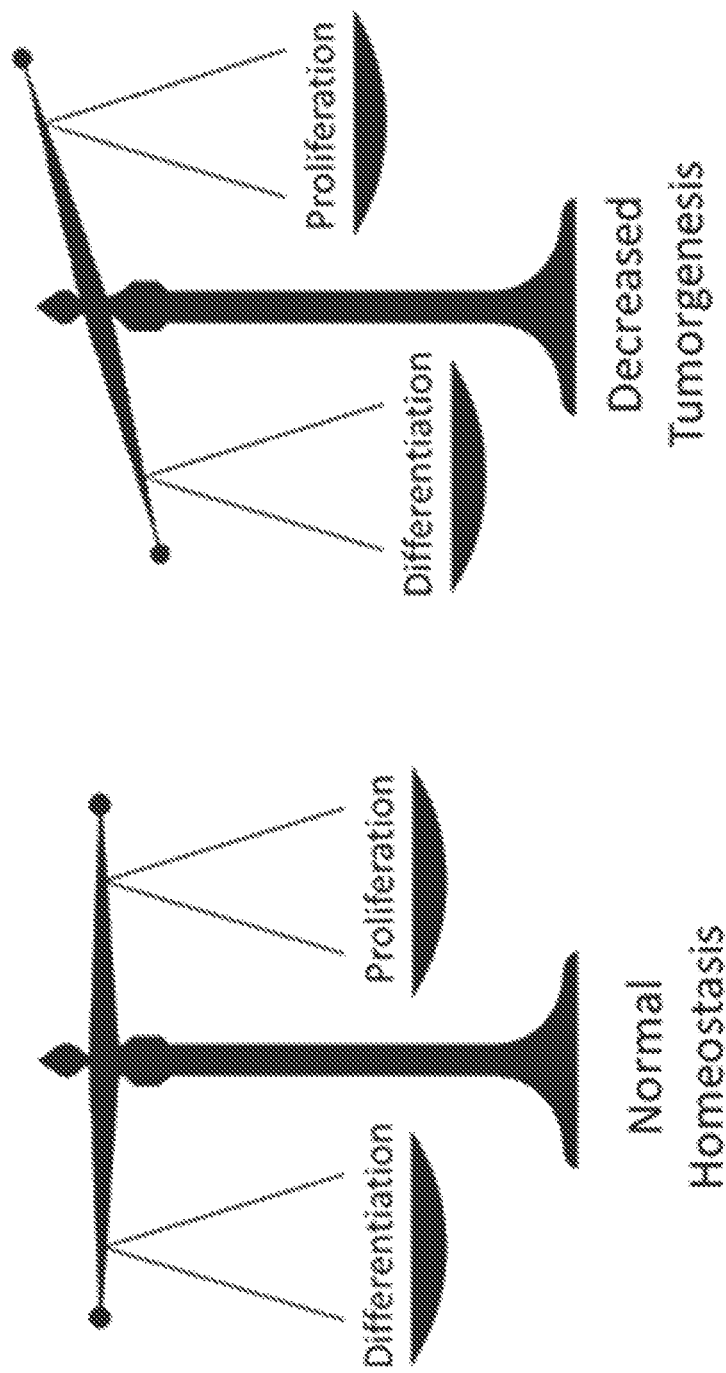
FIG. 2 illustrates non-limiting balance of differentiation and proliferation under normal homeostatic conditions, while more differentiated cells are generally considered to be less tumorigenic.

Melanocytes, which are the cells of origin for melanoma, and many other human cell types express the non-canonical steroid hormone receptor G-protein coupled estrogen receptor 1 (GPER1). As demonstrated herein, activation of GPER in melanocytes by either estrogen or an illustrative non-limiting selective GPER specific agonist (G-1) was found to increase the differentiation state of human melanocytes. In so doing, GPER agonists inhibit the ability of melanocytes to proliferate, increase their production of melanin pigment and melanocyte differentiation antigen proteins (FIG. 1), and decrease their ability to form cancer. This reflects the fact that differentiation and proliferation are generally thought to be in a balance under normal conditions, where more differentiated melanocytes are less tumorigenic (FIG. 2).

Figure 19:
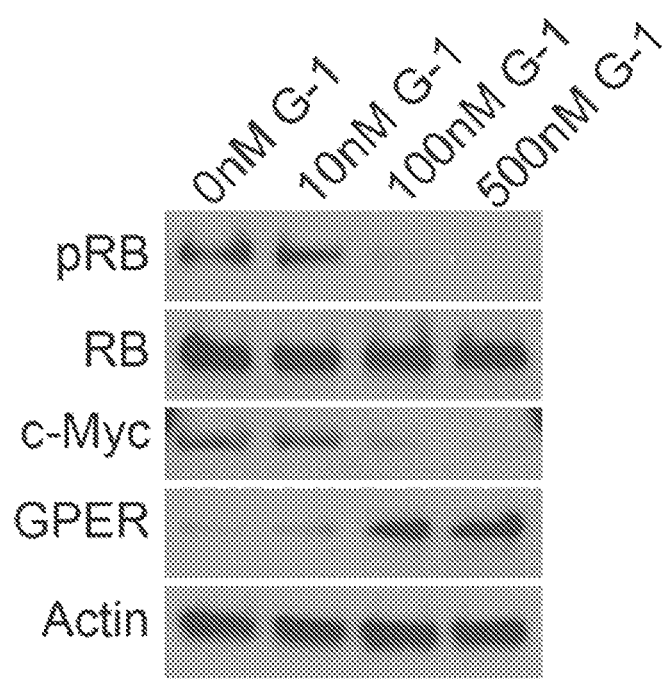
FIG. 19 is a western blot image derived from WM46 melanoma cells treated with increasing doses of G-1. The data show reduction in pRB and c-myc levels, and an elevation of GPER expression, in response to increasing concentrations of the GPER agonist G-1.

In one aspect, the invention relates to the unexpected discovery that estrogen and/or GPCR agonists (such as selective GPER agonists, such as G-1) can be used to treat and/or prevent not only cancers that are classically responsive to estrogen and other sex hormones including (for example, cancers developing in a reproductive tissue, such as but not limited to breast cancer, ovarian cancer, prostate cancer, and/or endometrial cancer), but also any cancer where the cancer cells express GPER or any another GPCR, such as but not limited to a Myc-expressing cancer. Without wishing to be limited by any theory, the estrogen and/or GPCR agonist binds to the GPCR, causing downregulation of Myc in the cancer cell. As demonstrated in FIG. 19, treatment of a GPER-expressing cell with estrogen or a GPCR agonist (such as G-1 as a selective agonist for GPER) causes a marked depletion of Myc protein, and an unexpected increase in GPER protein. This increase in GPER itself further sensitizes the cancer cell to the effects of G-1 and/or other GPCR agonists.

Figure 5:
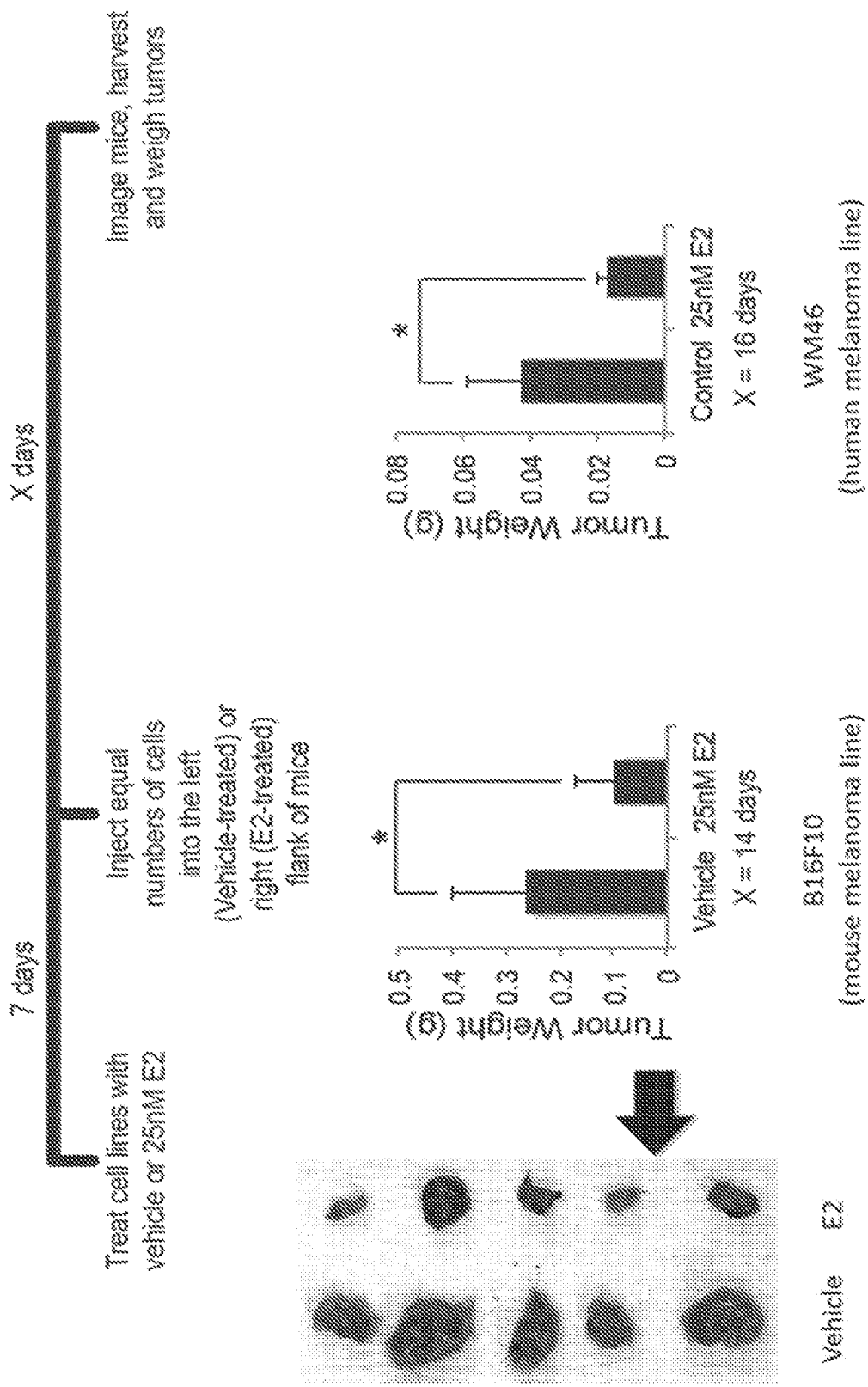
FIG. 5 is a set of graphs and images illustrating the finding that estrogen pretreatment inhibits melanoma cell line growth in vivo.
Figure 6:
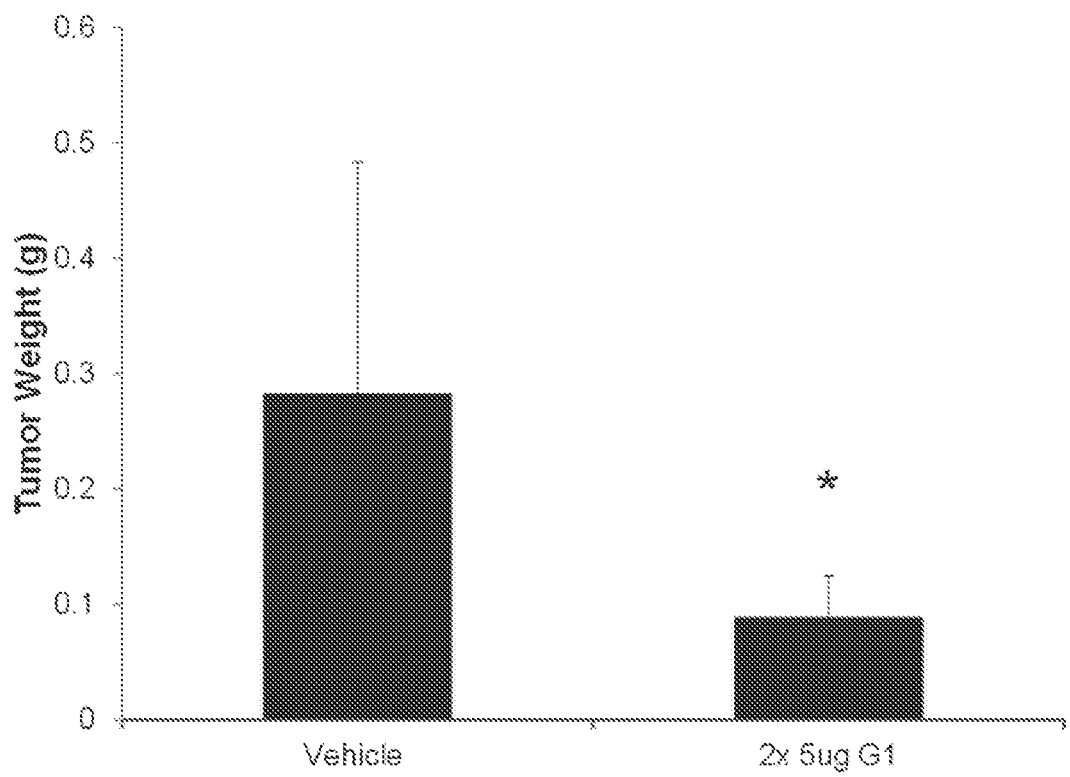
FIG. 6 is a graph illustrating the finding that in vivo treatment with G-1 inhibits mouse melanoma cell line B16F10 growth in vivo.

As shown herein, mouse and human melanoma cells responded similarly to estrogen, which slows tumor cell proliferation. Human and mouse melanoma cells treated with estrogen, or the specific synthetic GPER agonist G-1, grew more slowly in mice, and formed significantly smaller tumors (FIGS. 5-6). A brief onetime exposure to estrogen or G-1 was sufficient for the anti-tumor effect to be observed.

Figure 3:
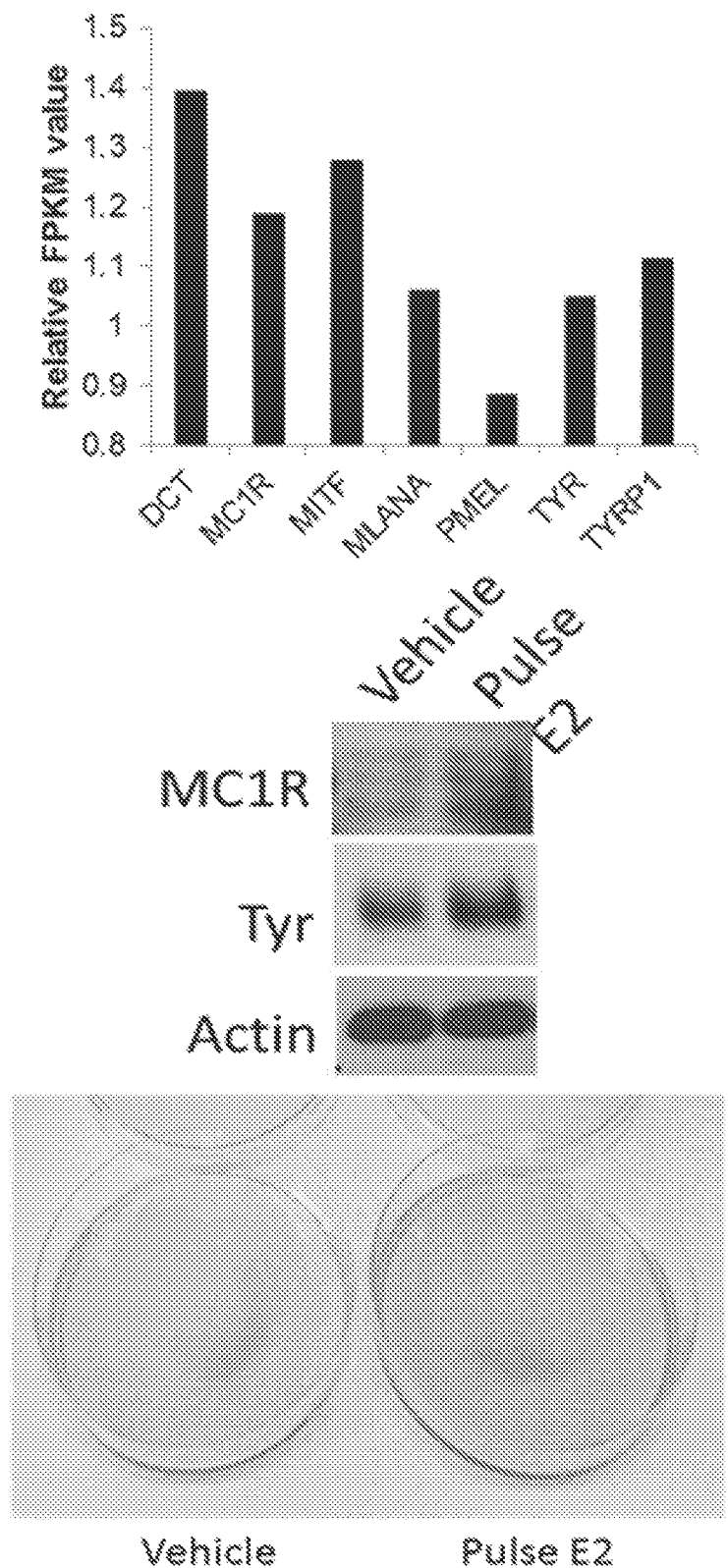
FIG. 3 is a set of graphs and images illustrating the finding that exposure of melanocytes to continuous pregnancy-associated physiologic levels of estrogen increases melanocyte differentiation state, as indicated by increased melanin pigment production. Transient exposure to estrogen for only four days, at the same concentration, induces an identical change in melanocyte differentiation that is durable, and persists indefinitely after estrogen withdrawal.
Figure 4A:
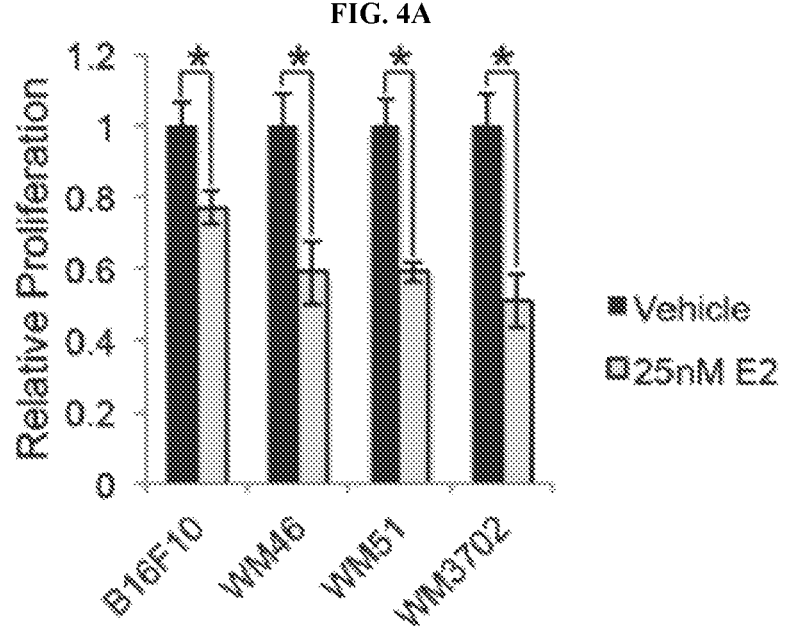
FIGS. 4A-4F illustrate the finding that GPER signaling slows proliferation and drives differentiation in mouse and human melanoma.
Figure 4B:
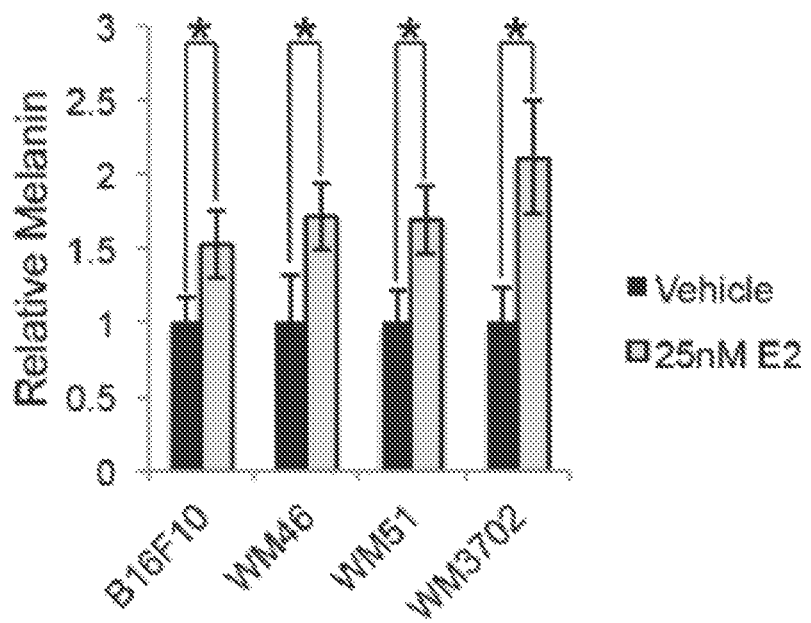
Figure 4C:
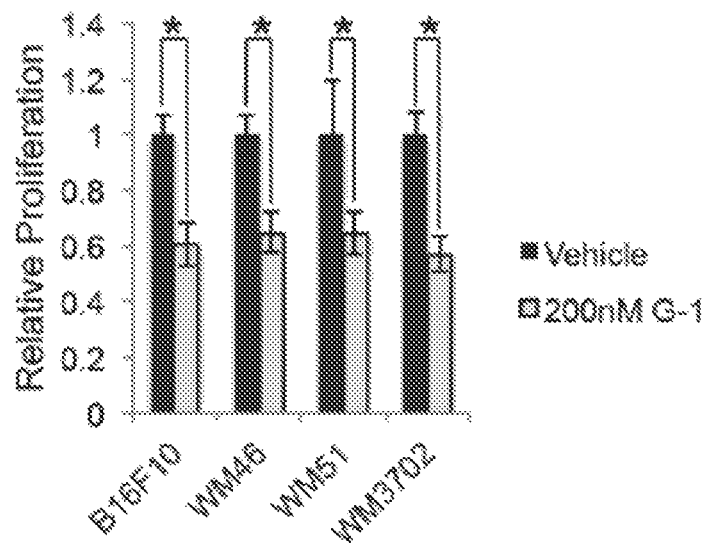
Figure 4D:
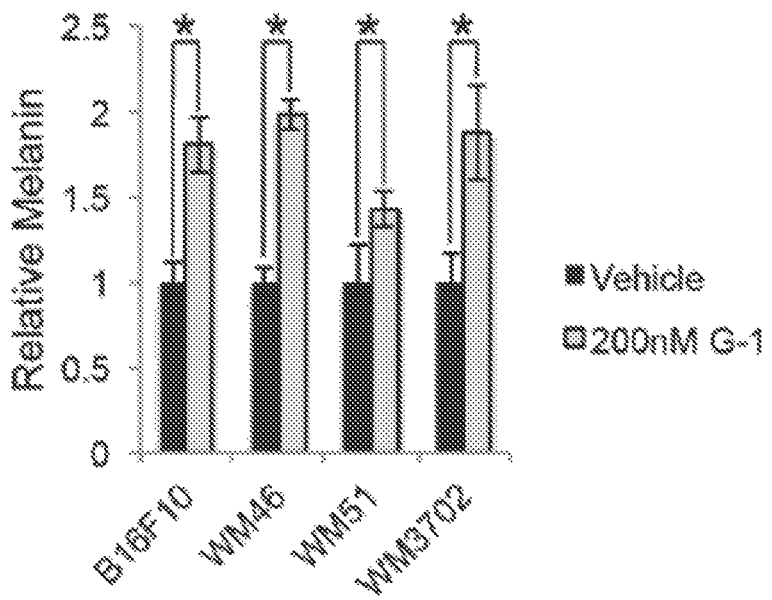
Figure 4E:
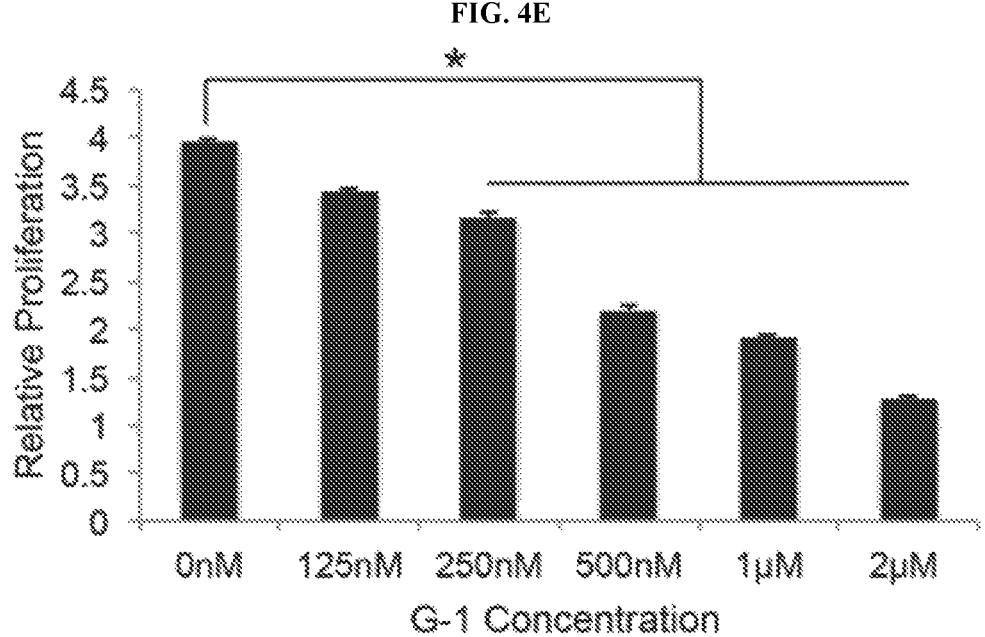
Figure 4F:
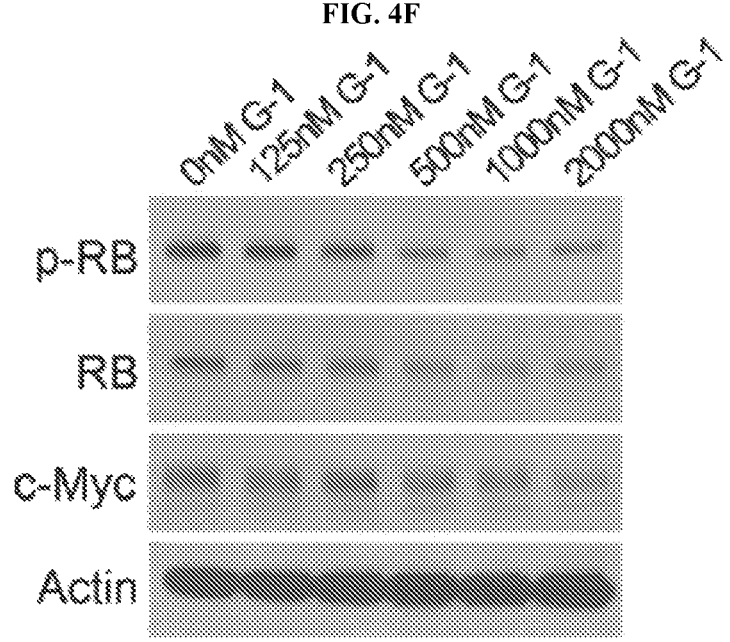

Without wishing to be limited by any theory, transient estrogen exposure was sufficient to induce epigenetic memory that maintains cells in a more differentiated state. Data recited herein show that melanocytes transiently treated with estrogen maintain upregulated expression of many of the major melanocyte differentiation markers, including tyrosinase, tyrosinase related protein, MC1R, Melan-A, and dopachrome tautomerase (FIG. 3).

This discovery helps explain the clinical observation that women with melanoma generally have a better prognosis then men with otherwise identical tumors. Also, women who have had previous pregnancies, and were thus exposed to high concentrations of the GPER agonist estrogen, have a better prognosis when diagnosed with melanoma than age matched, never-childbearing women, and this protection increases with the number of previous pregnancies. Without wishing to be bound by any specific theory, this suggests that the hormonal influences of pregnancy lower melanoma risk.

In certain aspects, treatment (including transient treatment) with estrogen, G-1, or any other GPCR agonist (such as a selective GPER agonist), decreases long-term melanoma risk in both women and men. According to the methods of the invention, the beneficial anti-melanoma effects of pregnancy can be captured in both sexes without having to endure an actual pregnancy.

In certain aspects, GPCR agonist treatment of a melanoma patient helps slow tumor growth and extend overall survival.

In certain aspects, subjects are further treated with a histone deacetylase inhibitor, such as but not limited to valproic acid, vorinostat (SAHA), romidepsin, trichostatin A (TSA), JQ1, or other bromodomain targeting inhibitors. These compounds unexpectedly potentiate the effects of GPCR agonists, including G-1 as a selective GPER agonist.

In certain aspects, subjects are further treated with an anticancer treatment, such as but not limited to chemotherapy, an engineered chimeric antigen receptor (CAR) T-cell, any immunotherapy agent (such as an immune checkpoint inhibitor), and/or radiation therapy. CARs targeting melanoma cells can be based on ectodomain of proteins including, but not limited to, MC1R, HGFR (Met), MART-1, VEGFR, ganglioside GD3, GP100, tyrosinase and NY-ESO-1. Also contemplated within the invention are vaccines directed against differentiation proteins, such as but not limited to MC1R, MART, TYR, and/or DCT.

Immune checkpoint therapy (such as, but not limited to, inhibitors targeting PD-1 and/or CTLA4) works by activating cytotoxic T-cells that recognize antigens on tumor cells. These antigens on melanoma often include melanocyte differentiation markers (tyrosinase, tyrosinase related protein, MC1R, Melan-A, and dopachrome tautomerase). Treatment of a subject with estrogen, G-1, or any other GPCR agonist (such as a GPER agonist) increases the expression of these antigenic proteins. In certain embodiments, treatment of a subject with estrogen and/or a GPER agonist increases the efficacy of immunotherapy, including current standard-of-care regimens with immune checkpoint inhibitors and/or vaccines directed against differentiation proteins.

In certain embodiments, subjects at increased risk of melanoma (for examples, subject with prior melanoma occurrences, melanoma family history, and/or transplant recipient), or any other type of GPCR-expressing (such as a GPER-expressing) and/or Myc-expressing cancer, can benefit from treatment with estrogen and/or a GPCR agonist (such as a selective GPER agonist). In other embodiments, a general subject can benefit from treatment with estrogen and/or a GPCR agonist (such as a selective GPER agonist), which acts as a preventive or maintenance treatment against future occurrences of a GPCR-expressing (such as a GPER-expressing) and/or Myc-expressing cancer. In yet other embodiments, current cancer patients can benefit from treatment with estrogen and/or a GPCR agonist (such as a selective GPER agonist), either alone, in combination with a HDAC, and/or in combination with any other therapies, including, but not limited to, immunotherapies (using for example immune checkpoint inhibitors), targeted chemotherapies, traditional nonselective chemotherapies, or radiation therapy.

In certain embodiments, estrogen and/or GPER agonist (such as G-1), and/or any other GPCR agonist is formulated for oral administration (for example, as pills), intravenous or intramuscular administration, and/or topical administration (for example, topical creams, gels and/or ointments). In other embodiments, estrogen, the GPER agonist (such as G-1), and/or other GPCR agonist is used to decrease the likelihood that a benign mole (i.e., melanocytic nevus) develops into a melanoma.

Figure 9:
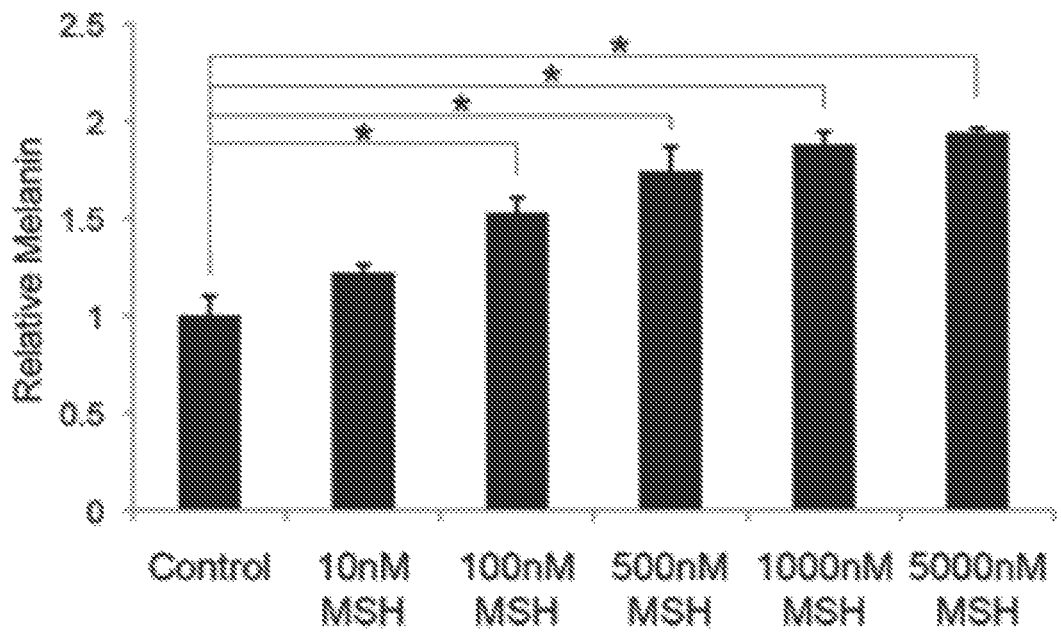
FIG. 9 is a set of bar graphs illustrating the finding that MSH (the endogenous equivalent of afamelanotide) and afamelanotide (also known as melanotide II or NDP-α-MSH) increase pigment production (top) and differentiation (bottom) in human melanocytes.
Figure 9:
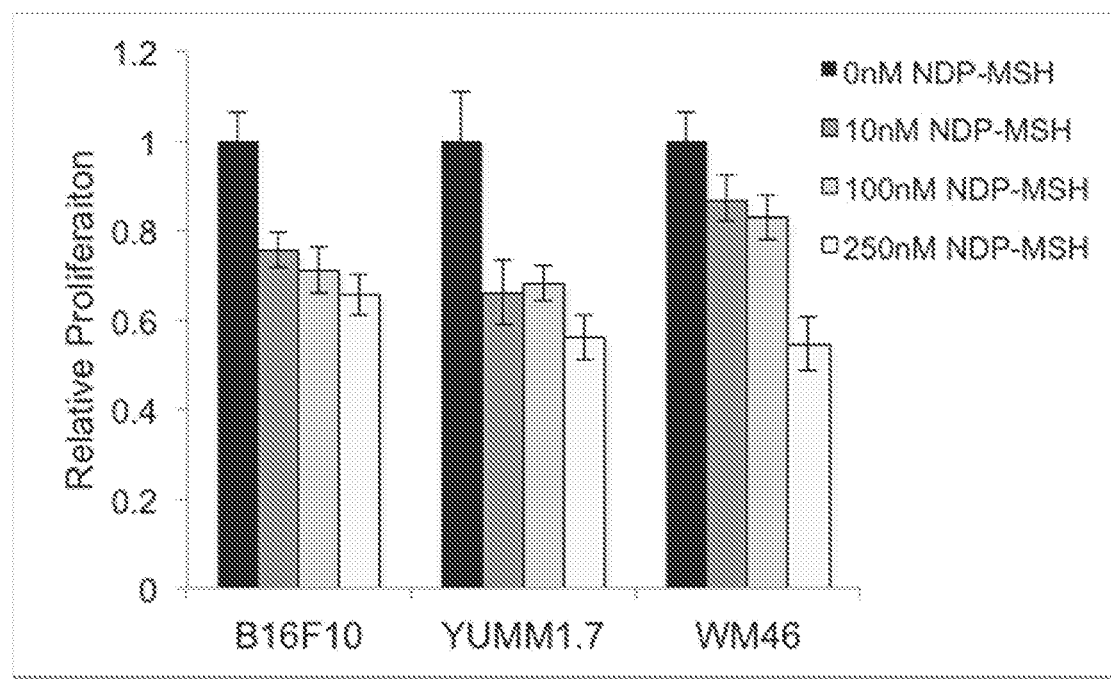
Figure 10A:
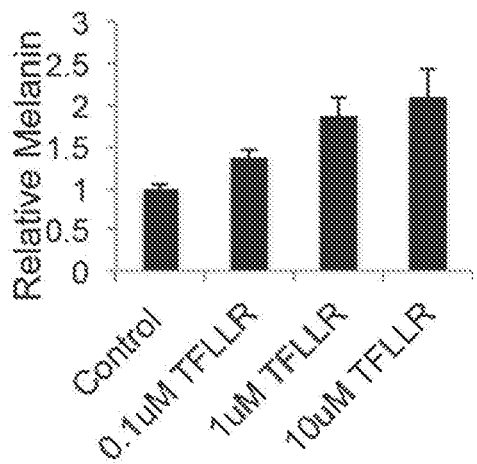
FIGS. 10A-10D are a set of bar graphs illustrating the finding that certain agonists of inflammation associated melanocyte GPCRs (CCR10, F2R, PTGER1, and TBXA2R) modulate melanin synthesis in human melanocytes.
Figure 10B:
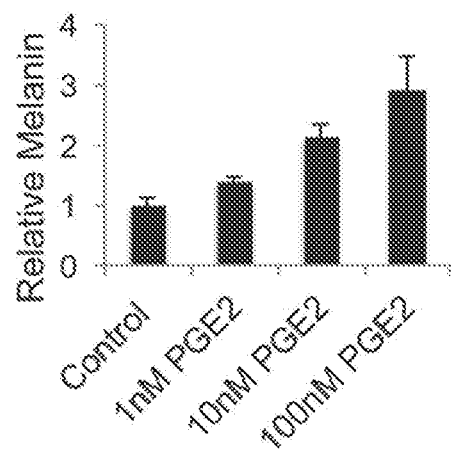
Figure 10C:
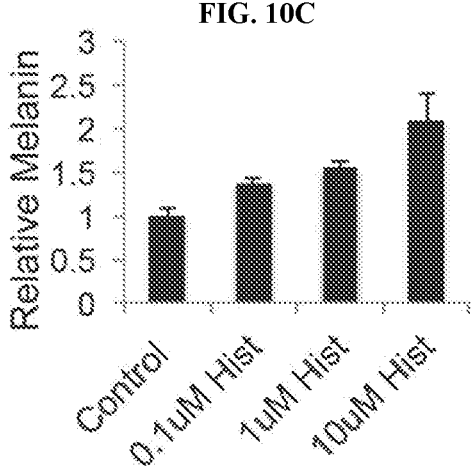
Figure 10D:
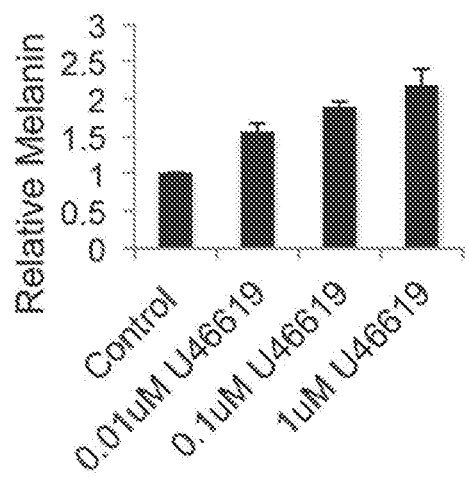

The present invention should not be construed to be limited to use of GPER agonists in the treatment of GPCR-expressing (such as a GPER-expressing) and/or Myc-expressing cancers, such as but not limited to melanoma. In addition to GPER, melanocytes and tumor arising in other tissue types express other G protein-coupled receptors (melanocyte GPCRs highlighted in Table 1) that, when activated, signal through the same downstream pathways as GPER to similarly drive differentiation (FIG. 9). In certain embodiments, agonists for these receptors have anti-tumor activity, either alone and/or in combination with other therapeutic agents including, but not limited to, immunotherapeutics. Non-limiting examples of such receptor ligands include MSH peptide derivatives such as afamelanotide, also known as melanotide II or NDP-α-MSH. FIGS. 10A-10D illustrate how certain agonists of inflammation melanocyte GPCRs modulate melanin synthesis in human melanocytes. As such, GPCR agonists that increase melanocyte differentiation are useful within the present invention. In certain embodiments, non-limiting examples of such GPCR agonists includes agonists towards MC1R, CYSLTR2, F2R, HRH2, LPAR2/3/6, PTGER1, S1PR$_2$, S1PR$_3$, and/or TBXA$_2$R. In other embodiments, non-limiting examples of such GPCR agonists includes agonists towards F2R, PTGER1, and/or TBXA$_2$R. In yet other embodiments, non-limiting examples of agonists useful within the invention include afamelanotide (N-acetyl-L-seryl-L-tyrosyl-L-seryl-L-norleucyl-L-α-glutamyl-L-histidyl-D-phenylalanyl-L-arginyl-L-tryptophylglycyl-L-lysyl-L-prolyl-L-valinamide), N-methyl LTC4 (N-methyl-5S-hydroxy-6R-(S-glutathionyl)-7E,9E,11Z, 14Z-eicosatetraenoic acid), TFLLR-NH$_2$ (Thr-Phe-Leu-Leu-Arg-NH$_2$), Impromidine (2-[3-(1H-imidazol-5-yl)propyl]-1-[2-[(5-methyl-1H-imidazol-4-yl)methylsulfanyl] ethyl]guanidine), Carbachol (2-[(Aminocarbonyl)oxy]-N,N, N-trimethyl ethanaminium chloride), Sulprostone ((Z)-7-[(1R,3R)-3-hydroxy-2-[(E,3R)-3-hydroxy-4-phenoxybut-1-enyl]-5-oxocyclopentyl]-N-methylsulfonylhept-5-enamide), FTY720 (2-Amino-2-[2-(4-octyl-phenyl)-ethyl]-propane-1,3-diol hydrochloride, or Fingolimod hydrochloride) and U46619 ((E)-7-((1R,4R,5S,6R)-6-((S,Z)-3-hydroxyoct-1-en-1-yl)-2-oxabicyclo[2.2.1]heptan-5-yl)hept-5-enoic acid).

TABLE 1

Melanocyte GPCRs that promote cell differentiation and melanin pigment production when activated by natural or synthetic ligands.

| Receptor | Natural Ligand | G Protein | Agonist | Antagonist |
|---|---|---|---|---|
| MC1R | α-MSH | Gs | afamelanotide | |
| CCR10 | CCL27 | $G_i$ | N/A | N/A |
| CYSLTR2 | Cysteinyl-leukotriene | $G_q$ | N-methyl $LTC_4$ | Pranlukast |
| F2R | Thrombin | $G_{q/11}$, $G_i$, and $G_{12/13}$ | TFLLR-$NH_2$ | Vorapaxar |
| HRH2 | Histamine | $G_s$ | Impromidine | Nizatidine |
| LPAR2/3/6 | Lysophosphatidic Acid | $G_q$ $G_i$ | Carbachol | dioctyl-glycerol |
| PTGER1 | Prostaglandin E2 | $G_q$ | Sulprostone | SC19220 |
| $S1PR_2$, $S1PR_3$ | Sphingosine-1-Phosphate | $G_q$ $G_i$ | FTY720 | JTE-013 |
| $TBXA_2R$ | Thromboxane A2 | $G_q$ | U46619 | ICI 185,282 |

Definitions

As used herein, each of the following terms have the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics and chemistry are those well-known and commonly employed in the art.

The articles "a" and "an" are used herein to refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, ±5%, ±1%, or ±0.1% from the specified value, as such variations are appropriate to perform the disclosed methods.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is ($C_1$-$C_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is ($C_1$-$C_4$)alkyl, such as, but not limited to, ethyl, methyl, isopropyl, n-butyl, isobutyl, t-butyl, and cyclopropylmethyl.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

As used herein "endogenous" refers to any material from or produced inside an organism, cell, tissue or system.

"Estrogen" or "oestrogen" as used herein refers to any substance, natural or synthetic (including analogues and derivatives of estrogen), that mimics the effect of the natural hormone, estrogen. Types of estrogen include, but are not limited to, estrone (E1), estradiol (E2), estriol (E3), estetrol (E4), 17β-estradiol, 27-hydroxycholesterol, dehydroepiandrosterone (DHEA), 7-oxo-DHEA, 7α-hydroxy-DHEA, 16α-hydroxy-DHEA, 7β-hydroxyepiandrosterone, $\Delta^4$-androstenedione, $\Delta^5$-androstenediol, 3α-androstanediol, 3β-androstanediol, 2-hydroxyestrone, 16-hydroxyestrone, estradiol cypionate, estradiol valerate, estradiol acetate, estradiol benzoate, ethinyl estradiol (EE), mestranol, moxestrol, quinestrol, diethylstilbestrol benzestrol, dienestrol, dienestrol acetate, diethylstilbestrol dipropionate, fosfestrol, hexestrol, methestrol dipropionate, xenoestrogens, phytoestrogens, and/or mycoestrogens.

As used herein, the term "halo" or "halogen" alone or as part of another substituent refers to, unless otherwise stated, a fluorine, chlorine, bromine, or iodine atom.

As used herein, the term "GPCR" refers to G-protein coupled receptor.

As used herein, the term "GPER" refers to a G protein-coupled estrogen receptor, which is a type of GPCR.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

As used herein, "immune checkpoint inhibitor" refers to a drug (such as a small molecule, peptide and/or antibody) that triggers an immune system attack on cancer cells. Examples of immune checkpoint inhibitors include, but are not limited to, antibodies, PD-1 inhibitors (i.e. Pembrolizumab, Nivolumab, anti-PD-1), PD-L1 inhibitors (i.e. Atezolizumab, anti-PD-L1), CTLA-4 inhibitors (i.e. Ipilimumab, anti-B7-1/B7-2, anti-CTLA-4), Indoleamine (2,3)-dioxygenase (IDO1/2) inhibitors, B7 homolog 3 (B7-H3) inhibitors, lymphocyte activation gene 3 (LAG3) inhibitors, and TIGIT (T cell immunoreceptor with Ig and ITIM domains) targeting antibodies and agents.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

As used herein, the term "Myc-expressing cancer" refers to a type of cancer which origination and/or propagation depends on and/or is accelerated by Myc activation, dysregulation, mutation, and/or abnormal function. Non-limiting examples of Myc-expressing cancers include melanoma, Burkitt lymphoma, leukemia, sarcoma, lymphoma, multiple myeloma, brain cancer, neuroblastoma, medulloblastoma, astrocytoma, glioblastoma, ovarian cancer, cervix cancer, uterine cancer, colorectal cancer, breast cancer, pancreatic cancer, lung cancer, stomach cancer, thyroid cancer, liver cancer, prostate cancer, esophagus cancer, kidney cancer, bladder cancer, and gall bladder cancer.

"Parenteral" administration of an immunogenic composition includes, e.g., subcutaneous (s.c.), intravenous (i.v.), intramuscular (i.m.), or intrasternal injection, or infusion techniques.

As used herein, the term "pharmaceutical composition" or "composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary, intracranial, transdermal and topical administration. In certain embodiments, the administration comprises topical administration.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

As used herein, a "pharmaceutically effective amount," "therapeutically effective amount" or "effective amount" of a compound is that amount of compound that is sufficient to provide a beneficial effect to the subject to which the compound is administered.

The term "prevent," "preventing" or "prevention" as used herein means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds" as used herein is meant that a first molecule preferentially binds to a second molecule (e.g., a particular receptor or enzyme), but does not necessarily bind only to that second molecule.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell that has been separated from other cell types with which it is normally associated in its naturally occurring state. In certain embodiments, a population of substantially purified cells refers to a homogenous population of cells. In other embodiments, this term refers simply to cell that have been separated from the cells with which they are naturally associated in their natural state. In yet other embodiments, the cells are cultured in vitro. In yet other embodiments, the cells are not cultured in vitro.

The term "therapeutic" as used herein means a treatment and/or prophylaxis. A therapeutic effect is obtained by suppression, remission, or eradication of a disease state.

As used herein, "topical administration" or "topical application" refers to a medication applied to body surfaces such as the skin or mucous membranes.

To "treat" a disease as the term is used herein, means to reduce the frequency or severity of at least one sign or symptom of a disease or disorder experienced by a subject.

As used herein, the term "treatment" or "treating" is defined as the application or administration of a therapeutic agent, i.e., a composition useful within the invention (alone or in combination with another pharmaceutical agent), to a subject, or application or administration of a therapeutic agent to an isolated tissue or cell line from a subject (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder or the potential to develop the disease or disorder. Such treatments may be specifically tailored or modified, based on knowledge obtained from the field of pharmacogenomics.

As used herein, the term "UV" refers to ultraviolet.

"Xenogeneic" refers to any material derived from an animal of a different species.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

In one aspect, the present invention contemplates estrogen and/or other small molecules that bind to and activate a GPCR, such as the G protein-coupled estrogen receptor GPER. This induces cell signaling events that increase the differentiation state of the tumor cell. This slows tumor cell proliferation, slows overall tumor growth, and renders tumor cells more visible to immune cells and/or susceptible to immunotherapy. In certain embodiments, the present invention contemplates other molecules that serve as agonists of other GPCRs. Such molecules induce cell differentiation by engaging many of the same downstream pathways that are activated by GPER In certain embodiments, the compound of the invention, or a salt, solvate, tautomer, enantiomer or diastereoisomer thereof is at least one compound of formula (I):

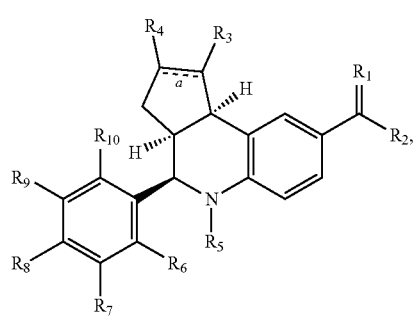

(I)

wherein in (I):

$R_1$ is selected from the group consisting of =O, =N—OH, =N—NHC(=O)(p-methoxy phenyl), =N—NHC(=O)CH(OMe)phenyl, and =N—NH(5-iodo-pyrid-2-yl);

$R_2$ is selected from the group consisting of $C_1$-$C_4$ alkyl and $C_1$-$C_4$ haloalkyl (such as, but not limited to, —$CF_3$);

bond a is a single or double bond, such that:
  if bond a is a double bond, $R_3$ and $R_4$ are H, and
  if bond a is a single bond, $R_3$ is selected from the group consisting of H, —OH,
  —OAc, and halo; $R_4$ is selected from the group consisting of H, —OH, —OAc, and
  —S(o-nitrophenyl); or $R_3$ and $R_4$ combine to form a diradical selected from the group consisting of —$CH_2$—, —$OCH_2O$—, —$OCH(CH_3)O$—, and —$OC(CH_3)_2O$—;

$R_5$ is selected from the group consisting of H, benzyl, $C_1$-$C_4$ alkyl, and acetyl;

$R_6$ is selected from the group consisting of H, halo, —$NO_2$, $C_1$-$C_4$ alkyl, —C≡CH, —C≡C—Si($CH_3$)$_3$ (or —C≡C-TMS), —O-benzyl, —OH, —OAc, $C_1$-$C_4$ alkoxy, —COOH, and —COO($C_1$-$C_4$ alkyl);

$R_7$ is selected from the group consisting of H, halo, —$NO_2$, $C_1$-$C_4$ alkyl, —OH, —OAc, and $C_1$-$C_4$ alkoxy;

$R_8$ is selected from the group consisting of H, halo, —$NO_2$, $C_1$-$C_4$ alkyl, —O-benzyl, —N(R)(R), —SR, —COOH, —COO($C_1$-$C_4$ alkyl), —OH, —OAc, $C_1$-$C_4$ alkoxy, 3-thietyl-methoxy, —$SO_2$(morpholino), and —$OCH_2CH$=$CH_2$, wherein each occurrence of R is independently selected from the group consisting of H and $C_1$-$C_4$ alkyl;

$R_9$ is selected from the group consisting of H, halo, —$NO_2$, $C_1$-$C_4$ alkyl, —OH, —OAc, and $C_1$-$C_4$ alkoxy,
  or $R_8$ and $R_9$ combine to form a diradical selected from the group consisting of —$OCH_2O$—, —$OCH(CH_3)O$—, —$OC(CH_3)_2O$—, —$O(CH_2)_2O$—, —O—CH=CH—, and —CH=CH—O—;

$R_{10}$ is selected from the group consisting of H, $C_1$-$C_4$ alkyl, and halo;

wherein each occurrence of benzyl is independently optionally substituted with at least one group selected from the group consisting of $C_1$-$C_4$ alkyl, —OH, $C_1$-$C_4$ alkoxy, halo, and —$NO_2$.

In certain embodiments, the compound of the invention, or a salt, solvate, tautomer, enantiomer or diastereoisomer thereof, is at least one compound of formula (I-1):

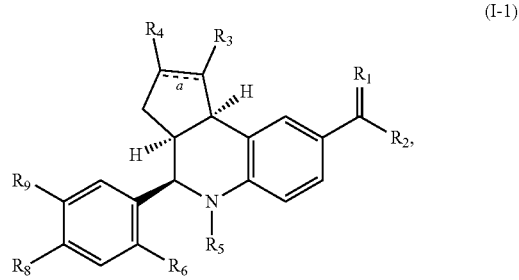

(I-1)

wherein in (I-1):
R₁ is selected from the group consisting of =O and =N—OH;
R₂ is C₁-C₄ alkyl;
bond a is a single or double bond, such that:
  if bond a is a double bond, R₃ and R₄ are H, and
  if bond a is a single bond, R₃ and R₄ are independently selected from the group consisting of H and —OH, or R₃ and R₄ combine to form a diradical selected from the group consisting of —OCH₂O—, —OCH(CH₃)O— and —OC(CH₃)₂O—;
R₅ is selected from the group consisting of H, benzyl and C₁-C₄ alkyl;
R₆ is selected from the group consisting of H and halo;
R₈ and R₉ are independently selected from the group consisting of H and C₁-C₄ alkoxy, or R₈ and R₉ combine to form a diradical selected from the group consisting of —OCH₂O—, —OCH(CH₃)O— and —OC(CH₃)₂O—.

In certain embodiments, the compound is not G-1. In other embodiments, the compound is G-1.

In certain embodiments, R₁ is =O. In other embodiments, R₁ is =N—OH.

In certain embodiments, R₂ is selected from the group consisting of methyl, trifluoromethyl, ethyl, 1-propyl, and 2-propyl. In other embodiments, R₂ is methyl or trifluoromethyl.

In certain embodiments, bond a is a double bond, and R₃ and R₄ are H.

In certain embodiments, bond a is a single bond, and R₃ and R₄ are independently selected from the group consisting of H and —OH. In other embodiments, bond a is a single bond, and R₃ and R₄ are H. In yet other embodiments, bond a is a single bond, and R₃ and R₄ are —OH. In yet other embodiments, bond a is a single bond, and R₃ and R₄ are —OH and cis to each other. In yet other embodiments, bond a is a single bond, and R₃ and R₄ are —OH and trans to each other.

In certain embodiments, bond a is a single bond, and R₃ and R₄ combine to form —OC(CH₃)₂O—.

In certain embodiments, R₅ is selected from the group consisting of H, benzyl, methyl, ethyl, 1-propyl and 2-propyl. In certain embodiments, R₅ is selected from the group consisting of H, benzyl and methyl.

In certain embodiments, R₆ is selected from the group consisting of H, F, Cl, Br and I. In certain embodiments, R₅ is selected from the group consisting of H, Cl and Br.

In certain embodiments, R₈ and R₉ are independently selected from the group consisting of H and C₁-C₄ alkoxy. In other embodiments, R₈ and R₉ are independently selected from the group consisting of H, methoxy, ethoxy, 1-propoxy and 2-propoxy. In yet other embodiments, R₈ and R₉ are independently selected from the group consisting of H and methoxy.

In certain embodiments, R₈ and R₉ combine to form a diradical selected from the group consisting of —OCH₂O—, —O(CH₂)₂O—, —OCH(CH₃)O— and —OC(CH₃)₂O—.

In certain embodiments, the compound, or a salt, solvate, tautomer, enantiomer or diastereoisomer thereof, is at least one selected from the group consisting of:

In certain embodiments, the compound, or a salt, solvate, tautomer, enantiomer or diastereoisomer thereof, is at least one selected from the group consisting of:

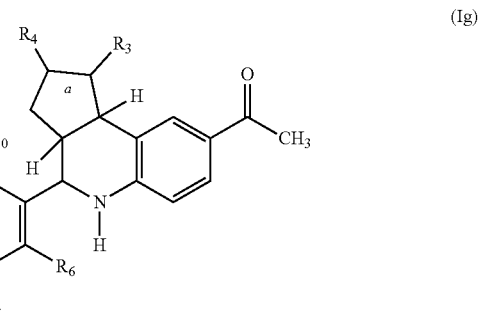

(Ig)

| Compound | $R_6$ | $R_7$ | $R_8$ | $R_9$ | $R_{10}$ | $R_4$ | $R_3$ |
|---|---|---|---|---|---|---|---|
| A1 | H | H | OMe | H | H | H | H |
| A2 | Cl | H | H | H | H | H | H |
| A3 | Cl | H | Cl | H | H | H | H |
| A4 | H | H | H | H | H | H | H |
| A5 | H | H | —OCH$_2$CH$_2$O— | | H | H | H |
| A6 | Br | H | —OCH$_2$CH$_2$O— | | H | H | H |
| A7 | H | H | H | H | H | —CH$_2$— | |
| A8 | H | H | H | H | H | S(o-NO$_2$)Ph | Cl |
| A9 | H | H | Br | H | H | S(o-NO$_2$)Ph | Cl |
| A10 | H | H | Cl | H | H | S(o-NO$_2$)Ph | Cl |
| A11 | F | H | H | H | H | S(o-NO$_2$)Ph | Cl |
| A12 | H | H | NO$_2$ | H | H | S(o-NO$_2$)Ph | Cl |
| A13 | NO$_2$ | H | H | H | H | S(o-NO$_2$)Ph | Cl |
| A14 | Cl | H | Cl | H | H | S(o-NO$_2$)Ph | Cl |
| A15 | Cl | Cl | H | H | H | S(o-NO$_2$)Ph | Cl |

In certain embodiments, the compound is A1. In other embodiments, the compound is A2. In yet other embodiments, the compound is A3. In yet other embodiments, the compound is A4. In yet other embodiments, the compound is A5. In yet other embodiments, the compound is A6. In yet other embodiments, the compound is A7. In yet other embodiments, the compound is A8. In yet other embodiments, the compound is A9. In yet other embodiments, the compound is A10. In yet other embodiments, the compound is A11. In yet other embodiments, the compound is A12. In yet other embodiments, the compound is A13. In yet other embodiments, the compound is A14. In yet other embodiments, the compound is A15.

In certain embodiments, the compound is not A1. In other embodiments, the compound is not A2. In yet other embodiments, the compound is not A3. In yet other embodiments, the compound is not A4. In yet other embodiments, the compound is not A5. In yet other embodiments, the compound is not A6. In yet other embodiments, the compound is not A7. In yet other embodiments, the compound is not A8. In yet other embodiments, the compound is not A9. In yet other embodiments, the compound is not A10. In yet other embodiments, the compound is not A11. In yet other embodiments, the compound is not A12. In yet other embodiments, the compound is not A13. In yet other embodiments, the compound is not A14. In yet other embodiments, the compound is not A15.

In certain embodiments, the compound, or a salt, solvate, tautomer, enantiomer or diastereoisomer thereof, is at least one selected from the group consisting of:

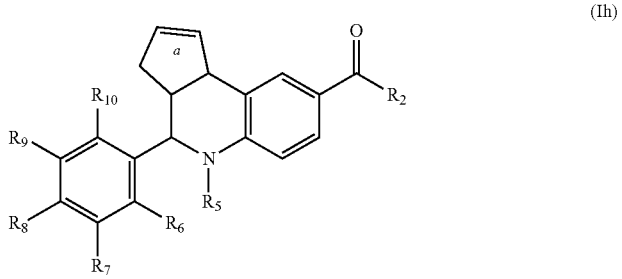

(Ih)

| Compound | $R_6$ | $R_7$ | $R_8$ | $R_9$ | $R_{10}$ | $R_2$ | $R_5$ |
|---|---|---|---|---|---|---|---|
| A16 | H | H | CH$_3$ | H | H | CH$_3$ | H |
| A17 | H | CH$_3$ | H | H | H | CH$_3$ | H |
| A18 | H | H | OH | H | H | CH$_3$ | H |

-continued

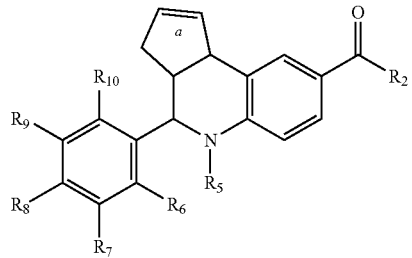

(Ih)

| Compound | R₆ | R₇ | R₈ | R₉ | R₁₀ | R₂ | R₅ |
|---|---|---|---|---|---|---|---|
| A19 | CH₃ | H | H | H | H | CH₃ | H |
| A20 | H | H | iPr | H | H | CH₃ | H |
| A21 | H | OH | H | H | H | CH₃ | H |
| A22 | H | H | Br | H | H | CH₃ | H |
| A23 | H | H | Cl | H | H | CH₃ | H |
| A24 | H | H | F | H | H | CH₃ | H |
| A25 | OH | H | H | H | H | CH₃ | H |
| A26 | H | H | OCH₃ | H | H | CH₃ | H |
| A27 | H | Cl | H | H | H | CH₃ | H |
| A28 | H | Br | H | H | H | CH₃ | H |
| A29 | H | F | H | H | H | CH₃ | H |
| A30 | H | H | N(CH₃)₂ | H | H | CH₃ | H |
| A31 | H | H | SCH₃ | H | H | CH₃ | H |
| A32 | Cl | H | H | H | H | CH₃ | H |
| A33 | F | H | H | H | H | CH₃ | H |
| A34 | H | H | OEt | H | H | CH₃ | H |
| A35 | Br | H | H | H | H | CH₃ | H |
| A36 | H | H | COOH | H | H | CH₃ | H |
| A37 | CH₃ | H | CH₃ | H | CH₃ | CH₃ | H |
| A38 | CH₃ | H | H | CH₃ | H | CH₃ | H |
| A39 | H | OCH₃ | H | H | H | CH₃ | H |
| A40 | H | H | OiPr | H | H | CH₃ | H |
| A41 | OCH₃ | H | H | H | H | CH₃ | H |
| A42 | H | H | NO₂ | H | H | CH₃ | H |
| A43 | OEt | H | H | H | H | CH₃ | H |
| A44 | H | —CH=CH—O— | | H | H | CH₃ | H |
| A45 | H | H | NEt₂ | H | H | CH₃ | H |
| A46 | H | OH | OH | H | H | CH₃ | H |
| A47 | H | NO₂ | H | H | H | CH₃ | H |
| A48 | Cl | H | H | H | Cl | CH₃ | H |
| A49 | OH | H | OH | H | H | CH₃ | H |
| A50 | Cl | H | H | H | F | CH₃ | H |
| A51 | H | H | COOCH₃ | H | H | CH₃ | H |
| A52 | H | Cl | Cl | H | H | CH₃ | H |
| A53 | H | H | —OCH₂CH=CH₂ | H | H | CH₃ | H |
| A54 | Cl | Cl | H | H | H | CH₃ | H |
| A55 | Cl | H | Cl | H | H | CH₃ | H |
| A56 | NO₂ | H | H | H | H | CH₃ | H |
| A57 | H | H | OAc | H | H | CH₃ | H |
| A58 | H | OH | OCH₃ | H | H | CH₃ | H |
| A59 | H | —OCH₂O— | | H | H | CH₃ | H |
| A60 | OH | H | H | Br | H | CH₃ | H |
| A61 | H | OCH₃ | OH | H | H | CH₃ | H |
| A62 | H | H | OCH₂Ph | H | H | CH₃ | H |
| A63 | OH | OCH₃ | H | H | H | CH₃ | H |
| A64 | H | H | —OCH₂Ph(p-Me) | H | H | CH₃ | H |
| A65 | OCH₃ | H | OCH₃ | H | H | CH₃ | H |
| A66 | H | OCH₃ | OCH₃ | H | H | CH₃ | H |
| A67 | Br | H | OCH₃ | H | H | CH₃ | H |
| A68 | H | H | 3-thietyl-methoxy | H | H | CH₃ | H |
| A69 | OCH₃ | H | H | OMe | H | CH₃ | H |
| A70 | OCH₃ | OCH₃ | H | H | H | CH₃ | H |
| A71 | OCH₃ | H | H | Br | H | CH₃ | H |
| A72 | OH | Cl | H | Cl | H | CH₃ | H |
| A73 | OCH₂Ph | H | H | H | H | CH₃ | H |
| A74 | H | NO₂ | Cl | H | H | CH₃ | H |
| A75 | H | OCH₃ | OCH₃ | OCH₃ | H | CH₃ | H |
| A76 | H | OH | OH | H | Br | CH₃ | H |
| A77 | H | H | —OCH₂Ph(p-Cl) | H | H | CH₃ | H |
| A78 | —C≡CH | H | —OCH₂CH₂O— | | H | CH₃ | H |
| A79 | Cl | H | H | NO₂ | H | CH₃ | H |
| A80 | OH | H | H | NO₂ | H | CH₃ | H |
| A81 | H | H | —OCH₂Ph(o-Cl) | H | H | CH₃ | H |

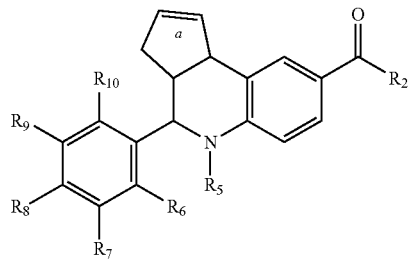

(Ih)

| Compound | R$_6$ | R$_7$ | R$_8$ | R$_9$ | R$_{10}$ | R$_2$ | R$_5$ |
|---|---|---|---|---|---|---|---|
| A82 | H | NO$_2$ | OCH$_3$ | H | H | CH$_3$ | H |
| A83 | Cl | H | Cl | H | H | CF$_3$ | H |
| A84 | H | H | —OCH$_2$Ph(p-NO$_2$) | H | H | CH$_3$ | H |
| A85 | Br | H | —OCH$_2$CH$_2$O— | | H | CH$_3$ | H |
| A86 | Br | H | —OCH$_2$O— | | H | CH$_3$ | H |
| A87 | I | H | —OCH$_2$O— | | H | CH$_3$ | H |
| A88 | H | OCH$_3$ | OAc | H | H | CH$_3$ | H |
| A89 | H | OCH$_3$ | —OCH$_2$Ph | H | H | CH$_3$ | H |
| A90 | Br | | —OCH$_2$O— | H | H | CH$_3$ | H |
| A91 | OAc | H | OAc | H | H | CH$_3$ | H |
| A92 | —C≡C-TMS | H | —OCH$_2$O— | | H | CH$_3$ | H |
| A93 | H | H | —SO$_2$-morpholino | H | H | CH$_3$ | H |
| A94 | H | H | F | H | H | CH$_3$ | H |
| A95 | Br | H | —OCH$_2$O— | | H | CH$_3$ | Me |
| A96 | H | OEt | —OCH$_2$Ph(p-Cl) | H | H | CH$_3$ | H |
| A97 | NO$_2$ | H | —OCH$_2$O— | | H | CH$_3$ | H |
| A98 | Br | H | —OCH$_2$O— | | H | CH$_3$ | H |
| A99 | H | OCH$_3$ | —OCH$_2$Ph | Br | H | CH$_3$ | H |
| A100 | H | OCH$_3$ | —OCH$_2$Ph(p-Me) | Br | H | CH$_3$ | H |
| A101 | H | OCH$_3$ | —OCH$_2$Ph(o-Cl) | Br | H | CH$_3$ | H |
| A102 | Br | H | —OCH$_2$O— | | H | CH$_3$ | Ac |
| A103 | H | OCH$_3$ | —OCH$_2$Ph(m-Cl,p-Cl) | Br | H | CH$_3$ | H |
| A104 | H | OCH$_3$ | —OCH$_2$Ph(o-Cl,p-Cl) | Br | H | CH$_3$ | H |

In certain embodiments, the compound is A16. In other embodiments, the compound is A17. In yet other embodiments, the compound is A18. In yet other embodiments, the compound is A19. In yet other embodiments, the compound is A20. In yet other embodiments, the compound is A21. In yet other embodiments, the compound is A22. In yet other embodiments, the compound is A23. In yet other embodiments, the compound is A24. In yet other embodiments, the compound is A25. In yet other embodiments, the compound is A26. In yet other embodiments, the compound is A27. In yet other embodiments, the compound is A28. In yet other embodiments, the compound is A29. In yet other embodiments, the compound is A30. In yet other embodiments, the compound is A31. In yet other embodiments, the compound is A32. In yet other embodiments, the compound is A33. In yet other embodiments, the compound is A34. In yet other embodiments, the compound is A35. In yet other embodiments, the compound is A36. In yet other embodiments, the compound is A37. In yet other embodiments, the compound is A38. In yet other embodiments, the compound is A39. In yet other embodiments, the compound is A40. In yet other embodiments, the compound is A41. In yet other embodiments, the compound is A42. In yet other embodiments, the compound is A43. In yet other embodiments, the compound is A44. In yet other embodiments, the compound is A45. In yet other embodiments, the compound is A46. In yet other embodiments, the compound is A47. In yet other embodiments, the compound is A48. In yet other embodiments, the compound is A49. In yet other embodiments, the compound is A50. In yet other embodiments, the compound is A51. In yet other embodiments, the compound is A52. In yet other embodiments, the compound is A53. In yet other embodiments, the compound is A54. In yet other embodiments, the compound is A55. In yet other embodiments, the compound is A56. In yet other embodiments, the compound is A57. In yet other embodiments, the compound is A58. In yet other embodiments, the compound is A59. In yet other embodiments, the compound is A60. In yet other embodiments, the compound is A61. In yet other embodiments, the compound is A62. In yet other embodiments, the compound is A63. In yet other embodiments, the compound is A64. In yet other embodiments, the compound is A65. In yet other embodiments, the compound is A66. In yet other embodiments, the compound is A67. In yet other embodiments, the compound is A68. In yet other embodiments, the compound is A69. In yet other embodiments, the compound is A70. In yet other embodiments, the compound is A71. In yet other embodiments, the compound is A72. In yet other embodiments, the compound is A73. In yet other embodiments, the compound is A74. In yet other embodiments, the compound is A75. In yet other embodiments, the compound is A76. In yet other embodiments, the compound is A77. In yet other embodiments, the compound is A78. In yet other embodiments, the compound is A79. In yet other embodiments, the compound is A80. In yet other embodiments, the compound is A81. In yet other embodiments, the compound is A82. In yet other embodiments, the compound is A83. In yet other embodiments, the compound is A84. In yet other embodiments, the compound is A85. In yet other embodiments, the compound is A86. In yet other embodiments, the compound is A87. In yet other embodiments, the compound is A88. In yet other embodiments, the compound is A89. In yet other embodiments, the compound is A90. In yet other embodiments, the compound is A91. In yet other embodiments, the compound is A92. In yet other embodiments, the compound is A93. In yet other embodiments, the compound is A94. In yet other embodiments, the compound is A95. In yet other embodiments, the compound is A96. In yet other embodiments, the compound is A97. In yet other embodiments, the compound is A98. In yet other embodiments, the compound is A99. In yet other embodiments, the compound is A100. In yet other embodiments, the compound is A101. In yet other embodiments, the compound is A102. In yet other embodiments, the compound is A103. In yet other embodiments, the compound is A104.

In certain embodiments, the compound is not A16. In other embodiments, the compound is not A17. In yet other embodiments, the compound is not A18. In yet other embodiments, the compound is not A19. In yet other embodiments, the compound is not A20. In yet other embodiments, the compound is not A21. In yet other embodiments, the compound is not A22. In yet other embodiments, the compound is not A23. In yet other embodiments, the compound is not A24. In yet other embodiments, the compound is not A25. In yet other embodiments, the compound is not A26. In yet other embodiments, the compound is not A27. In yet other embodiments, the compound is not A28. In yet other embodiments, the compound is not A29. In yet other embodiments, the compound is not A30. In yet other embodiments, the compound is not A31. In yet other embodiments, the compound is not A32. In yet other embodiments, the compound is not A33. In yet other embodiments, the compound is not A34. In yet other embodiments, the compound is not A35. In yet other embodiments, the compound is not A36. In yet other embodiments, the compound is not A37. In yet other embodiments, the compound is not A38. In yet other embodiments, the compound is not A39. In yet other embodiments, the compound is not A40. In yet other embodiments, the compound is not A41. In yet other embodiments, the compound is not A42. In yet other embodiments, the compound is not A43. In yet other embodiments, the compound is not A44. In yet other embodiments, the compound is not A45. In yet other embodiments, the compound is not A46. In yet other embodiments, the compound is not A47. In yet other embodiments, the compound is not A48. In yet other embodiments, the compound is not A49. In yet other embodiments, the compound is not A50. In yet other embodiments, the compound is not A51. In yet other embodiments, the compound is not A52. In yet other embodiments, the compound is not A53. In yet other embodiments, the compound is not A54. In yet other embodiments, the compound is not A55. In yet other embodiments, the compound is not A56. In yet other embodiments, the compound is not A57. In yet other embodiments, the compound is not A58. In yet other embodiments, the compound is not A59. In yet other embodiments, the compound is not A60. In yet other embodiments, the compound is not A61. In yet other embodiments, the compound is not A62. In yet other embodiments, the compound is not A63. In yet other embodiments, the compound is not A64. In yet other embodiments, the compound is not A65. In yet other embodiments, the compound is not A66. In yet other embodiments, the compound is not A67. In yet other embodiments, the compound is not A68. In yet other embodiments, the compound is not A69. In yet other embodiments, the compound is not A70. In yet other embodiments, the compound is not A71. In yet other embodiments, the compound is not A72. In yet other embodiments, the compound is not A73. In yet other embodiments, the compound is not A74. In yet other embodiments, the compound is not A75. In yet other embodiments, the compound is not A76. In yet other embodiments, the compound is not A77. In yet other embodiments, the compound is not A78. In yet other embodiments, the compound is not A79. In yet other embodiments, the compound is not A80. In yet other embodiments, the compound is not A81. In yet other embodiments, the compound is not A82. In yet other embodiments, the compound is not A83. In yet other embodiments, the compound is not A84. In yet other embodiments, the compound is not A85. In yet other embodiments, the compound is not A86. In yet other embodiments, the compound is not A87. In yet other embodiments, the compound is not A88. In yet other embodiments, the compound is not A89. In yet other embodiments, the compound is not A90. In yet other embodiments, the compound is not A91. In yet other embodiments, the compound is not A92. In yet other embodiments, the compound is not A93. In yet other embodiments, the compound is not A94. In yet other embodiments, the compound is not A95. In yet other embodiments, the compound is not A96. In yet other embodiments, the compound is not A97. In yet other embodiments, the compound is not A98. In yet other embodiments, the compound is not A99. In yet other embodiments, the compound is not A100. In yet other embodiments, the compound is not A101. In yet other embodiments, the compound is not A102. In yet other embodiments, the compound is not A103. In yet other embodiments, the compound is not A104.

In certain embodiments, the compound of the invention, or a salt, solvate, tautomer, enantiomer or diastereoisomer thereof, is at least one compound selected from the group consisting of:

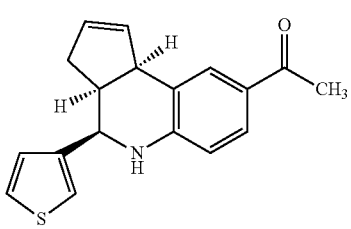

(A105)

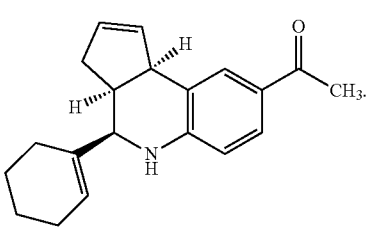

(A106)

In other embodiments, the compound is not A105. In other embodiments, the compound is not A106.

In certain embodiments, the compound of the invention, or a salt, solvate, tautomer, enantiomer or diastereoisomer thereof, is

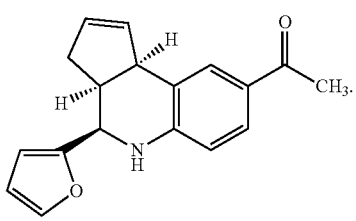

(A107)

In other embodiments, the compound is not A107.

In certain embodiments, the compound is at least one selected from the group consisting of:

G1 or G-1 (rel-1-[4-(6-bromo-1,3-benzodioxol-5-yl)-3aR,4S,5,9bS-tetrahydro-3H-cyclopenta[c]quinolin-8-yl]-ethanone):

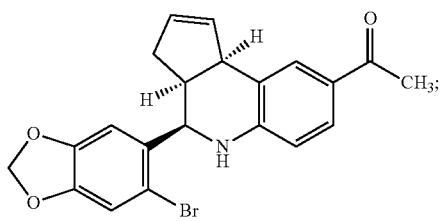 [SMILES: CC(=O)c1ccc2c(c1)[C@@H]1C=CC[C@@H]1[C@H](c1cc3c(cc1Br)OCO3)N2]

CMPD4 (rel-1-((3aS,4R,9bR)-5-benzyl-4-(6-bromobenzo[d][1,3]dioxol-5-yl)-3a,4,5,9b-tetrahydro-3H-cyclopenta[c]quinolin-8-yl)ethan-1-one):

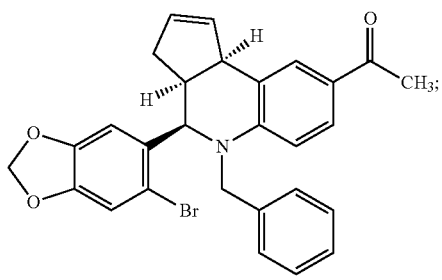 [SMILES: CC(=O)c1ccc2c(c1)[C@@H]1C=CC[C@@H]1[C@H](c1cc3c(cc1Br)OCO3)N2Cc1ccccc1]

CMPD5 (rel-1-((3aS,4R,9bR)-4-(2-bromophenyl)-3a,4,5,9b-tetrahydro-3H-cyclopenta[c]quinolin-8-yl)ethan-1-one):

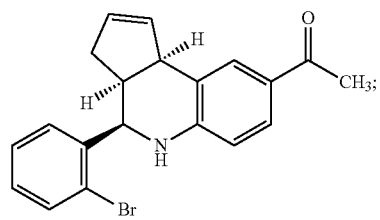 [SMILES: CC(=O)c1ccc2c(c1)[C@@H]1C=CC[C@@H]1[C@H](c1ccccc1Br)N2]

CMPD6 (rel-1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one oxime):

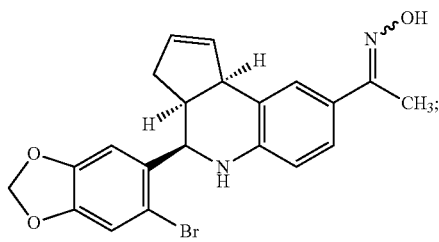 [SMILES: CC(=NO)c1ccc2c(c1)[C@@H]1C=CC[C@@H]1[C@H](c1cc3c(cc1Br)OCO3)N2]

CMPD7 (rel-1-((3aS,4R,9bR)-4-(2-bromo-4,5-dimethoxyphenyl)-3a,4,5,9b-tetrahydro-3H-cyclopenta[c]quinolin-8-yl)ethan-1-one):

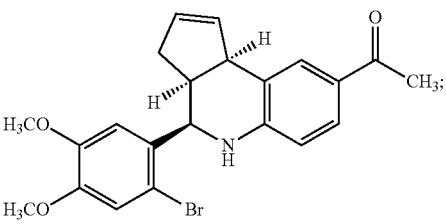 [SMILES: COc1cc(Br)c([C@@H]2Nc3ccc(C(C)=O)cc3[C@@H]3C=CC[C@@H]32)cc1OC]

CMPD8 (rel-1-((3aS,4R,9bR)-4-(6-chlorobenzo[d][1,3]dioxol-5-yl)-3a,4,5,9b-tetrahydro-3H-cyclopenta[c]quinolin-8-yl)ethan-1-one):

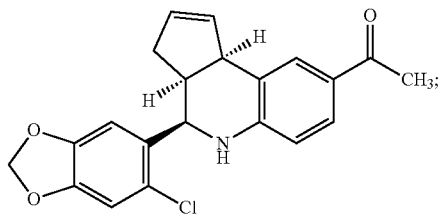 [SMILES: CC(=O)c1ccc2c(c1)[C@@H]1C=CC[C@@H]1[C@H](c1cc3c(cc1Cl)OCO3)N2]

CMPD9 (rel-1-((6R,6aS,7aS,10aR,10bR)-6-(6-bromobenzo[d][1,3]dioxol-5-yl)-9,9-dimethyl-6,6a,7,7a,10a,10b-hexahydro-5H-[1,3]dioxolo[4',5':3,4]cyclopenta[1,2-c]quinolin-2-yl)ethan-1-one):

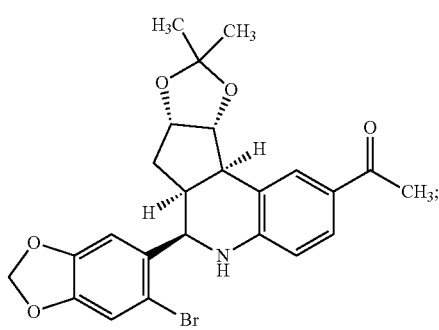 [SMILES: CC(=O)c1ccc2c(c1)[C@H]1[C@H](C[C@@H]3OC(C)(C)O[C@H]13)[C@H](c1cc3c(cc1Br)OCO3)N2]

CMPD10 (rel-1-((1R,2S,3aS,4R,9bR)-4-(6-bromobenzo[d][1,3]dioxol-5-yl)-1,2-dihydroxy-2,3,3a,4,5,9b-hexahydro-1H-cyclopenta[c]quinolin-8-yl)ethan-1-one):

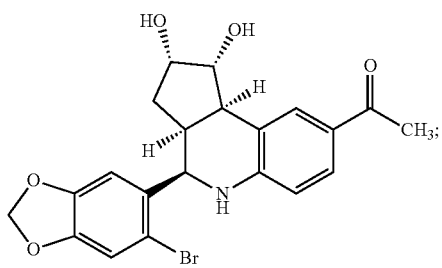 [SMILES: CC(=O)c1ccc2c(c1)[C@@H]1[C@@H](O)[C@@H](O)C[C@@H]1[C@H](c1cc3c(cc1Br)OCO3)N2]

CMPD11 (rel-1-((3aS,4R,9bR)-4-(2-bromo-4,5-dimethoxyphenyl)-2,3,3a,4,5,9b-hexahydro-1H-cyclopenta[c]quinolin-8-yl)ethan-1-one):

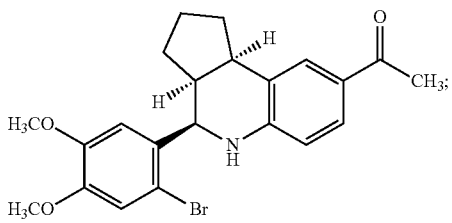 [SMILES: COc1cc(Br)c([C@@H]2Nc3ccc(C(C)=O)cc3[C@@H]3CCC[C@@H]32)cc1OC]

In certain embodiments, the compound of the invention, or a salt, solvate, tautomer, enantiomer or diastereoisomer thereof, is at least one compound of formula (II):

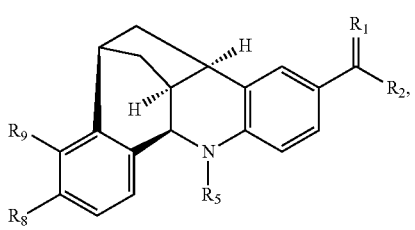

(II)

wherein:
$R_1$ is selected from the group consisting of =O and =N—OH;
$R_2$ is $C_1$-$C_4$ alkyl;
$R_5$ is selected from the group consisting of H, benzyl and $C_1$-$C_4$ alkyl;
$R_8$ and $R_9$ are independently selected from the group consisting of H and $C_1$-$C_4$ alkoxy, or $R_8$ and $R_9$ combine to form a diradical selected from the group consisting of —OCH$_2$O—, —OCH(CH$_3$)O— and —OC(CH$_3$)$_2$O—.

In certain embodiments, the compound of formula (II) is CMPD12 (rel-1-44S,5aS,6R,11aR)-4,5,5a,6,11,11a-hexahydro-4,6-methano[1,3] dioxolo[4',5':5,6]benzo[1,2-c]acridin-8-yl)ethan-1-one):

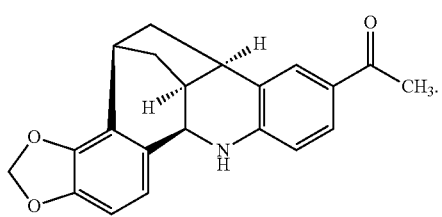 [SMILES: CC(=O)c1ccc2c(c1)[C@@H]1C[C@H]3C[C@@H]1[C@@H](N2)c1ccc2c(c13)OCO2]

In certain embodiments, the compound useful within the methods of the invention, or a salt, solvate, enantiomer or diastereoisomer thereof, is at least one GPER agonist recited in U.S. Patent Application Publications No. US 2008/0167334 and US 2011/0092533, all of which are incorporated herein in their entireties by reference:

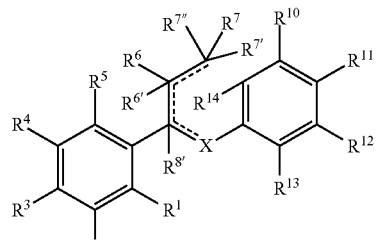

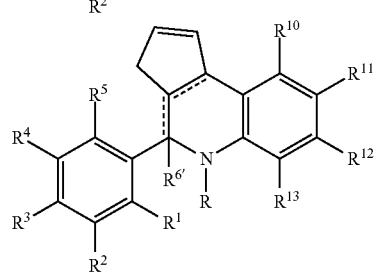

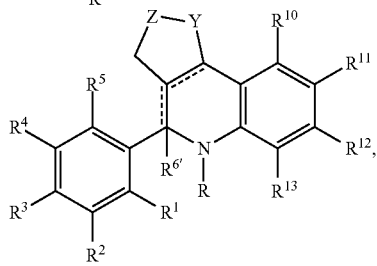

wherein:
X is =N—, O, S, or N—R, with the proviso that when X is N—R and R is a bond, N together with R' forms a 5- to 7-membered optionally substituted heterocyclic group;
R is a bond, H, —OH, —NO$_2$, optionally substituted $C_1$-$C_6$ hydrocarbyl (such as optionally substituted alkyl), optionally substituted aryl, optionally substituted heteroaryl, optionally substituted heterocycle, optionally substituted —C(O)—(C$_1$-C$_6$) alkyl (amide), optionally substituted —C(O)—O—(C$_1$-C$_6$) alkyl (urethane), optionally substituted —C(O)—NH(C$_1$-C$_6$) alkyl (urea), optionally substituted —C(O)—N(C$_1$-C$_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheterocycle);
$R^1$, $R^2$ and $R^5$ are each independently selected from H, —OH, —NO$_2$, halogen, $C_1$-$C_6$ optionally substituted carboxylic acid group, optionally substituted O—(C$_1$-C$_6$)alkyl, optionally substituted $C_1$-$C_6$ hydrocarbyl, optionally substituted aryl, optionally substituted heteroaryl, optionally substituted heterocycle, optionally substituted —C(O)—(C$_1$-C$_6$) alkyl (ketone), optionally substituted —C(O)—O—(C$_1$-C$_6$) alkyl (ester), optionally substituted O—C(O)—(C$_1$-C$_6$) alkyl (ester), optionally substituted —C(O)—NH(C$_1$-C$_6$) alkyl (urea), optionally substituted —C(O)—N(C$_1$-C$_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheterocycle);

$R^3$ and $R^4$ are each independently selected from H, —OH, —NO$_2$, halogen, $C_1$-$C_6$ optionally substituted carboxylic acid group, optionally substituted O—($C_1$-$C_6$)alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheteroaryl) or $R^3$ and $R^4$ together form a 5- or 6-membered optionally substituted carbocyclic (which may be saturated or unsaturated), optionally substituted aryl, optionally substituted heteroaryl or optionally substituted heterocyclic group;

$R^6$ and $R^7$ are each independently absent or are selected from H, —OH, —NO$_2$, halogen, $C_1$-$C_6$ optionally substituted carboxylic acid group, optionally substituted O—($C_1$-$C_6$)alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheteroaryl), or together $R^6$ and $R^7$ form a 4-, 5-, 6- or 7-membered optionally substituted carbocyclic (which may be saturated or unsaturated), optionally substituted aryl, optionally substituted heteroaryl or optionally substituted heterocyclic group, or a 5- to 9-membered optionally substituted carbocyclic or heterocyclic bicyclic group, with the proviso that $R^7$ is not absent when both $R^{7'}$ and $R^{7''}$ are also absent;

$R^{6'}$ is absent, H, $C_1$-$C_6$ optionally substituted hydrocarbyl group (such as H, CH$_3$ or CH$_2$CH$_3$) or together with $R^6$ forms =O;

$R^{7'}$ is absent, H, optionally substituted hydrocarbyl group (such as H, CH$_3$ or CH$_2$CH$_3$), or together with $R^7$ forms =O;

$R^{7''}$ is absent, H, —OH, halogen, optionally substituted O—($C_1$-$C_6$)alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheteroaryl);

$R^{8'}$ is absent (when the carbon to which $R^{8'}$ is attached and the carbon to which $R^6$ is attached form an optional double bond), H, CH$_3$ or CH$_2$CH$_3$;

$R^{10}$, $R^{11}$, $R^{12}$ and $R^{13}$ are each independently H, —OH, —NO$_2$, halogen, $C_1$-$C_6$ optionally substituted carboxylic acid group, optionally substituted O—($C_1$-$C_6$)alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheteroaryl);

$R^{14}$ is H, —OH, —NO$_2$, halogen, $C_1$-$C_6$ optionally substituted carboxylic acid group, optionally substituted O—($C_1$-$C_6$)alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheterocycle) or together with the carbon to which $R^7$ is attached forms a 5-, 6- or 7-membered optionally substituted carbocyclic (which may be saturated or unsaturated), optionally substituted aryl, optionally substituted heteroaryl or optionally substituted heterocyclic ring;

Y is optionally substituted (CH$_2$)$_n$ group where n is 0, 1 or 2, optionally substituted =CH— group, a C=O group, O, S, optionally substituted N—($C_1$-$C_6$)alkyl, optionally substituted N-aryl, optionally substituted N-heteroaryl, optionally substituted N-heterocycle, optionally substituted N—C(O)—($C_1$-$C_6$)alkyl, optionally substituted N—C(O)-aryl, optionally substituted N—C(O)-heteroaryl, optionally substituted N—C(O)-heterocycle;

Z is optionally substituted (CH$_2$)$_n$ group where n is 1 or 2, optionally substituted =CH— group, a C=O group, O, S, optionally substituted N—($C_1$-$C_6$)alkyl, optionally substituted N-aryl, optionally substituted N-heteroaryl, optionally substituted N-heterocycle, optionally substituted N—C(O)—($C_1$-$C_6$)alkyl, optionally substituted N—C(O)-aryl, optionally substituted N—C(O)-heteroaryl, optionally substituted N—C(O)-heterocycle.

In certain embodiments, the compound of the invention, or a salt, solvate, enantiomer or diastereoisomer thereof, is at least one GPER agonist recited in PCT Patent Application No. WO 2016/014847, which is incorporated herein in its entirety by reference:

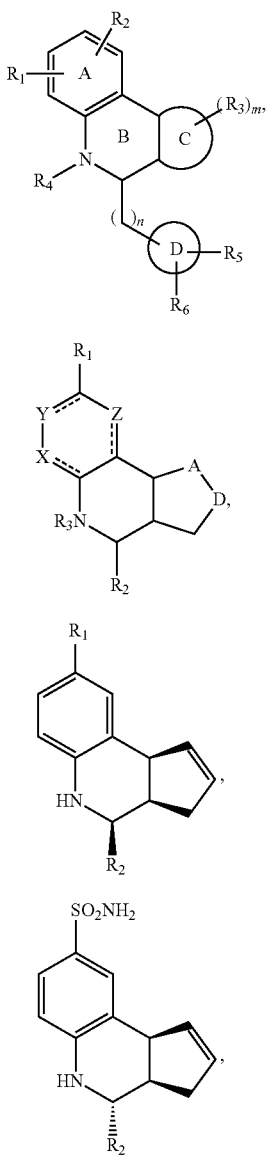

wherein in (i)-(iv):

Ring A is an aromatic or heteroaromatic five or six membered ring containing one or more heteroatom such as N, O, or S;

$R_1$ is independently selected from $SO_2NH_2$, $SO_2NR_aR_b$, COOH, $CONH_2$ and $CONR_aR_b$, and H. In $R_1$, each occurrence of $R_a$ and $R_b$ is independently selected from H, alkyl ($C_1$-$C_6$), alkenyl ($C_2$-$C_6$), alkynyl ($C_2$-$C_6$), alkoxy ($C_2$-$C_6$), cycloalkyl ($C_3$-$C_7$), alkylthio, alkylaryl, and aromatic and hetroaromatic rings. The aromatic and heteroaromatic rings can be further substituted with electron withdrawing and donating groups. $R_a$ and $R_b$ can form a cyclic ring ($C_3$-$C_7$) or an aromatic ring optionally containing one or more heteroatoms. Such aromatic rings can be further substituted with electron withdrawing groups such as halogens, —COOH, —CN, —$NO_2$ and the like, or electron donating groups such as alkyl groups;

$R_2$ is H, halogen, or a heteroatom such as N, O, or S;

Ring A is an aromatic or heteroaromatic ring (5 or 6 membered);

Ring B is a six membered saturated or aromatic ring containing N at the indicated position. The nitrogen of ring B optionally can be substituted with an alkyl, aryl, or alkaryl substituent;

Ring C is an independently a substituted or unsubstituted carbocyclic ring, bicyclic ring, aromatic ring, fused aromatic rings, or a heteroaromatic ring. Additionally, when it is a carbocyclic ring, it may contain one or more double bonds and one or more heteroatoms such as N, O, or S. It may also have an α-β unsaturated ketone function;

$R_3$ is selected independently from H, halogen, —OH, CN, ($C_1$-$C_6$) alkyl, ($C_2$-$C_6$) alkenyl, ($C_2$-$C_6$) alkynyl, ($C_1$-$C_6$) alkoxy, ($C_3$-$C_7$) cycloalkyl, ($C_1$-$C_6$) alkylthio, $NR_aR_b$, $R_aR_b$ or haloalkyl (e.g., $CF_3$). In $R_3$, each occurrence of $R_a$ and $R_b$ is independently hydrogen or ($C_1$-$C_6$) alkyl, or $R_a$ and $R_b$ form a saturated or unsaturated heterocyclic ring containing from 3-7 ring atoms, which ring may optionally contain another heteroatom selected from N, O, and S, and may be optionally substituted by from 1-3 groups which may be the same or different and are selected from ($C_1$-$C_4$) alkyl, phenyl, and benzyl; and m is 1-4;

Rings B and C are in certain embodiments cis fused;

Rings D and B is directly connected or connected through a spacer ($C_1$-$C_2$). When connected directly, they can be cis or trans with respect to the fusion of Ring B and C. Ring D is an aromatic or heteroaromatic ring containing one or more heteroatoms such as N, O, or S. It can be optionally substituted with $R_5$ and $R_6$ groups selected independently, or with —$R_6R_5$ or $R_5R_6$;

$R_5$ is independently selected from H, halogen, electron donating groups, and electron withdrawing groups such as alkyl, haloalkyl, alkoxy, —$NO_2$, —$SF_5$, —CN, and the like;

$R_6$ can be $NHC(O)OR_c$, $OC(O)NHR_c$, $C(O)O(CH_2)_nR_c$, $OC(O)(CH_2)_nR_c$, $C(O)NHR_c$, or $NHC(O)R_c$, where n=0-4; or $R_6$ can be alkyl, branched alkyl ($C_1$-$C_{10}$), alkynyl ($C_1$-$C_{10}$), a carbocyclic ring, alkenyl ($C_1$-$C_{10}$), halogen, CN, COOH, $CONH_2$, —OH, or $NH_2$. It, is alkyl, branched alkyl ($C_1$-$C_{10}$), alkoxy, alkylamino, acyl, alkynyl ($C_1$-$C_8$) or alkenyl ($C_1$-$C_6$). $R_6$ can also be $X(CH_2)_n$-E, wherein X is NH, O, S, C≡C, or HC=CH, and n=0-2, and E is independently a substituted or unsubstituted carbocyclic ring, bicyclic ring, aromatic ring, fused aromatic rings or heteroaromatic ring;

in certain embodiments, $R_1$ is selected from the group consisting of carboxyl, carboxamide, carboxyalkyl, carboxyaryl, cyano, nitro, hydroxyl, sulfonyl, sulfonamide, alkylsulfonamide, arylsulfonamide, alkylsulfonyl, aralkylsulfonamide, trifluoromethylsulfonamide, trifluoromethylsulfonyl carboxamide, and sulfonylcarbamide. In certain embodiments, $R_1$ is sulfonamide, alkylsulfonamide, or arylsulfonamide. $R_2$ can be a 3-, 4-, 5-, or 6-membered saturated or aromatic carbon ring or ring system optionally containing one or two heteroatoms selected from N, O, and S, the ring or ring system optionally substituted with one or more substituents selected from the group consisting of cyano, halo, acyl, acyloxy, alkyl, alkoxy, heteroalkyl, alkylester, alkylamido, alkylamino, aryl, aryloxy, arylalkyl, arylester, azido, alkylhalo, alkenyl, alkynyl, alkyl ether, nitro, thiohalo, and thiocyano. $R_3$ can be H, or a $C_1$-$C_5$ alkyl or cycloalkyl group optionally substituted with one or more of cyano, nitro, and one or more aromatic or heteroaromatic groups containing N, O, or S. A and D can be independently selected from CH, $CH_2$, N, and O, and the bond joining them is a single or double bond as appropriate for the selected atoms. X, Y, and Z are independently selected from no atom (i.e., they are absent), CH, C-halogen, N, O, and S;

in certain embodiments, $R_2$ is a substituent represented by —$R_dR_eR_f$ or by —$R_dCOR_eR_f$; wherein $R_d$, $R_e$, and $R_f$ are independently selected from a 3-, 4-, 5-, or 6-membered saturated or aromatic carbon ring or ring system optionally containing one or two heteroatoms selected from N, O, and S, the ring or ring system optionally substituted with one or more substituents selected from the group consisting of cyano, halo, acyl, acyloxy, alkyl, alkoxy, heteroalkyl, alkylester, alkylamido, alkylamino, aryl, aryloxy, arylalkyl, arylester, azido, alkylhalo, alkenyl, alkynyl, alkyl ether, nitro, thiohalo, and thiocyano;

Compounds of the invention may be prepared according to methods described herein, methods known in the art, and/or methods described in certain references, such as but not limited to: PCT Application Publications No. WO 2004/072046 and No. WO 2016/014847; U.S. application Ser. No. 10/511,083; U.S. Patent Application Publications No. US 2008/0167334 and US 2011/0092533; and Burai, et al., 2010, Org. & Biomol. Chem. 8:2252-2259; all of which are included herein in their entireties by reference.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

In certain embodiments, the invention further provides pharmaceutical compositions comprising at least one compound of the invention and at least one pharmaceutically acceptable carrier. In other embodiments, the pharmaceutical composition is formulated for inhalational, oral, rectal, vaginal, parenteral, topical, transdermal, pulmonary, intranasal, buccal, ophthalmic, intrathecal, intracranial, or intravenous administration. Each and every formulation of the compounds contemplated within the invention may be used for treating or preventing a GPCR-expressing (such as a GPER-expressing) and/or Myc-expressing cancer, such as but not limited to melanoma.

In certain embodiments, the pharmaceutical compositions of the invention comprise at least one additional anticancer agent and at least one compound of the invention. Examples of additional anticancer agents include, but are not limited to, chemotherapy, and immune checkpoint inihibitors. Non-limiting examples of chemotherapy include, but are not limited to, a HDAC, temozolomide, dacarbazine (DTIC), vemurafenib, dabrafenib and trametinib. Non-limiting examples of checkpoint inhibitors include, but are not limited to, PD-1 inhibitors (i.e. Pembrolizumab, Nivolumab, anti-PD-1), PD-L1 inhibitors (i.e. Atezolizumab, anti-PD-L1), CTLA-4 inhibitors (i.e. Ipilimumab, anti-B7-1/B7-2, anti-CTLA-4), Indoleamine (2,3)-dioxygenase (IDO1/2) inhibitors, B7 homolog 3 (B7-H3) inhibitors, lymphocyte activation gene 3 (LAG3) inhibitors, and TIGIT (T cell immunoreceptor with Ig and ITIM domains) targeting antibodies and agents.

The present invention also pertains to kits useful within any of the methods of the invention described herein. Such kits comprise components useful in any of the methods described herein, including for example, compositions and methods for treating or preventing a GPCR-expressing (such as a GPER-expressing) and/or Myc-expressing cancer, such as but not limited to melanoma in a subject, such as a human, one or more containers (e.g., test tube, cell culture dish, cell culture plate, cell culture flask, cell culture bag) for containing a component of any of the embodiments of the invention described elsewhere herein, and instructional materials.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Methods

The invention provides a method of treating or preventing a GPCR-expressing (such as a GPER-expressing) and/or Myc-expressing cancer, such as but not limited to melanoma, pancreatic cancer, and/or lung cancer (such as but not limited to non-small cell lung cancer), in a subject. In certain embodiments, the method comprises administering to the subject in need thereof a therapeutically effective amount of estrogen and/or a GPCR agonist that increases tumor cell differentiation, whereby the GPCR-expressing (such as a GPER-expressing) and/or Myc-expressing cancer is treated or prevented in the subject.

In certain embodiments, the GPCR is GPER. In other embodiments, the GPER agonist comprises G-1. In certain embodiments, the GPER agonist is selected from the group consisting of estradiol (E2), tamoxifen, fulvestrant, and raloxifene (also known as 6-hydroxy-2-(4-hydroxyphenyl)-benzothiophen-3-yl]-[4-[2-(1-piperidyl)ethoxy]phenyl]-methanone). In certain embodiments, the estrogen is any substance, natural or synthetic, that mimics the effect of the natural hormone, estrogen. Examples of estrogen contemplated within the invention include, but are not limited to, estrone (E1), estradiol (E2), estriol (E3), estetrol (E4), 17β-estradiol, 27-hydroxycholesterol, dehydroepiandrosterone (DHEA), 7-oxo-DHEA, 7α-hydroxy-DHEA, 16α-hydroxy-DHEA, 7β-hydroxyepiandrosterone, $\Delta^4$-androstenedione, $\Delta^5$-androstenediol, 3α-androstanediol, 3β-androstanediol, 2-hydroxyestradiol, 16-hydroxyestrone, estradiol cypionate, estradiol valerate, estradiol acetate, estradiol benzoate, ethinyl estradiol (EE), mestranol, moxestrol, quinestrol, diethylstilbestrol benzestrol, dienestrol, dienestrol acetate, diethylstilbestrol dipropionate, fosfestrol, hexestrol, methestrol dipropionate, xenoestrogens, phytoestrogens, and/or mycoestrogens.

In certain embodiments, the estrogen and/or GPCR agonist is administered to the subject as a pharmaceutical composition further comprising at least one pharmaceutically acceptable carrier.

In certain embodiments, the subject is further administered at least one anticancer treatment. Examples of anticancer treatments include, but are not limited to, chemotherapy, radiation, surgery, and/or immune checkpoint inhibitors. Examples of chemotherapy include, but are not limited to, a HDAC, temozolomide, dacarbazine (DTIC), vemurafenib, dabrafenib and trametinib. Examples of immune checkpoint inhibitors include, but are not limited to, PD-1 inhibitors (i.e. Pembrolizumab, Nivolumab, anti-PD-1), PD-L1 inhibitors (i.e. Atezolizumab, anti-PD-L1), CTLA-4 inhibitors (i.e. Ipilimumab, anti-B7-1/B7-2, anti-CTLA-4), Indoleamine (2,3)-dioxygenase (IDO1/2) inhibitors, B7 homolog 3 (B7-H3) inhibitors, lymphocyte activation gene 3 (LAG3) inhibitors, and TIGIT (T cell immunoreceptor with Ig and ITIM domains) targeting antibodies and agents. In other embodiments, the chemotherapy or immune checkpoint inhibitor is co-administered or co-formulated with the estrogen or GPCR agonist.

In certain embodiments, the estrogen or GPCR agonist is administered to the subject by an inhalational, oral, rectal, vaginal, parenteral, topical, transdermal, pulmonary, intranasal, buccal, ophthalmic, intrathecal, intracranial, or intravenous route of administration. In other embodiments, the estrogen or GPCR agonist is the only anticancer agent administered to the subject. In yet other embodiments, the estrogen or GPCR agonist is the only anticancer agent administered to the subject in an amount sufficient to treat or prevent the cancer in the subject.

In certain embodiments, the cancer is breast cancer. In other embodiments, the cancer is not breast cancer. In yet other embodiments, the cancer is ovarian cancer. In yet other embodiments, the cancer is not ovarian cancer. In yet other embodiments, the cancer is prostate cancer. In yet other embodiments, the cancer is not prostate cancer. In yet other embodiments, the cancer is castration-resistant prostate cancer (CRPC). In yet other embodiments, the cancer is not CRPC. In yet other embodiments, the cancer is endometrial cancer. In yet other embodiments, the cancer is not endometrial cancer. In yet other embodiments, the subject is a mammal. In yet other embodiments, the mammal is human.

The invention further provides a method of selecting a patient suffering from cancer who will benefit from treatment with estrogen and/or a GPCR agonist (such as a selective GPCR agonist). The method comprises obtaining a sample from the subject's cancer and determining if at least one cancer cell from the sample expresses GPER and/or another GPCR. The detection and/or quantitation of GPER and/or another GPCR in the sample can be done using any of the methods described herein, or any methods known in the art. In certain embodiments, if the cancer cell expresses GPER and/or another GPCR, then the subject is counseled to receive cancer treatment comprising estrogen and/or a selective GPER agonist and/or another GPCR agonist, optionally in combination with at least one immunotherapeutic agent and/or HDAC inhibitor. In other embodiments, if the cancer cell expresses GPER and/or another GPCR, then the subject is administered cancer treatment comprising estrogen and/or a selective GPER agonist and/or another GPCR agonist, optionally in combination with at least one immunotherapeutic agent and/or HDAC inhibitor. In other embodiments, if the cancer cell does not express GPER and/or another GPCR, the subject is counseled not to receive cancer treatment comprising estrogen and/or a selective GPER agonist and/or another GPCR agonist, optionally in combination with at least one immunotherapeutic agent and/or HDAC inhibitor. In yet other embodiments, if the cancer cell does not express GPER, the subject is not administered cancer treatment comprising estrogen and/or a selective GPER agonist and/or another GPCR agonist, optionally in combination with at least one immunotherapeutic agent and/or HDAC inhibitor.

Formulations/Administration

The relative amounts of the active ingredient, the pharmaceutically acceptable carrier, and any additional ingredients in a pharmaceutical composition of the invention will vary, depending upon the identity, size, and condition of the subject treated. By way of example, the composition may comprise between about 0.005% and about 100% (w/w) of the active agent, or any fractions or multiples thereof.

In certain embodiments, the pharmaceutical compositions useful for practicing the method of the invention may be administered to deliver a dose of between 1 ng/kg/day and 100 mg/kg/day, such as for example 1-50 mg/kg/day. In other embodiments, the pharmaceutical compositions useful for practicing the invention may be administered to deliver a dose of between 1 ng/kg/day and 1,000 mg/kg/day.

The composition comprising a compound contemplated within the invention can be administered to a mammal as frequently as several times daily, or it may be administered less frequently, such as once a day, once a week, once every two weeks, once a month, or even less frequently, such as once every several months or even once a year or less.

It is understood that the amount of compound dosed per day may be administered, in non-limiting examples, every day, every other day, every 2 days, every 3 days, every 4 days, or every 5 days. For example, with every other day administration, a 0.5-5 mg per day dose may be initiated on Monday with a first subsequent 0.5-5 mg per day dose administered on Wednesday, a second subsequent 0.5-5 mg per day dose administered on Friday, and so on. The frequency of the dose will be readily apparent to the skilled artisan and will depend upon any number of factors, such as, but not limited to, the type and severity of the disease being treated, the type and age of the animal, and so forth.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions comprising a compound contemplated within the invention are formulated using one or more pharmaceutically acceptable excipients or carriers. In certain embodiments, the pharmaceutical compositions of the invention comprise a therapeutically effective amount of at least one compound contemplated within the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. In certain embodiments, the administration comprises topical administration. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Such formulations may be applied to the skin directly or through the use of swabs, applicators, spatulas and the like, as well as in the form of transdermal patches. In certain embodiments, the patch minimizes loss of pharmaceuticals through washing, friction, scratching and/or rubbing of the skin. In other embodiments, the patch increases absorption of the pharmaceutical through the skin, while minimizing the exposure of the skin to the pharmaceutical.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone. One acceptable vehicle for topical delivery of some of the compositions of the invention may contain liposomes. The composition of the liposomes and their use are known in the art (for example, U.S. Pat. No. 6,323,219).

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Controlled Release Formulations and Drug Delivery Systems

In certain other embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds useful within the methods of the invention may be administered in the form of microparticles, for example by injection, or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Estrogen and G-1 Treatment Slow Melanoma Cell Proliferation and Drive Differentiation In Vitro and In Vivo Tumor cell proliferation slowed in both mouse and human melanoma cells following treatment with estrogen or G-1, a specific GPER agonist. Mouse and human melanoma cell lines were treated in vitro with either estrogen (25 nM E2) (FIGS. 4A-4F), the GPER agonist G-1 (100 nM G1), or a delivery vehicle. Cell proliferation and differentiation (melanin production) were measured. Results showed that both estrogen and G-1 treatment slowed melanoma cell proliferation and drove differentiation in vitro (FIGS. 4A-4F).

Human and mouse melanoma cells treated with estrogen, or the specific GPER agonist G-1, grew more slowly in mice, and formed significantly smaller tumors (FIGS. 5-6). Mouse (B16) and human (WM46) cell lines were pretreated with estrogen, G-1, or vehicle in vitro for one week then injected in equal numbers in to the left (vehicle-treated) or right (E2-treated) flank of mice, inducing tumor formation (N=5 mice per group) (FIG. 5). 14-16 days later, mice were imaged and tumors were harvested and weighed. Pretreatment with estrogen inhibited tumor growth in vivo by approximately 3 fold (FIG. 5). Similarly, treatment with G-1 inhibited tumor growth in vivo (FIG. 6).

Transient estrogen exposure was sufficient to induce epigenetic memory that maintains the more differentiated state. Normal human melanocytes received a pulse-treatment of estrogen—this consisted of 4 days of estrogen treatment followed by an 8 day withdraw. RNAseq showed that melanocytes transiently treated with estrogen maintained upregulated expression of all the major melanocyte differentiation markers including tyrosinase (TYR), tyrosinase related protein (TRP1), melanocortin 1 receptor (MC1R), melan-A (MLANA), and dopachrome tautomerase (DCT), and decreased expression of aggressive melanoma markers such as premelanosome protein (PMEL) (FIG. 3). Changes in the amounts of melanocyte differentiation markers were even more apparent at the protein level. Estrogen treated cells also make more pigment, indicating they are more differentiated as compared to control (vehicle treated) cells (FIG. 3).

Example 2: Multiple Pregnancies Limit Melanomagenesis and Drives Differentiation Cell lines and subcutaneous tumors are regularly used for cancer studies because they are fast and easy, but they may not be physiologically-faithful models of real human disease. Described herein is an engineered human xenograft model that provides a better model of human melanoma.

Figure 7A:
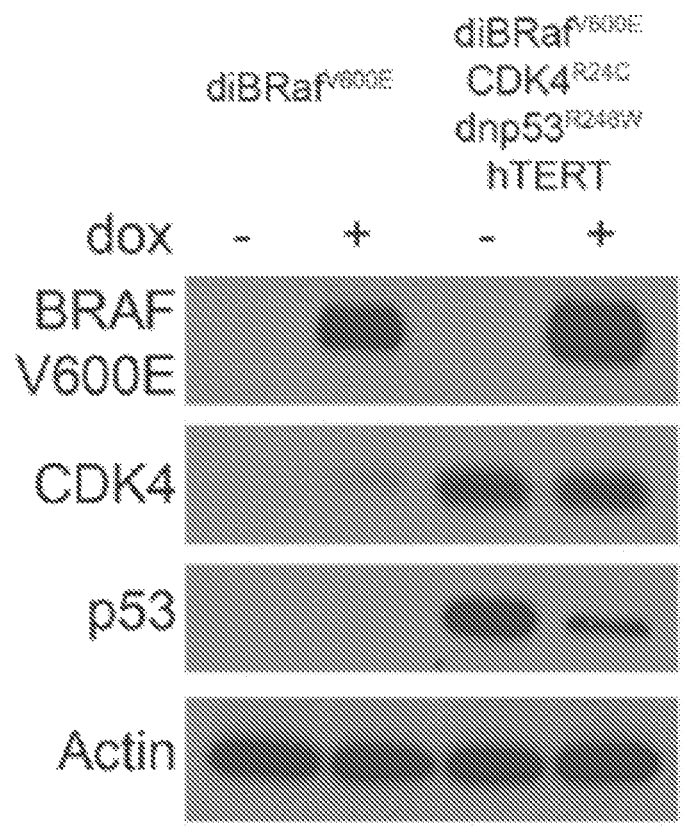
FIGS. 7A-7C illustrate the finding that multiple pregnancies inhibit melanomagenesis.
Figure 7B:
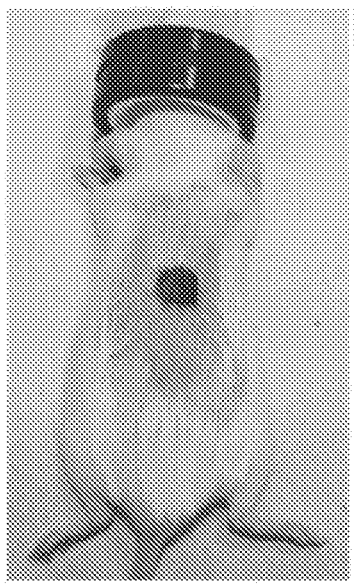
Figure 7C:
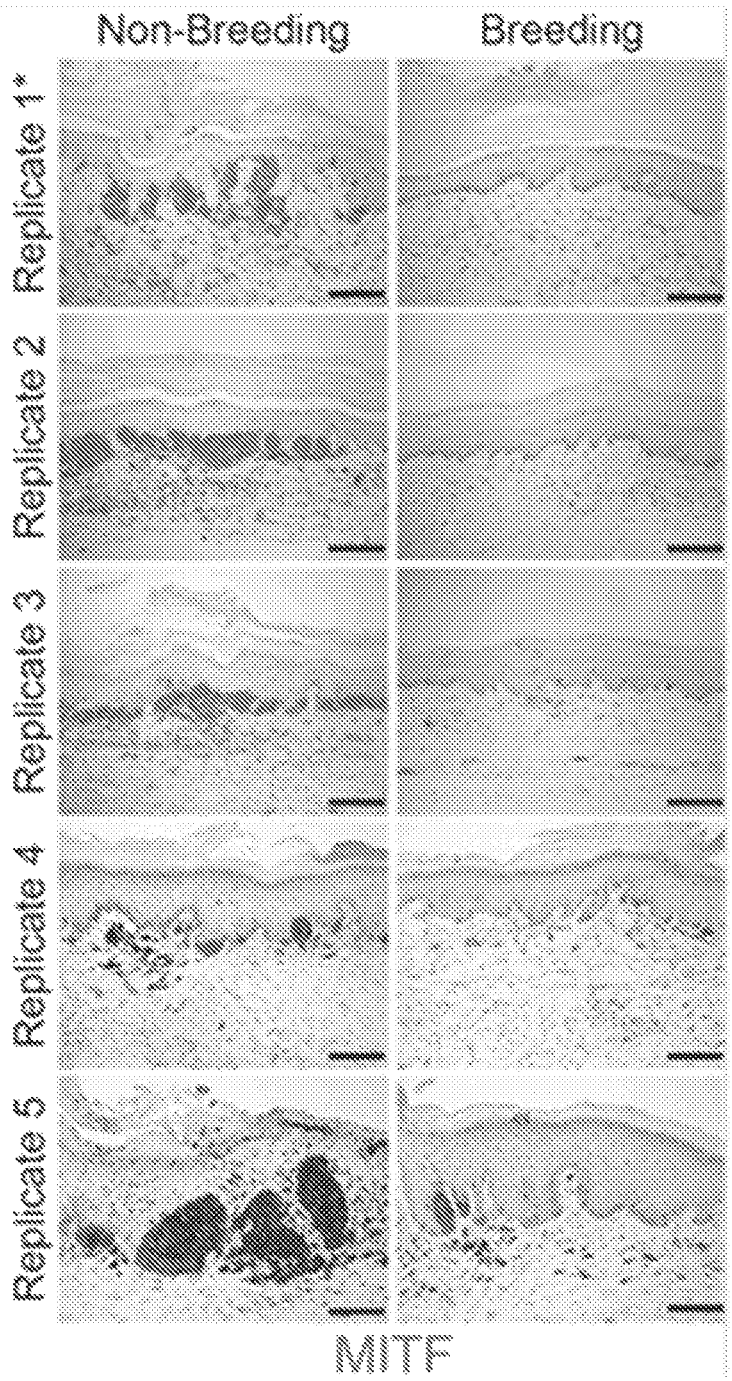

Human melanoma xenografts were engineered with lentiviruses to express mutant oncoproteins known to be associated with melanoma into normal human melanocytes. Primary melanocytes were transduced with diBRAf$^{V600E}$, cDK4$^{R24C}$, dnp53$^{R248W}$, and hTERT (FIG. 7A). Next, organotypic skin was established in vitro and then grafted onto the backs of female mice (FIG. 7B). The mice were split into two groups, non-breeding and breeding (N=3 mice per group), and the melanoma formed over the subsequent 15 weeks. The tissue was harvested and assayed for the mutated genes. In the non-breeding groups, large proliferative nests of melanocytes with upwards spread were observed, characteristic of radial growth phase melanoma (FIG. 7C)). Limited amounts of melanin was transferred to the epidermis indicating that the melanocytes were not performing their differentiated function anymore. In the breeding group, large proliferative nests were not observed, and an increase in the amount of melanin being transferred to the epidermis was seen, indicating that the melanocytes were performing their differentiated function better than the breeding controls. Together, this shows that multiple pregnancies (3 for this experiment) serves to limit melanomagenesis and drive differentiation.

Figure 8A:
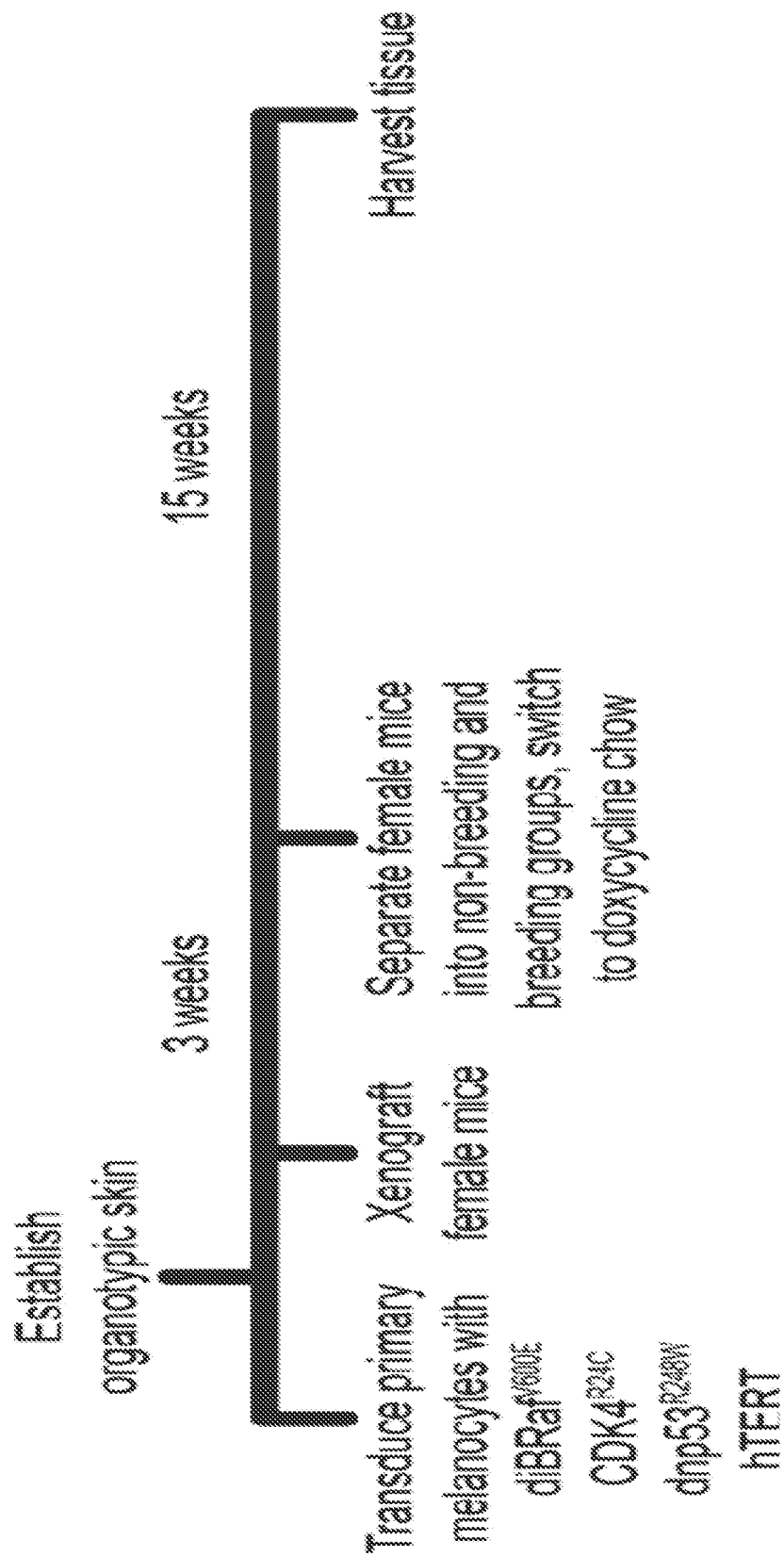
FIGS. 8A-8E illustrate the finding that multiple pregnancies inhibit melanomagenesis and drive differentiation.
Figure 8B:
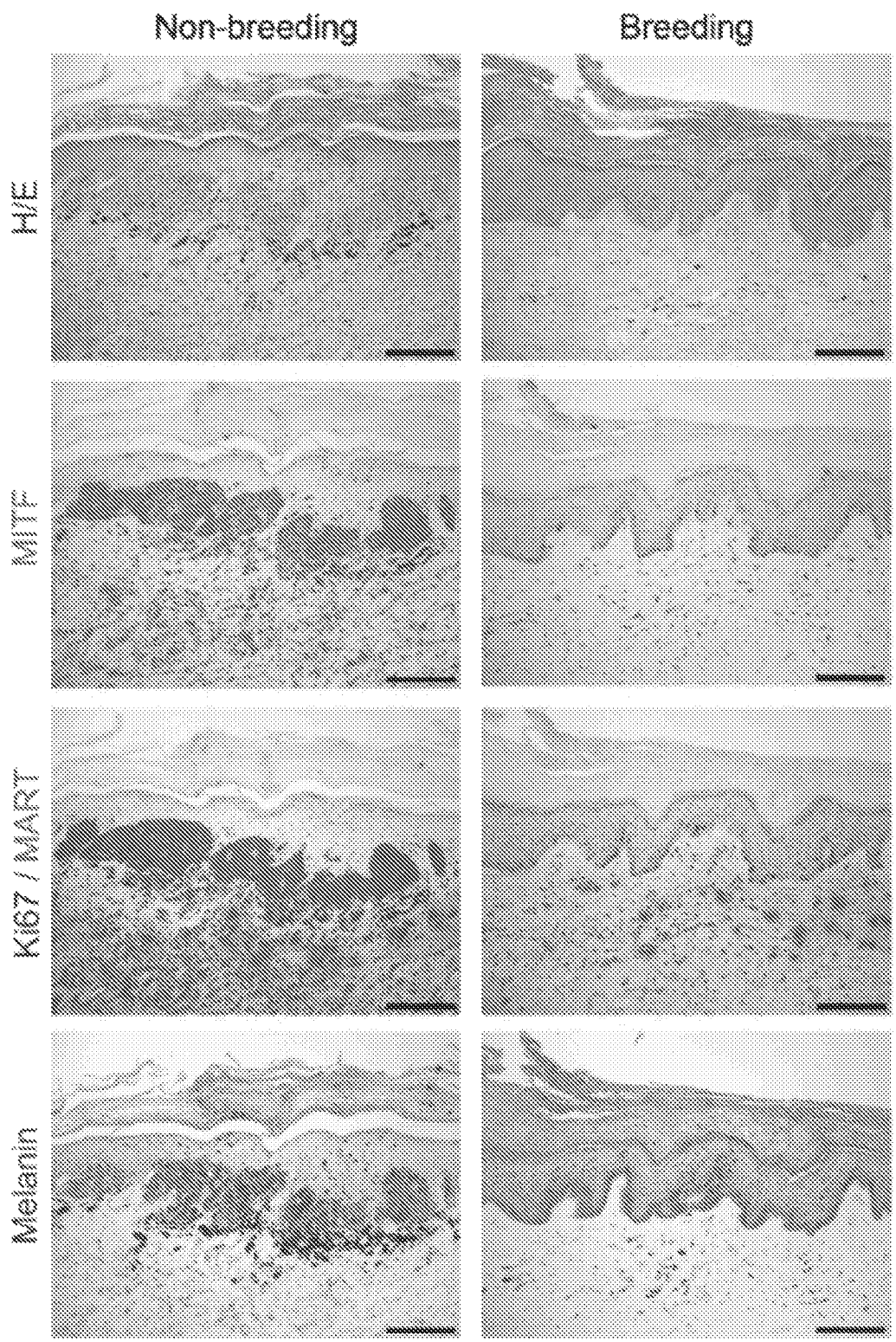
Figure 8C:
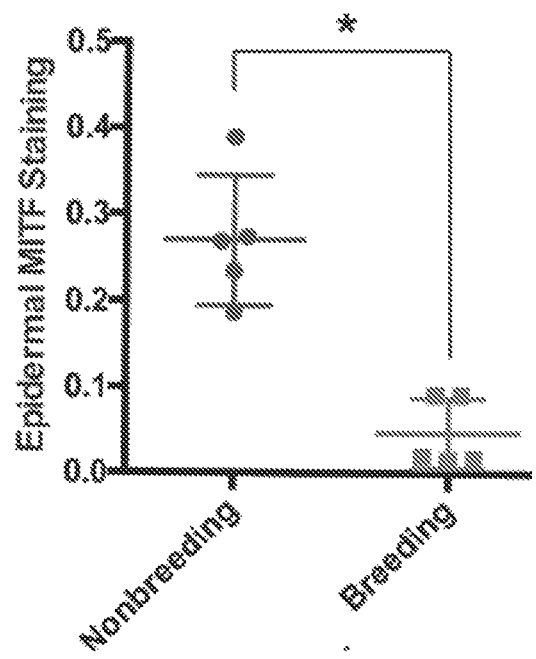
Figure 8D:
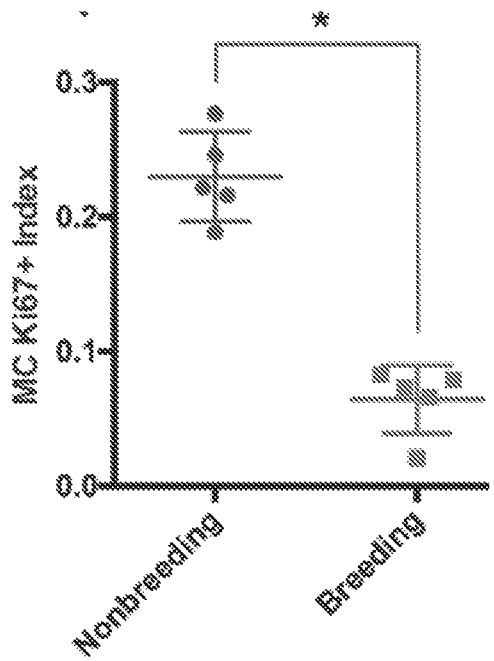

As shown in FIGS. 8A-8E, after grafts healed, mice were randomized and separated into nonbreeding or breeding groups, and doxycycline chow was then provided to induce the BRAF$^{V600E}$ oncogene in all animals. After 15 weeks and 3 consecutive pregnancies in the breeding group (or no pregnancies in the nonbreeding group), human tissues were harvested and analyzed histologically (FIG. 8A). Grafts from the nonbreeding group developed into melanocytic neoplasms with hallmark features of human melanoma including large, mitotically active melanocytic nests with cellular atypia. In contrast, tissues from the breeding group were relatively unremarkable and contained primarily quiescent, single, nonproliferating melanocytes that were confined to the basal epidermal layer. These results show that repeated pregnancies inhibit the growth of BRaf-driven human melanocytic neoplasia (FIGS. 8B-8D).

Figure 8E:
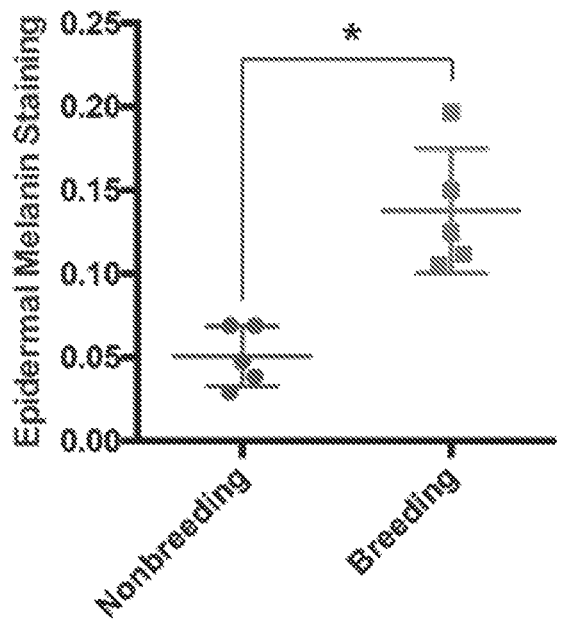

The primary role of a fully differentiated epidermal melanocyte is to produce melanin pigment that protects the skin from ultraviolent radiation. As with most cell types, melanocyte differentiation and proliferation are inversely correlated, and melanocytes in normal skin proliferate rarely outside of cycling hair follicles. Melanoma tissue is generally less differentiated than normal melanocytes or benign nevi. In the present xenograft studies, pregnancy was associated with an increase in melanocyte differentiation compared to the nonbreeding group, as evidenced by the relative lack of proliferating melanocytes and corresponding increase in epidermal melanin. Although the nonbreeding group, which developed melanomas, had significantly more melanocytes in the grafted skin than the breeding group, melanin abundance within the surrounding epidermal keratinocytes was dramatically reduced (FIG. 8E). Thus, pregnancy inhibits melanoma development by inducing melanocyte differentiation.

Figure 11A:
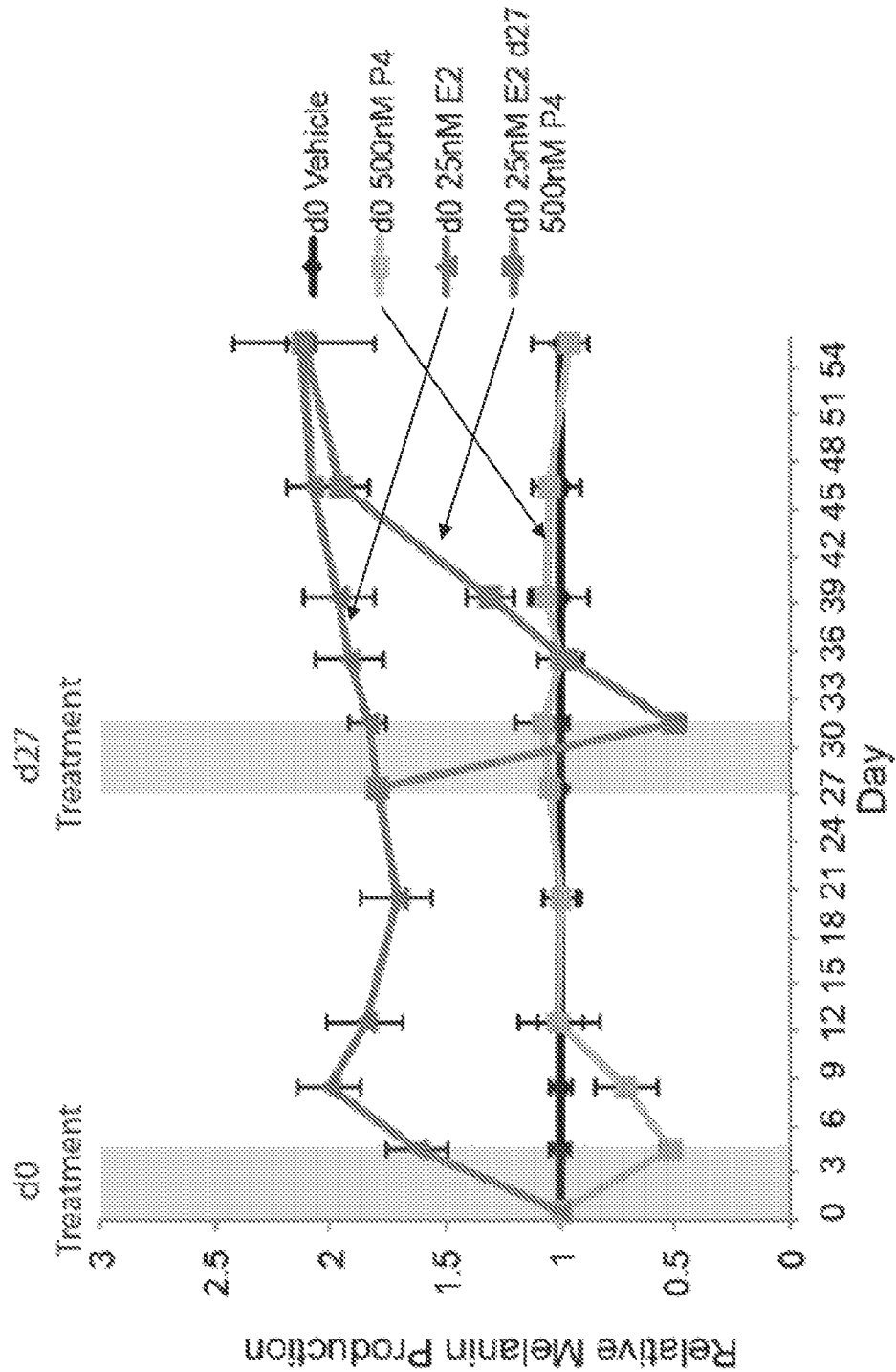
FIGS. 11A-11E illustrate the finding that GPER signaling drives stable differentiation in normal human melanocytes and in melanoma.

Example 3: GPER Signaling Drives Stable Differentiation in Normal Human Melanocytes and in Melanoma To test whether pregnancy-associated hormones induce long-lasting changes in melanocyte differentiation that may affect their future susceptibility to transformation, primary human melanocytes were transiently exposed to estrogen or progesterone (FIGS. 11A-11E). Estrogen drove differentiation, which was associated with increased melanin production, while progesterone had opposite effects (FIG. 11A).

Figure 11B:
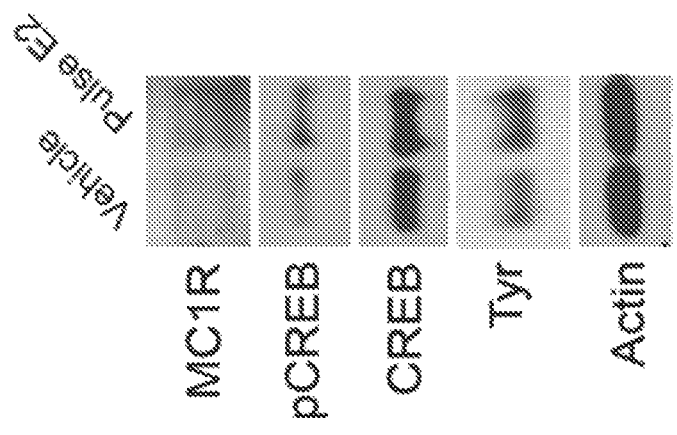

After hormone withdrawal, progesterone-treated cells quickly returned to their baseline level of melanin production. In contrast, estrogen-treated cells remained more differentiated after estrogen withdrawal and stably produced more melanin through continual cell divisions over the subsequent 50 days. A subset of cells differentiated by transient exposure to estrogen was subsequently treated with progesterone. This reversed the estrogen effects, and melanin production decreased to the sub-baseline level seen upon initial progesterone treatment. After progesterone withdrawal, these cells fully returned to the heightened differentiation state induced by the initial estrogen exposure. Consistent with increased cellular differentiation, estrogen exposure was associated with stable increases in classic melanocyte differentiation antigens, including tyrosinase and MC1R (FIG. 11B). These results indicate that transient estrogen induces a durable, long-lasting differentiation program in melanocytes.

Figure 11C:
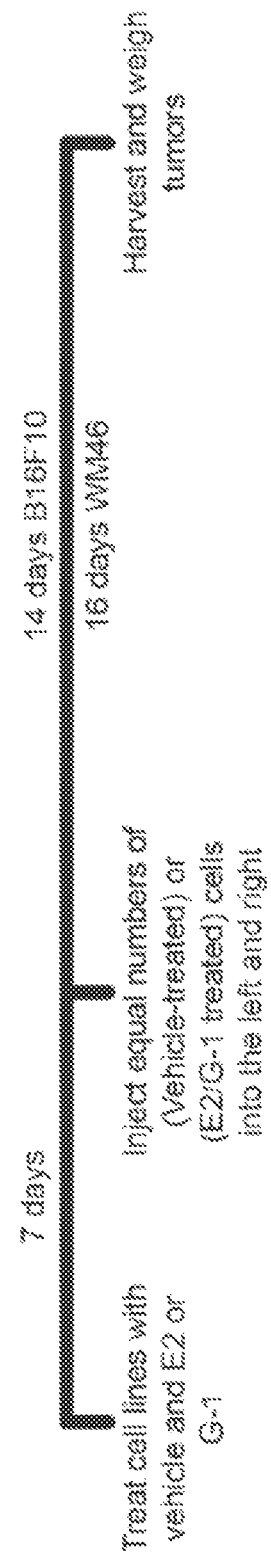
Figure 11D:
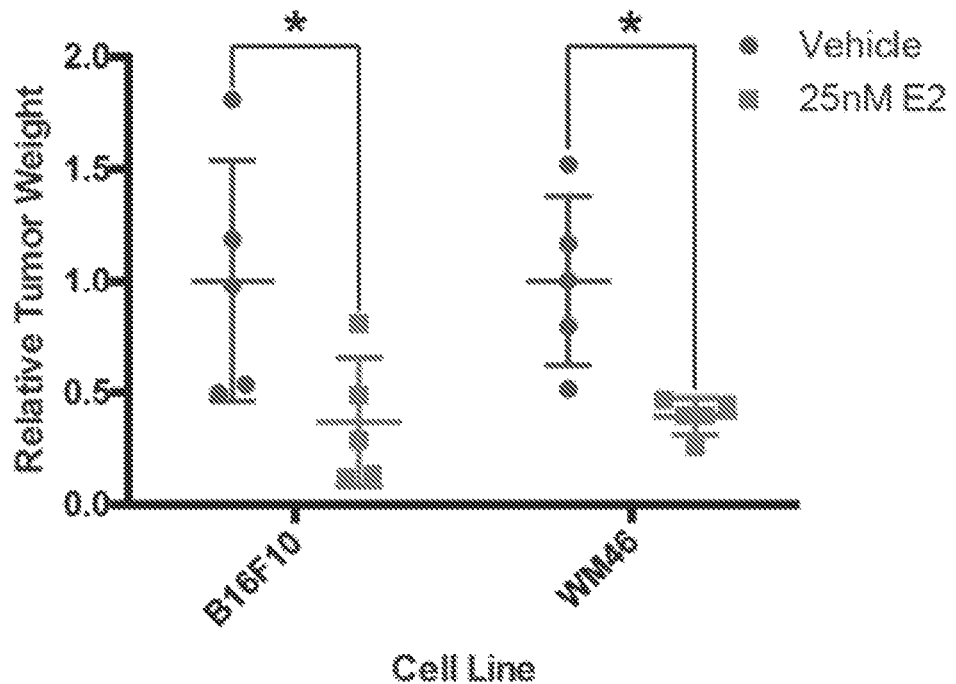
Figure 11E:
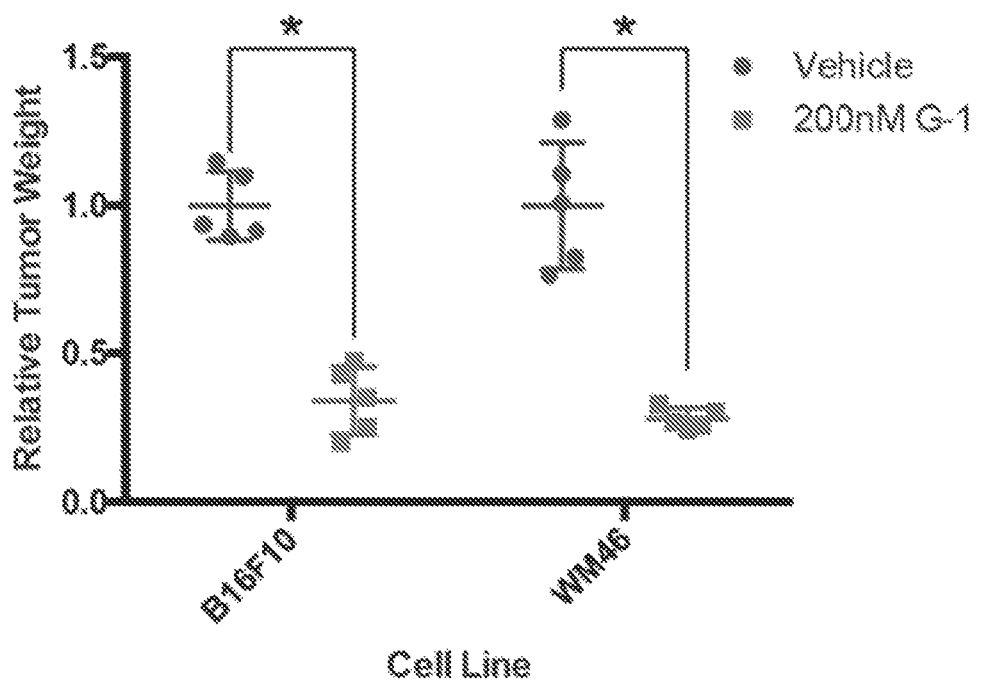

To test whether transient GPER signaling induces a persistent differentiation state in melanoma cells that affects subsequent tumor growth in vivo, melanoma cells were treated with estrogen, G-1, or vehicle in vitro, and subsequently injected equal numbers of treated cells into host mice (FIG. 11C). Pretreatment with estrogen or G-1 markedly reduced subsequent tumor size (FIGS. 11D-11E), indicating that transient GPER activation has durable effects on tumor growth.

Example 4: GPER Signaling Results in Loss of C-Myc in Melanoma

Amplification of c-Myc (a transcription factor that antagonizes differentiation and promotes proliferation, survival, and escape from immune surveillance) is one of the most common genetic alterations in human cancers, including melanoma. GPER signaling depleted c-Myc protein (FIG. 12, Panels A-C).

Figure 12:
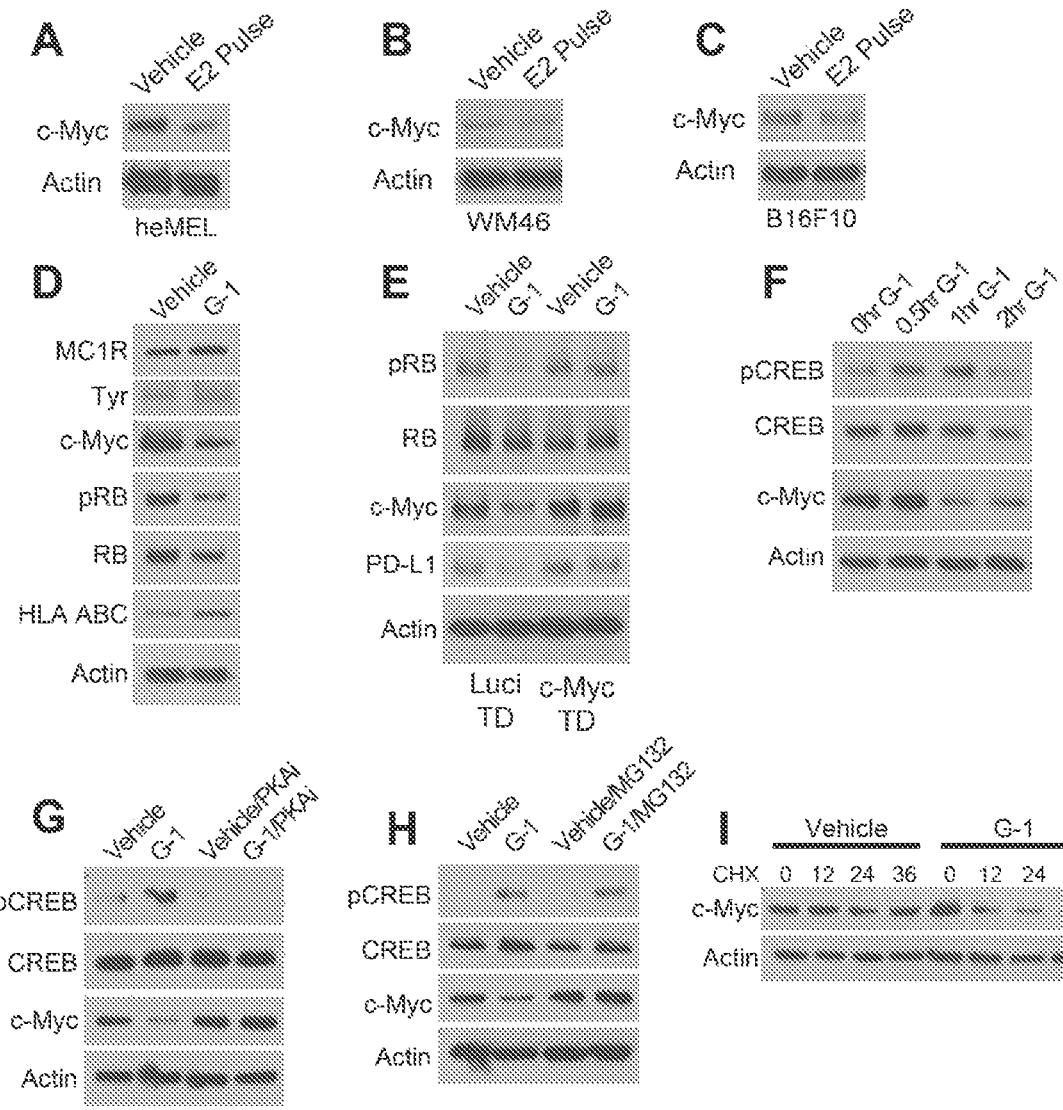
FIG. 12 illustrates the finding that GPER signaling results in loss of c-Myc in melanoma. Panels A-C: Western blots of heMel (Panel A), WM46 (Panel B), and B16F10 (Panel C) melanoma transiently treated with E2 for 3 days, followed by 4 day withdraw. Panel D: Western blot of WM46 cells treated with a specific GPER agonist (G-1) for 16 hours. Panel E: Western blot of luciferase- or c-Myc-transduced WM46 cells treated with G-1 for 16 hours. Panel F: Western blot of WM46 cells treated with G-1 across a time course. Panel G: Western blot of WM46 cells treated with G-1, 100 µM PKA inhibitor Rp-8-Br-cAMPS (PKAi), or both for 1 hour. Panel H: Western blot of WM46 cells treated with G-1, 2.504 proteasome inhibitor (MG132), or both for 1 hour. Panel I: Western blot of WM46 cells treated with 10 µg/ml cyclohexamide (CHX) with and without G-1.

Furthermore, GPER signaling induced a relative growth arrest, associated with hypophosphorylation of Rb in both mouse and human melanoma cells (FIG. 12, Panel D). Melanoma cells engineered to maintain c-Myc protein in the face of GPER activation were resistant to G-1, indicating that c-Myc loss is a major mediator of the antiproliferative GPER effects (FIG. 12, Panel E).

c-Myc loss following GPER activation was rapid and PKA dependent, suggesting that canonical stimulatory G protein-coupled receptor signaling destabilized c-Myc protein (FIG. 12, Panels F-G). Consistent with this, c-Myc half-life was markedly shortened after GPER activation, in a proteasome-dependent manner (FIG. 12, Panels H-I).

Example 5: G-1 Treatment In Vivo Alters Immunomodulatory Proteins

Figure 13A:
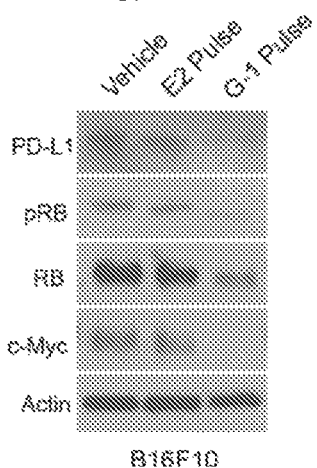
FIGS. 13A-13G illustrate the finding that transient GPER activation inhibits proliferation and augments response to immunotherapy in melanoma.
Figure 13B:
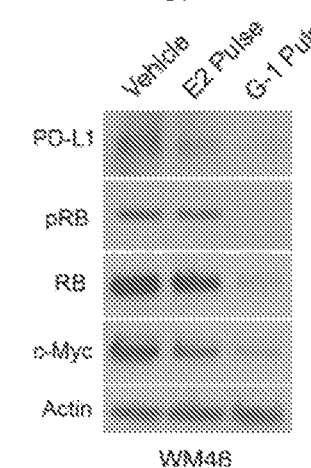
Figure 13C:
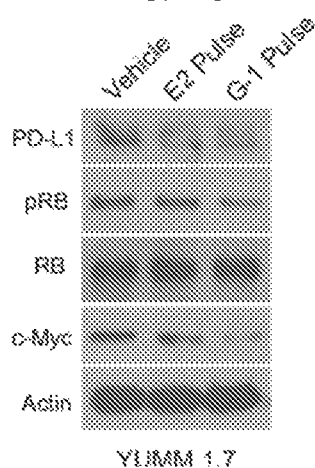
Figure 13D:
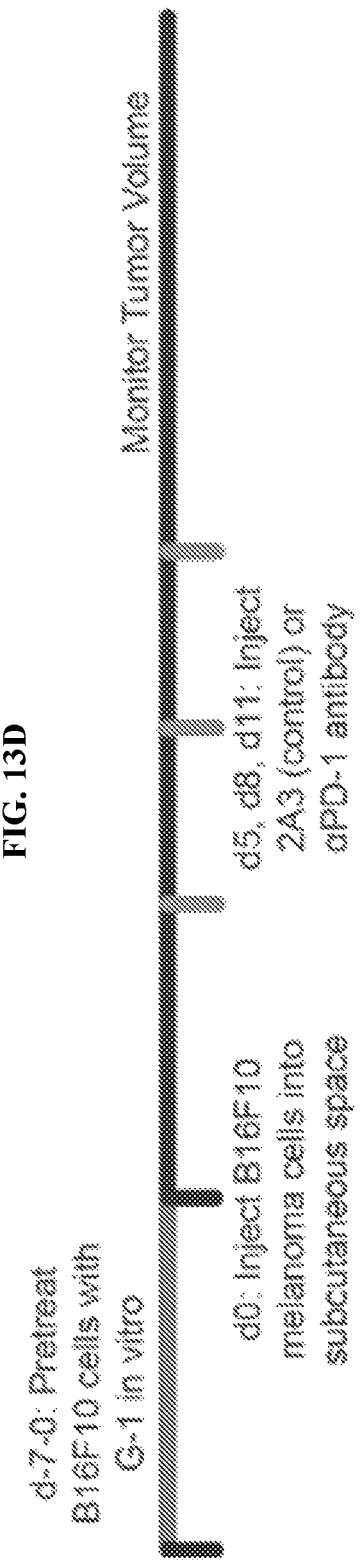
Figure 13E:
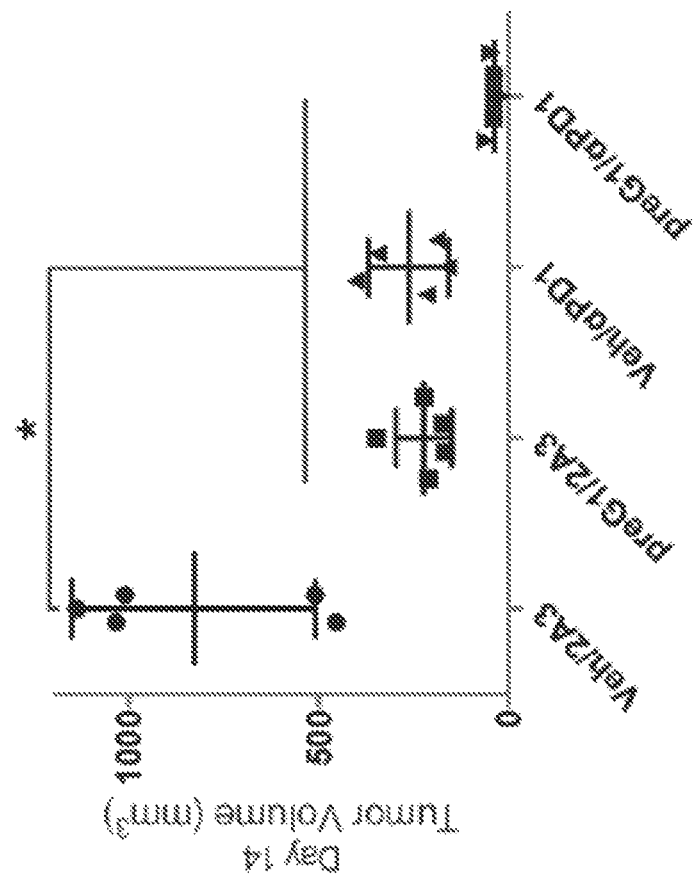
Figure 13F:
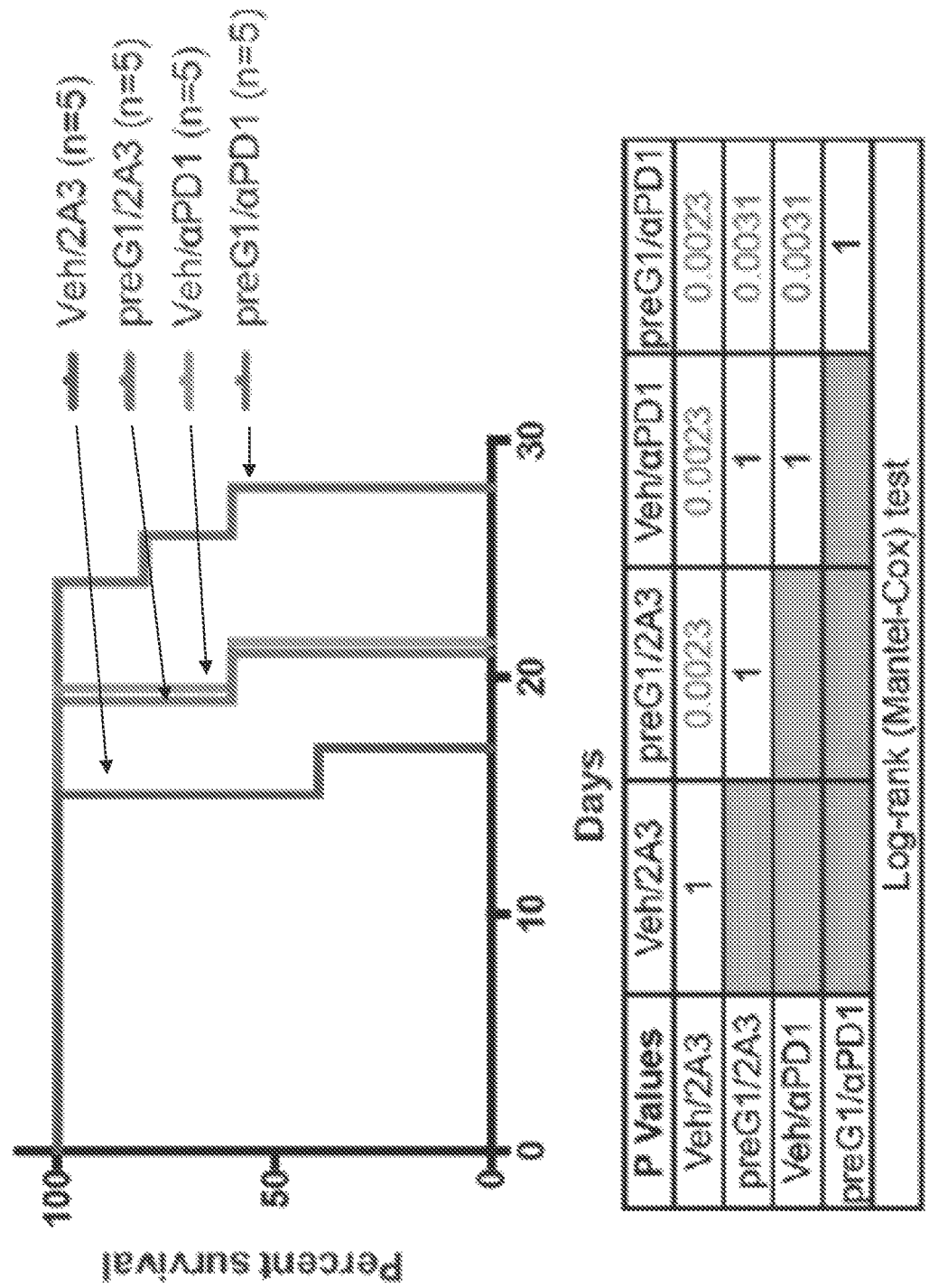
Figure 13G:
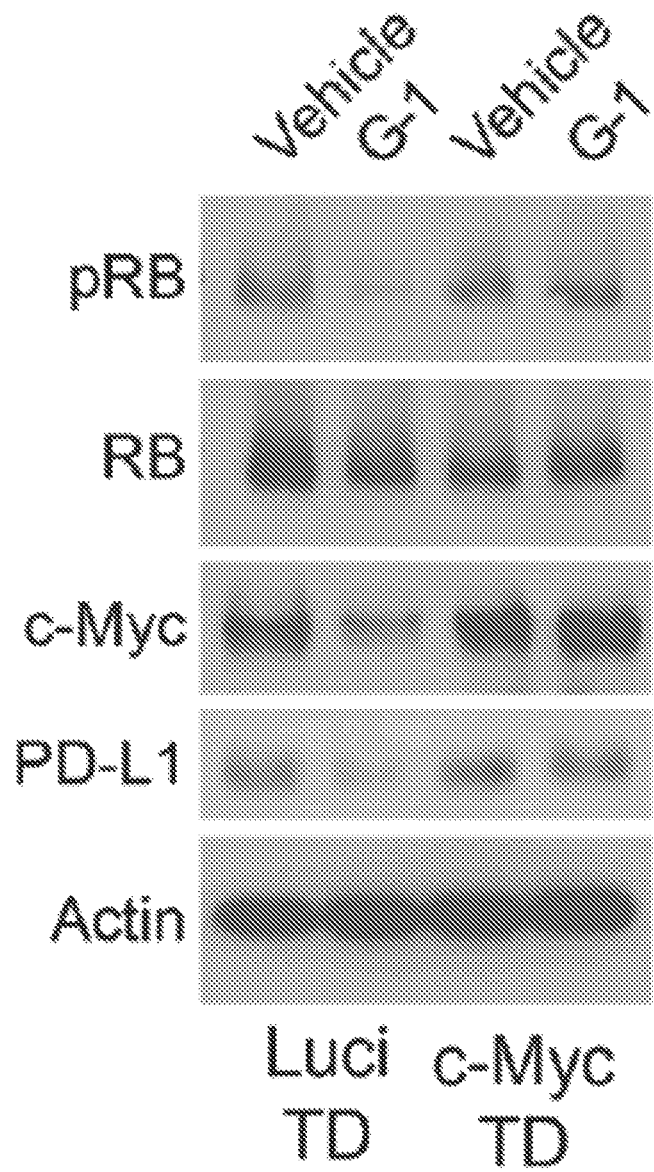

Beyond its role in proliferation and differentiation, c-Myc positively regulates expression of multiple inhibitory immune checkpoint regulators including PDL1. Transient pharmacologic GPER activation in melanoma cells resulted in parallel decreases in both c-Myc and PD-L1 (FIGS. 13A-13C). In cells engineered to maintain c-Myc in the presence of GPER agonist, PD-L1 was preserved (FIG. 13G).

Example 6: Transient GPER Activation Inhibits Proliferation and Augments Response to Immunotherapy As demonstrated herein, GPER signaling induced stable changes in tumor cells that antagonized tumor proliferation and decreased tumor cell expression of immune suppressive proteins. Thus, it was studied whether GPER activation potentiates the antitumor activity of immune checkpoint blockade inhibitors.

To determine whether tumor cell intrinsic GPER signaling influences melanoma vulnerability to immune checkpoint therapy, studies were performed, based on the observation that GPER-driven differentiation is long lasting. G-1 was used to activate GPER and drive differentiation in murine B16F10 melanoma cells in vitro (FIG. 13D). Then, equal numbers of vehicle or G-1-treated tumor cells were injected into syngeneic C57BL/6 mice and the animals were treated with either αPD-1 antibody or isotype antibody control.

G-1 pretreatment alone inhibited subsequent tumor growth and extended survival compared to controls. αPD-1 antibody monotherapy also similarly prolonged survival. However, combination of G-1 pretreatment with αPD-1 antibody dramatically extended survival beyond that seen with either agent alone, indicating that GPER activity in tumor cells induced persistent changes in the tumor sufficient to improve the antitumor activity of systemically administered αPD-1 therapy (FIGS. 13E-13F).

Figure 14A:
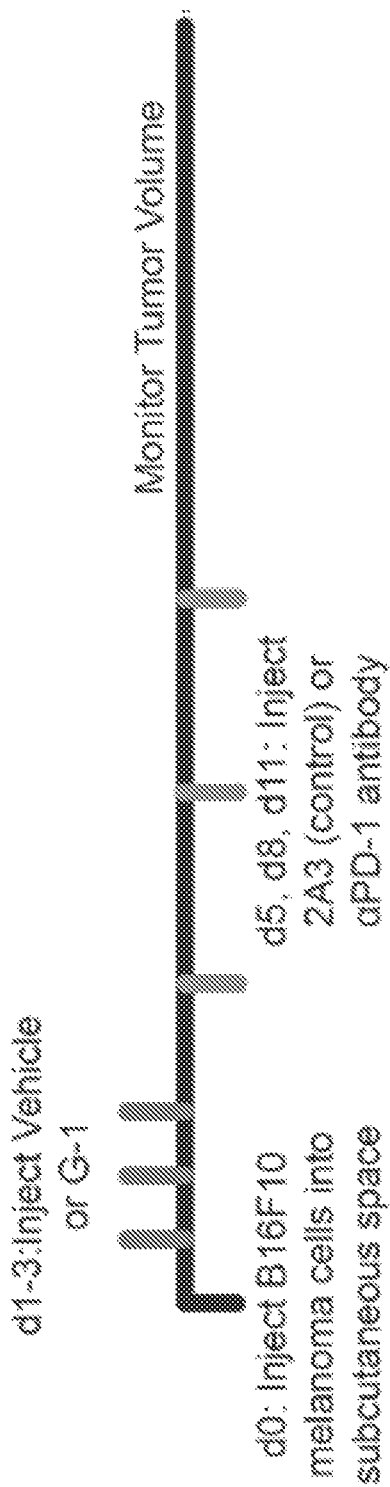
FIGS. 14A-14F illustrate the finding that treatment of melanoma bearing mice with G-1 and αPD-1 immunotherapy dramatically extends survival.

Example 7: Treatment of Melanoma-Bearing Mice with G-1 and αPD-1 Immunotherapy Dramatically Extends Survival To determine whether G-1 has therapeutic utility as a systemically delivered agent with or without immune checkpoint inhibitors, B16F10 melanoma-bearing syngeneic mice were treated with subcutaneous G-1, αPD-1 antibody, or both, and survival compared to matched mice treated with vehicle and isotype antibody controls (in particular, non-specific isotype control antibody 2A3) (FIG. 14A). Total tumor volume was assessed after 5-50 days.

Figure 14B:
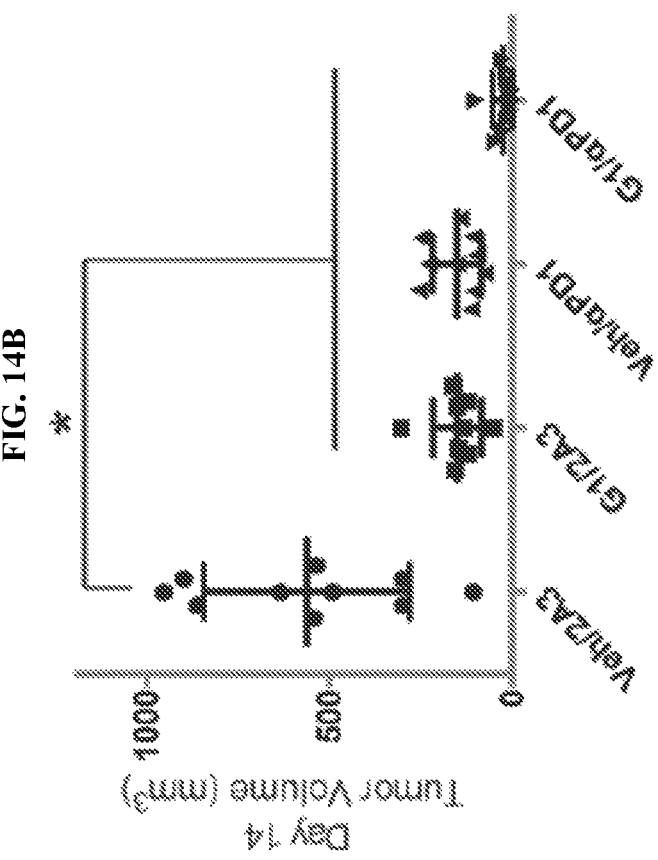
Figure 14C:
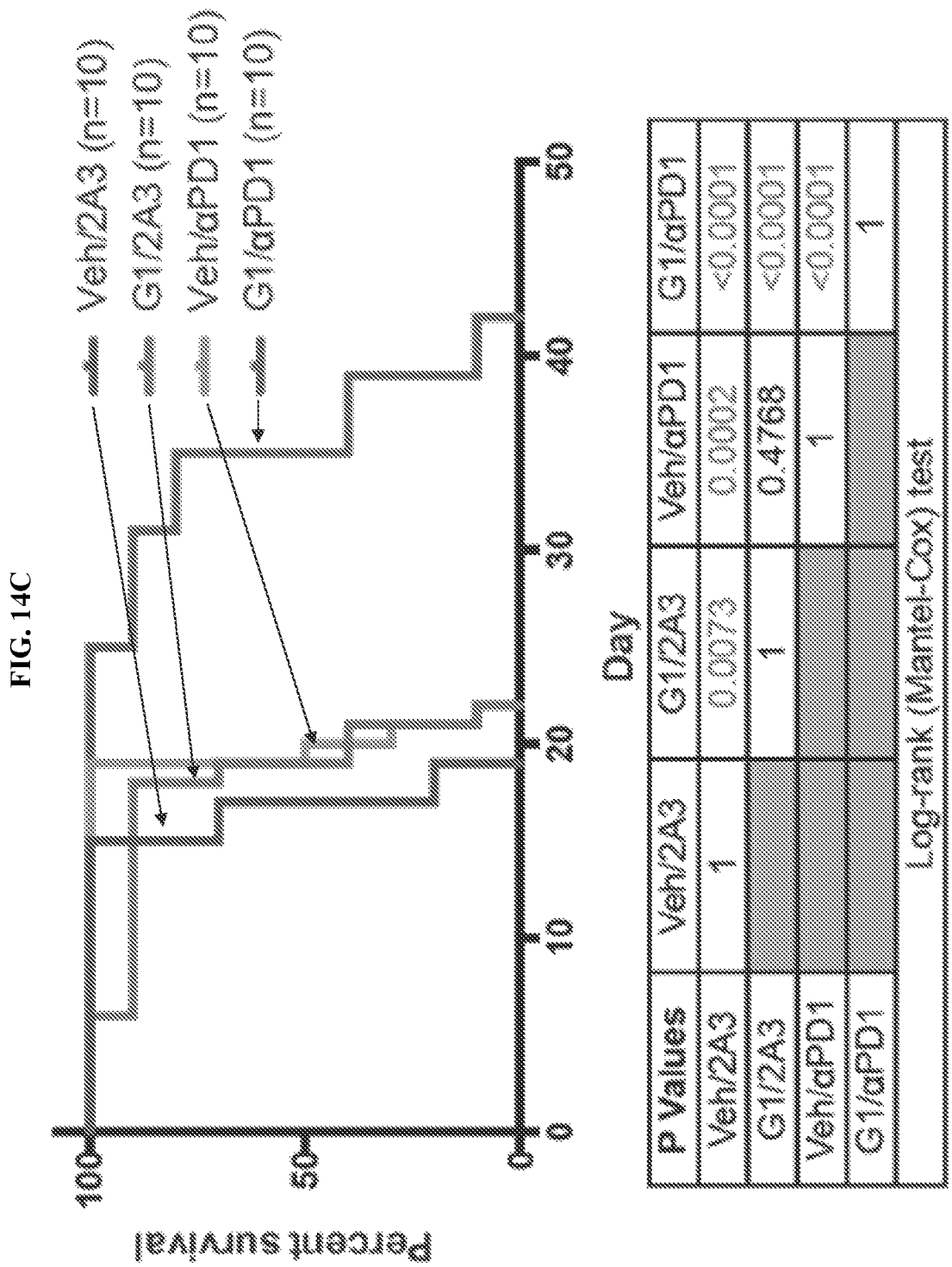

G-1 was well tolerated in mice, and monotherapy extended survival to the same extent as αPD-1. Each monotherapy and combined treatment with αPD-1 and G-1 slowed tumor growth (FIG. 14B). Strikingly, the combined treatment with αPD-1 and G-1 extended survival 7 times longer than with either agent alone, indicating a marked synergistic benefit (FIG. 14C).

Figure 14D:
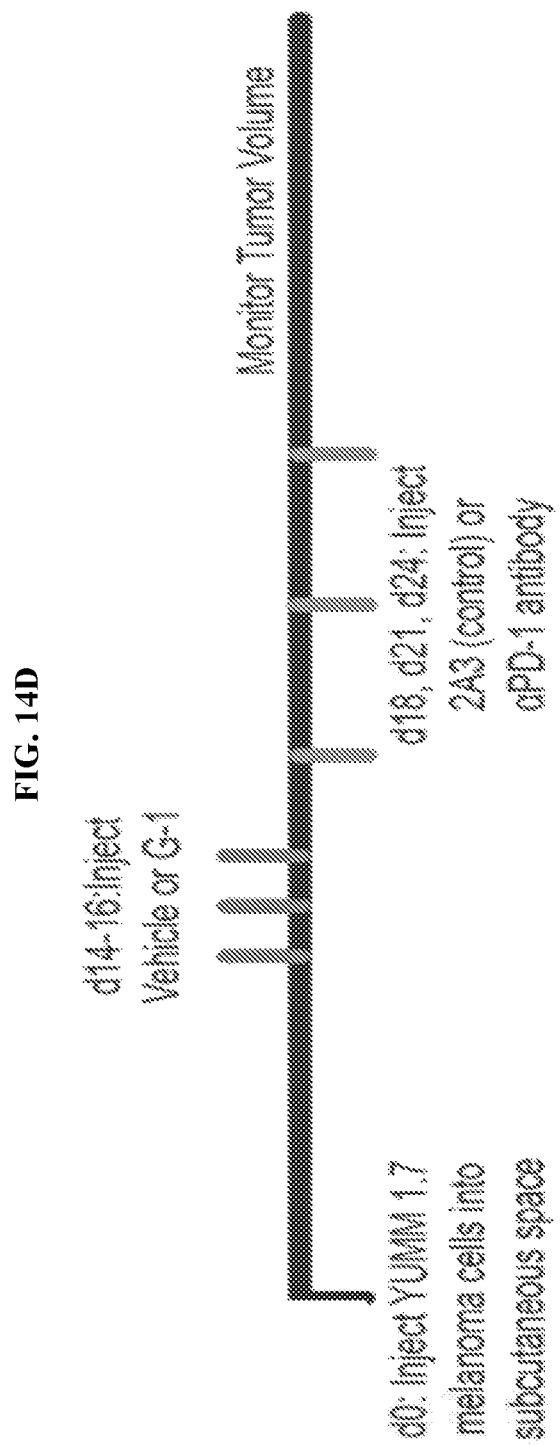

Although B16F10 melanoma is the most commonly used model for melanoma immunology studies, and experimental results have largely translated to humans, B16F10 lacks the BRaf or NRas oncodriver mutations present in most human melanomas. To test whether GPER signaling has similar antimelanoma activity in a potentially more medically relevant model, genetically-defined melanoma cells from the Yale University Mouse Melanoma collection (YUMM) were used. This resource contains melanoma lines generated from established genetically engineered mouse models that were backcrossed onto C57BL/6 backgrounds specifically to facilitate immunology studies. YUMM 1.7 cells (BRafV600E/wt Pten−/−Cdkn2−/−) were injected into C57BL/6 mice and G-1 treatment was initiated with and without αPD-1 after tumors reached 3 to 4 mm in diameter (day 14) (FIG. 14D).

Figure 14E:
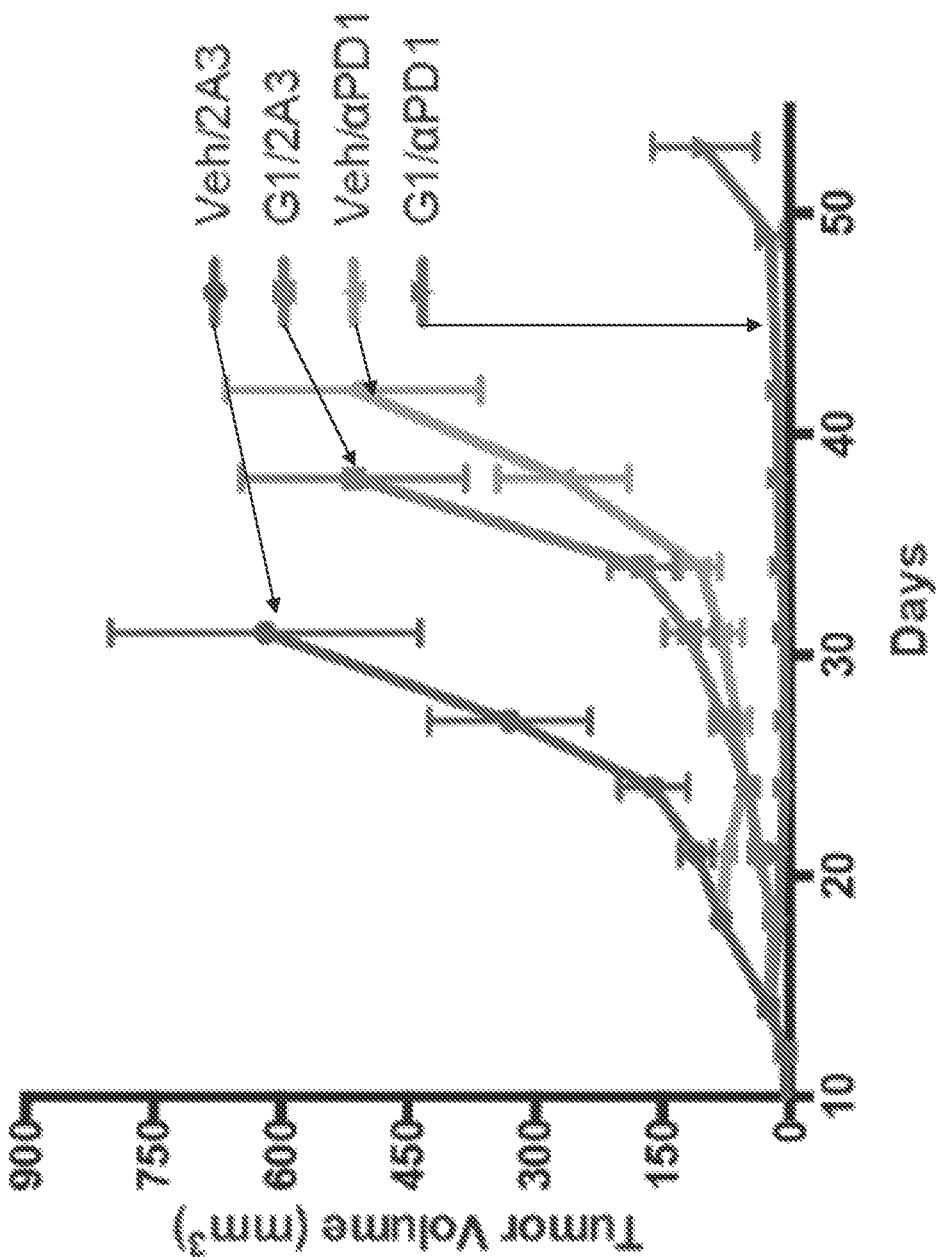
Figure 14F:
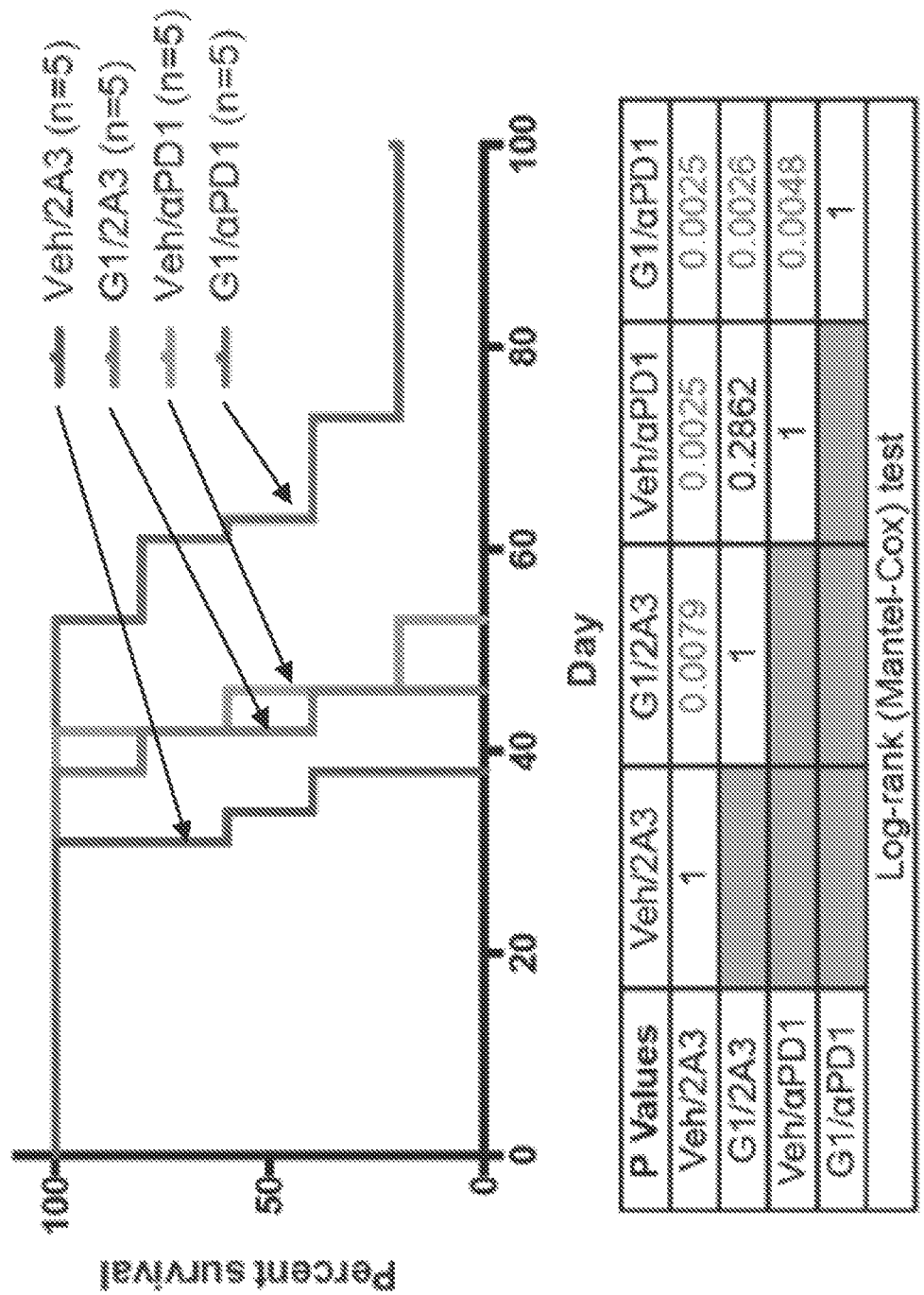

Similar to the results observed with B16F10 melanoma, G-1 or αPD-1 monotherapy resulted in modest, but significant, survival increases, while combination treatment dramatically extended survival further, including long-term survivors (FIGS. 14E-14F).

Example 8: G-1 Treatment In Vivo Alters Tumor Infiltrating Immune Cells

Figure 15A:
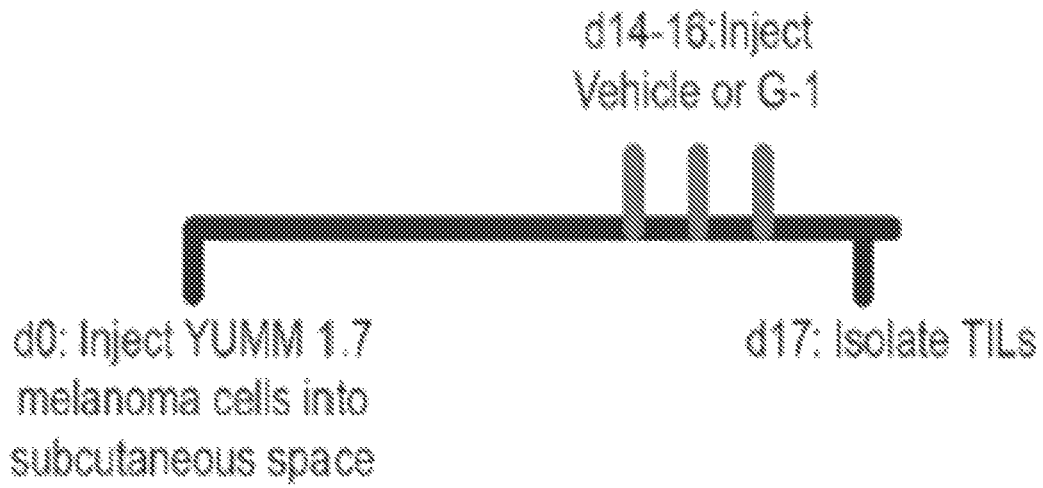
FIGS. 15A-15C illustrate the finding that G-1 treatment in vivo alters tumor infiltrating immune cells.
Figure 15B:
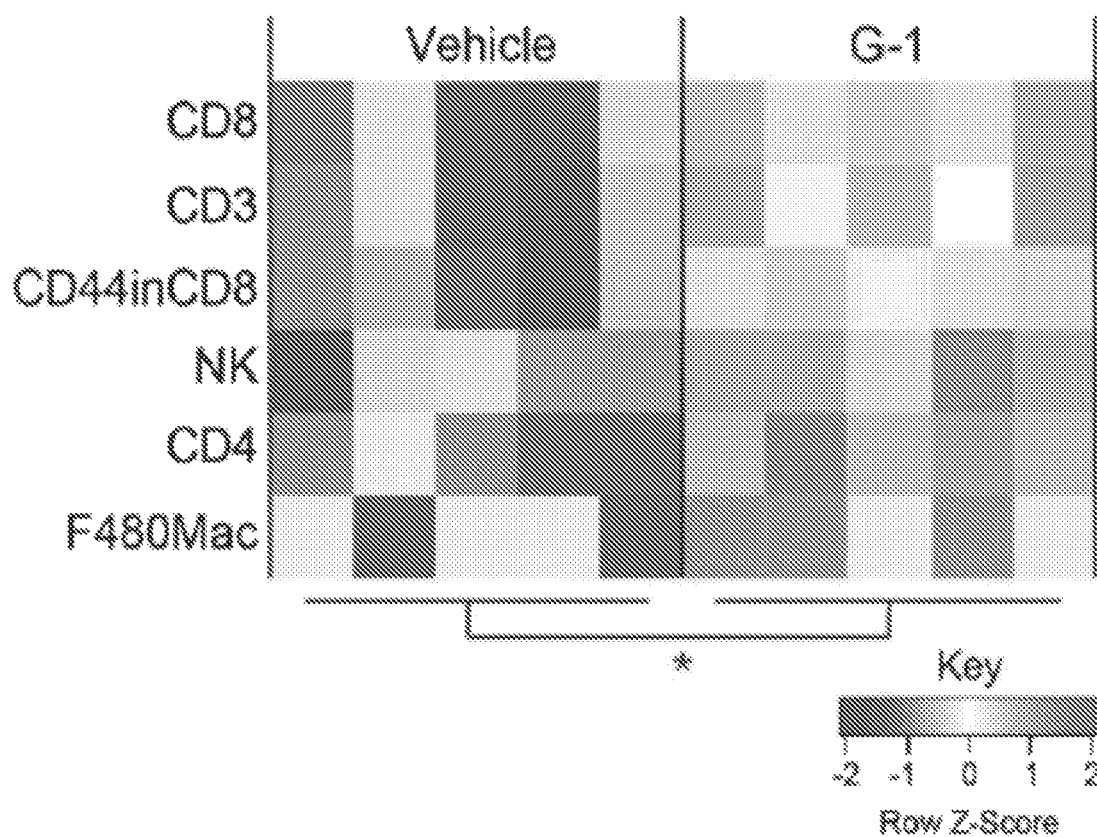
Figure 15C:
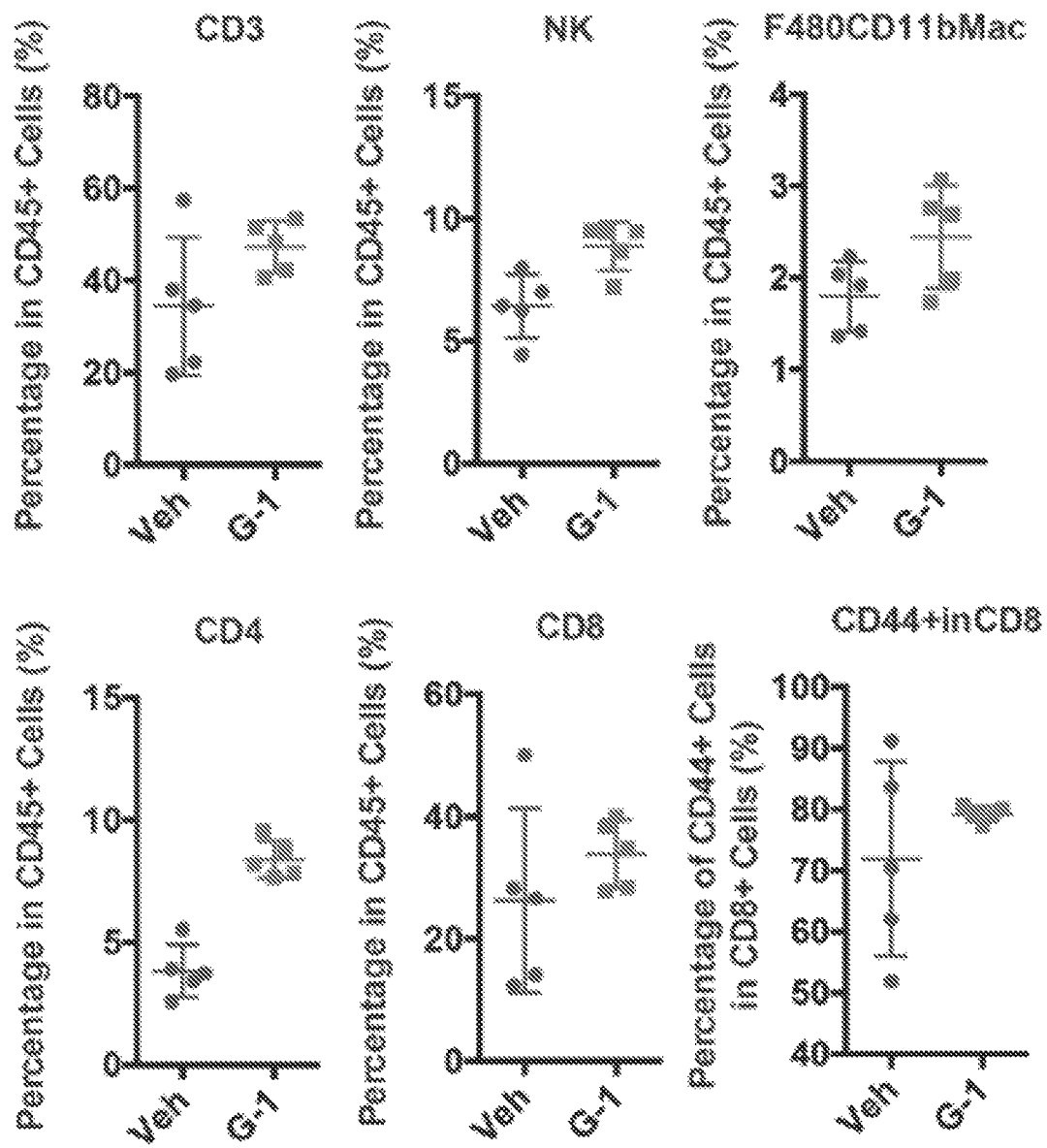

The present results indicate that GPER antitumor activity is independent of tumor oncodrivers. Consistent with the hypothesis that GPER activation changes the nature of immune infiltration, G-1 treatment in melanoma-bearing mice increased several immune cell subsets, including T cells and NK cells, suggesting a more robust inflammatory response (FIGS. 15A-15C).

Figure 16A:
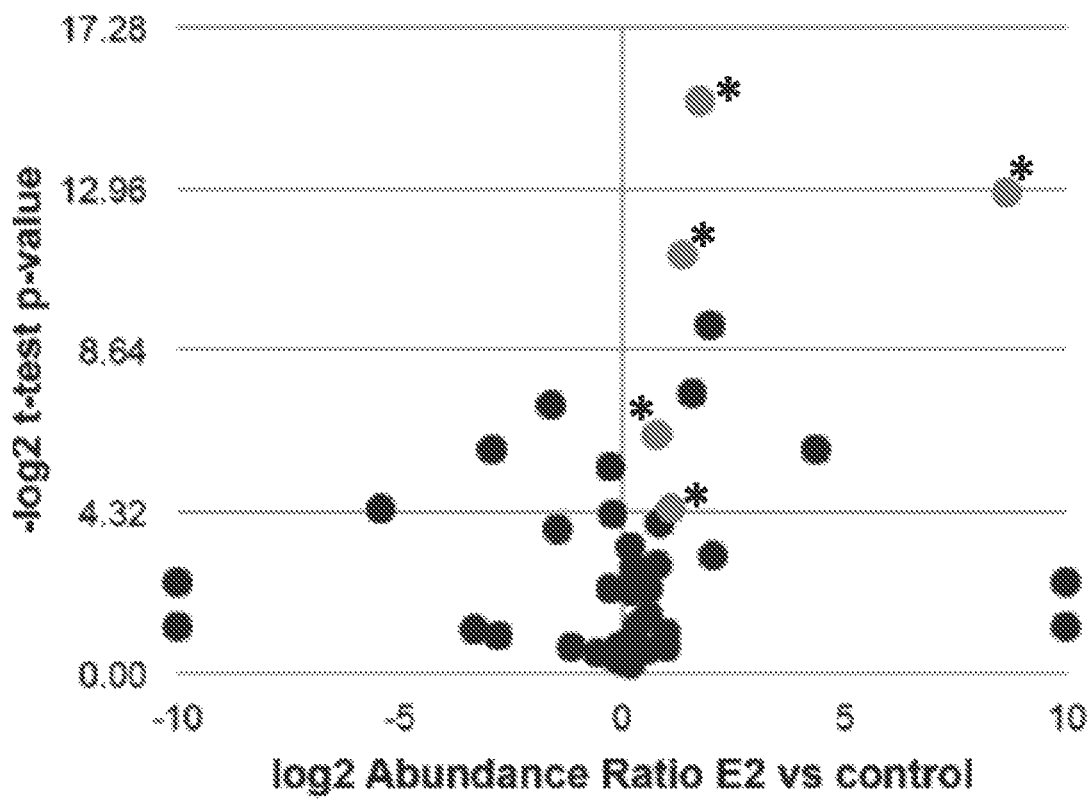
FIGS. 16A-16C illustrate the finding that G-1 treatment drives histone acetylation and synergizes with HDAC inhibitors in melanoma.

Example 9: G-1 Treatment Drives Histone Acetylation and Synergizes with HDAC Inhibitors in Melanoma To begin to identify the epigenetic changes likely underlying stable melanocyte differentiation after GPER activation, mass spectrometry was used to obtain a global analysis of histone posttranslational modifications in estrogen-treated MC. Consistent with a mechanism involving CREB activity, significant increases (in 3 independent biologic replicates) were observed in many histone acetylation marks regulated by the CREB binding partners CBP/P300, including H3K122, H3K23, and H3K18 (FIG. 16A).

In contrast, the H3K9ac mark, which is not written by CBP/P300, was decreased following estrogen treatment. As histone posttranslational modifications, including acetylation, mediate heritable transcriptional memory in other contexts, in certain non-limiting embodiments CBP/P300-regulated histone modifications are responsible for maintaining the heightened differentiated melanocyte state across cell divisions. There are higher levels of CBP-written histone acetyl marks in benign human nevi, and nontumorigenic melanoma cells, compared to melanoma tissues and tumorigenic melanoma cell lines. Together, this indicates that histone acetylations can maintain the differentiated, antiproliferative, nontumorigenic state of GPER-stimulated melanoma cells.

Figure 16B:
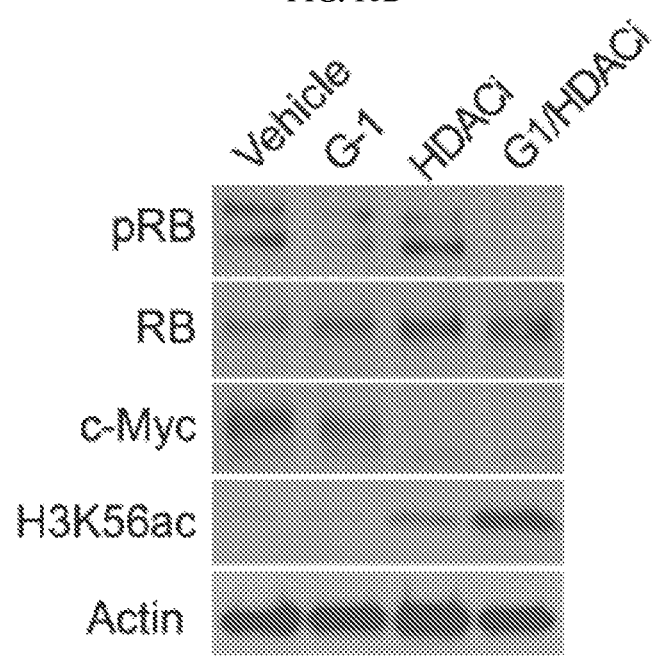
Figure 16C:
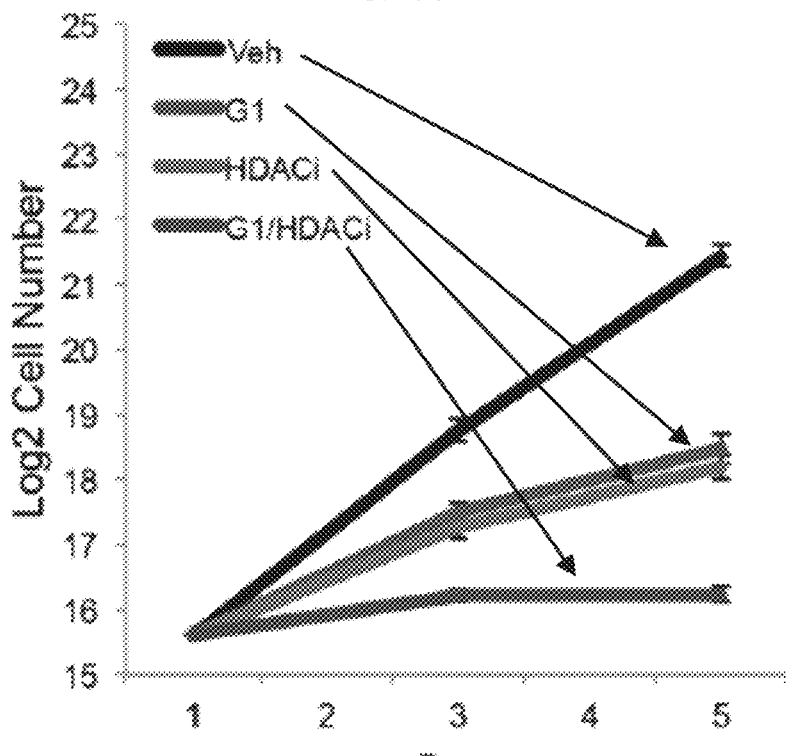

Histone acetyl marks are removed by several histone deacetylases (HDACs), which are aberrantly regulated in many cancers. Although HDAC inhibitors are approved as anticancer agents for cutaneous lymphoma, myeloma, and pancreatic cancer, their utility in melanoma is unclear. In human trials, HDAC inhibitors (HDACi) generally displayed only modest antimelanoma activity as monotherapy agents. HDAC efficacy may have been limited by the fact that trials were conducted without a differentiation driver to promote formation of acetylation marks on histones or other critical oncoproteins (such as c-Myc) that would then be stabilized by the HDACi. Without wishing to be limited by any theory, the anticancer effects of HDAC inhibitors can be potentiated by combination drug regimens that also promote histone acetylation at functionally critical sites. HDACi and GPER agonists independently promote melanoma cell differentiation, and also cooperate to potentiate the activity of each other (FIGS. 16B-16C).

Example 10: GPER Signaling Reduces PDAC Cell Proliferation In Vitro and In Vivo

Figure 17A:
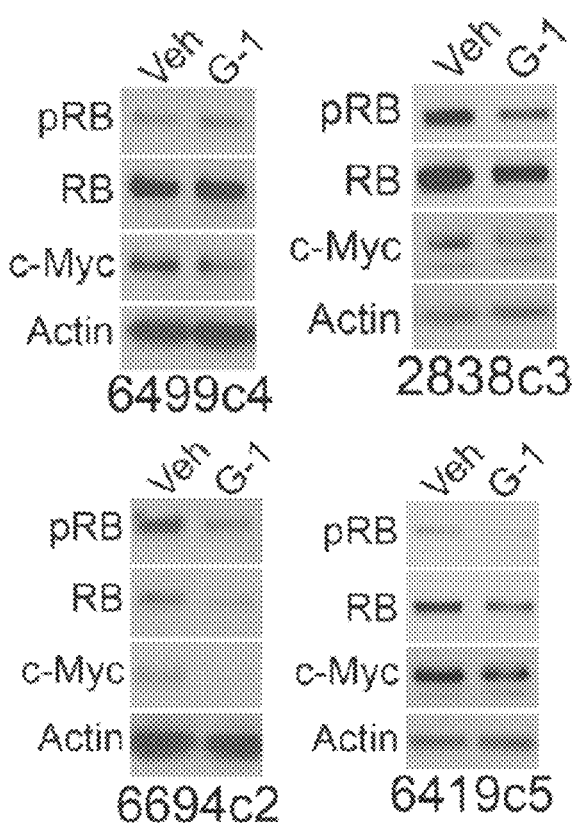
FIGS. 17A-17D illustrate the finding that GPER signaling reduces pancreatic ductal adenocarcinoma (PDAC) cell proliferation in vitro and in vivo.

Pancreatic cancer is less common in women than men, and also less common in users of estrogen-only hormone therapies, suggesting that GPER can have a tumor-suppressive role in pancreatic cancer as well. Using a newly available set of syngeneic pancreatic ductal adenocarcinoma (PDAC) cell lines, the effects of GPER activation on the levels of c-Myc protein were examined. After exposure to G-1, c-Myc and pRB was reduced in these cell lines, consistent with the changes observed in melanoma cell lines (FIG. 17A).

Figure 17B:
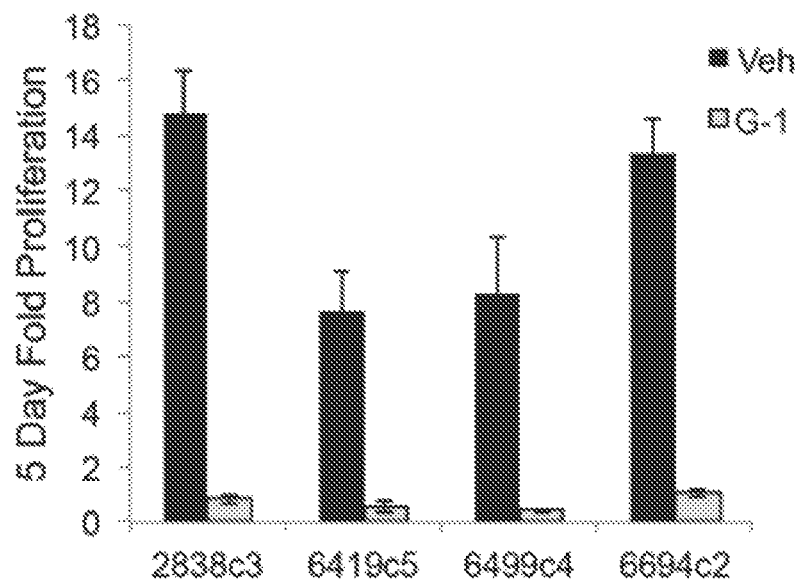

In addition to the levels of these signaling molecules changing, proliferation rates of these cell lines were also inhibited by GPER activation through G-1 (FIG. 17B).

Figure 17C:
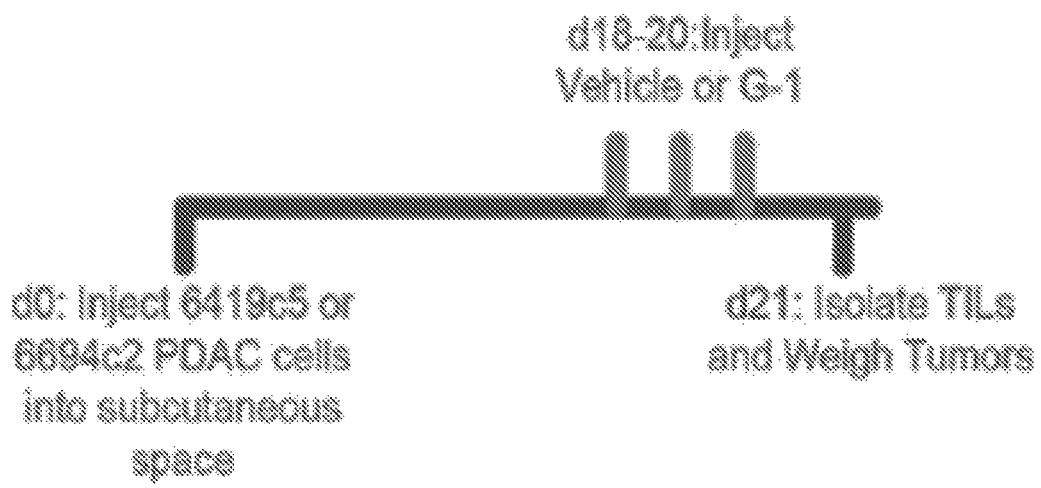

To demonstrate that systemic G-1 administration altered tumor growth in vivo, PDAC tumors were grown in mice for 18 days, then given the standard G-1 dose on 3 consecutive days (FIG. 17C).

Figure 17D:
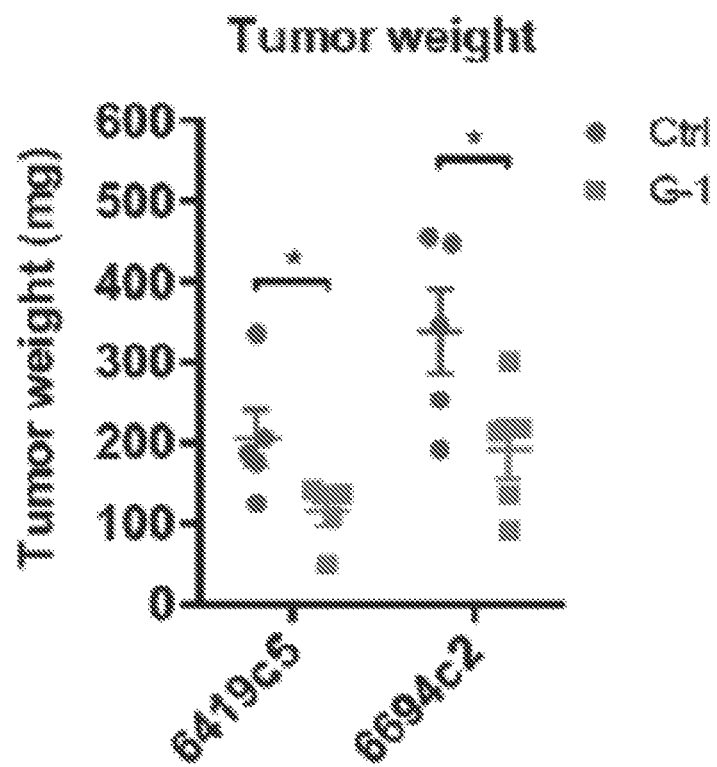

Even with a short follow-up time of 4 days after treatment, tumors were significantly smaller in 2 independent PDAC cell lines, suggesting that GPER activation can have potent antitumor effects in PDAC (FIG. 17D).

Figure 18A:
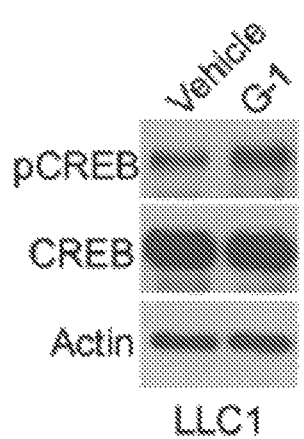
FIGS. 18A-18G illustrate the finding that GPER signaling reduces NSCLC cell proliferation in vitro and in vivo and has combinatorial effects with αPD-1 immunotherapy.

Example 11: GPER Signaling Reduces NSCLC Cell Proliferation In Vitro and In Vivo and has Combinatorial Effects with αPD-1 Immunotherapy Reproductive history influences lung cancer as well. Women have a decreasing risk of lung cancer correlated with the number children they have had. To demonstrate that G-1/GPER signaling has activity in the NSCLC line LLC1, this line was treated with G-1 and elevated pCREB levels were observed after 30 minutes (FIG. 18A).

Figure 18B:
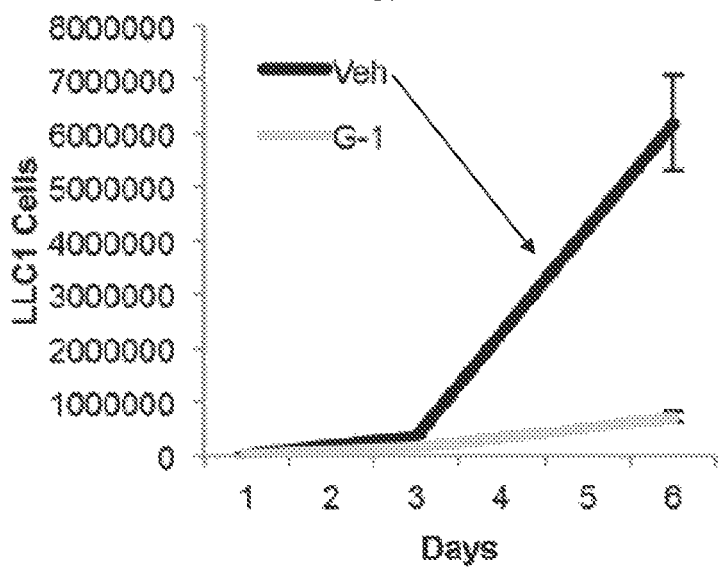
Figure 18C:
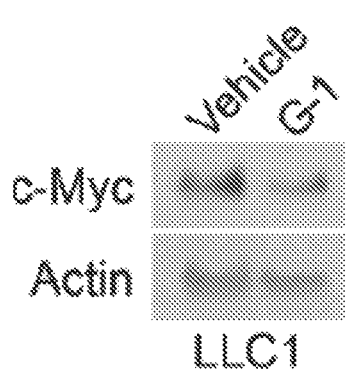

Long-term treatment of LLC1 with G-1 resulted in decreased proliferation (FIG. 18B) and reduction of c-Myc protein (FIG. 18C).

Figure 18D:
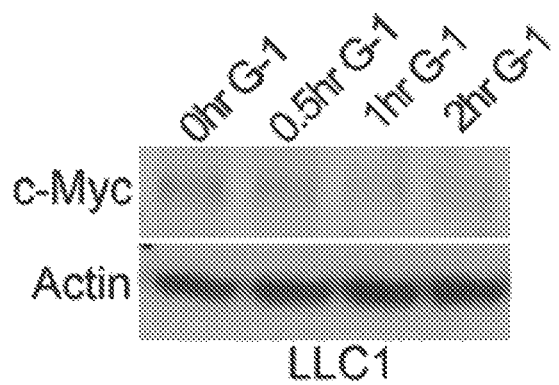
Figure 18E:
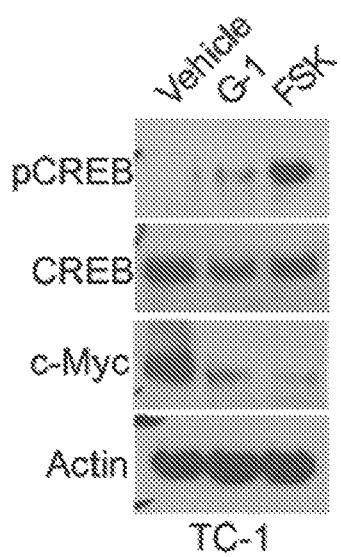

The depletion of c-Myc occurred rapidly (FIG. 18D), and the same signaling effects also occur in an additional NSCLC line TC-1 (FIG. 18E).

Figure 18F:
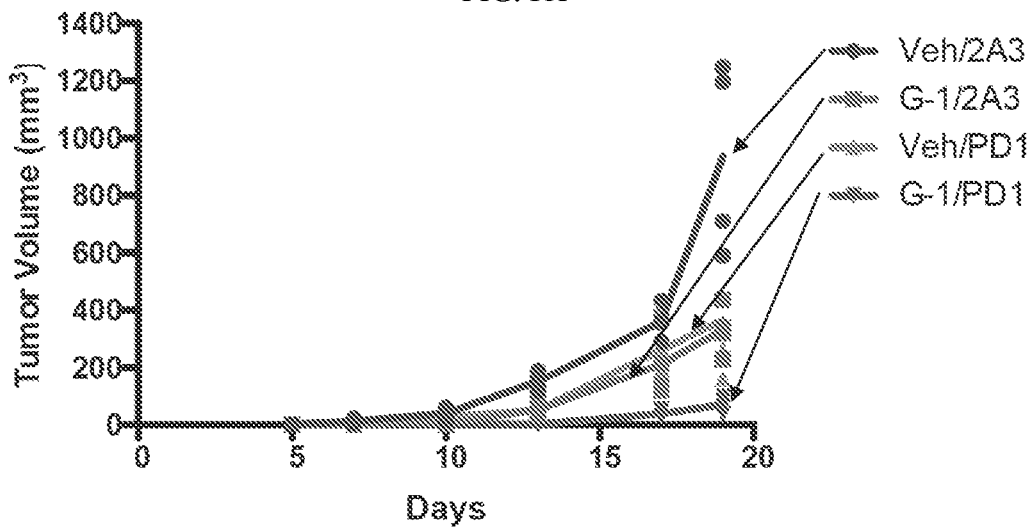
Figure 18G:
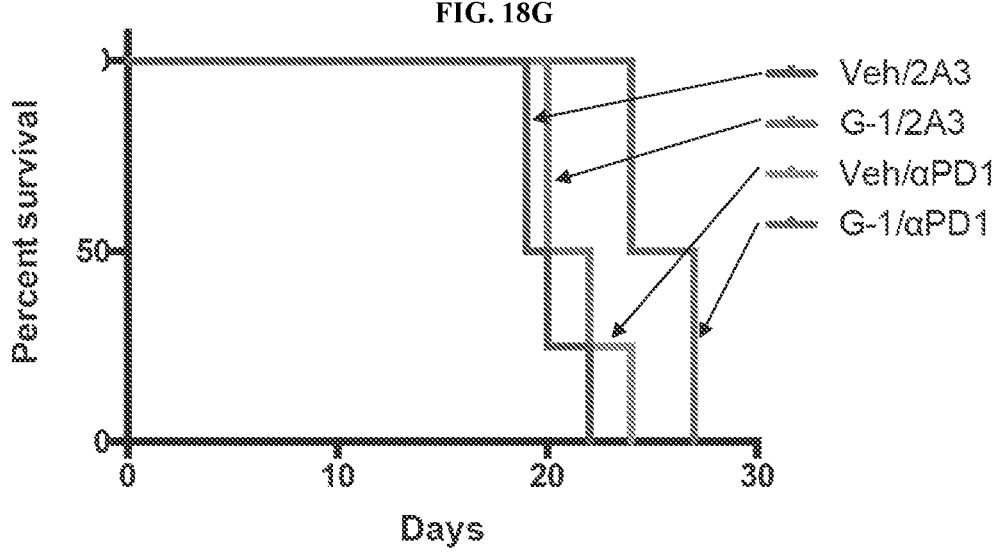

To test whether G-1 had activity in vivo and synergizes with PD-1 immunotherapy, LLC1 tumors were grown in mice that were treated with subcutaneous G-1, αPD-1 antibody, or both, and survival compared to matched mice treated with vehicle and isotype antibody controls. Monotherapy with either G-1 or αPD-1 slowed tumor growth initially (FIG. 18F), but ultimately did not alter survival significantly (FIG. 18G). Combination therapy with G-1 and αPD-1 slowed tumor growth further (FIG. 18F) and also significantly extended survival (FIG. 18G).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating or ameliorating a cancer that expresses the non-canonical steroid hormone receptor, G-protein coupled estrogen receptor (GPER) in a subject, the method comprising:
    administering to the subject in need thereof a therapeutically effective amount of a GPER-specific agonist, and
    further administering to the subject in need thereof a PD-1 checkpoint inhibitor.

2. The method of claim 1, wherein the GPER-specific agonist is G-1 (rel-1-[4-(6-bromo-1,3-benzodioxol-5-yl)-3 aR,4 S, 5,9b S-tetrahydro-3H-cyclopenta[c]quinolin-8-yl]-ethanone), or a salt, solvate, tautomer, enantiomer, or diastereomer thereof.

3. The method of claim 1, wherein the cancer is at least one selected from the group consisting of melanoma, pancreatic cancer, and lung cancer.

4. The method of claim 1, wherein the cancer is at least one selected from the group consisting of melanoma, ocular melanoma, oral melanoma, intestinal melanoma, and pancreatic cancer.

5. The method of claim 1, wherein the subject is further administered at least one additional anticancer treatment.

6. The method of claim 5, wherein the at least one additional anticancer treatment comprises chemotherapy, an engineered chimeric antigen receptor (CAR) T-cell, or radiation therapy.

7. The method of claim 1, wherein the GPER-specific agonist is administered to the subject over a period of 3 weeks or less.

8. A method of treating or ameliorating a GPER-expressing cancer in a subject, the method comprising:
    administering to the subject in need thereof a therapeutically effective amount of the compound G-1 (rel-1-[4-(6-bromo-1,3-benzodioxol-5-yl)-3aR,4S,5,9bS-tetrahydro-3H-cyclopenta[c]quinolin-8-yl]-ethanone), or a salt, solvate, tautomer, enantiomer, or diastereomer thereof; and
    further administering to the subject in need thereof a PD-1 checkpoint inhibitor.

9. The method of claim 8, wherein the cancer is at least one selected from the group consisting of melanoma, pancreatic cancer, and lung cancer.

10. The method of claim 8, wherein the cancer is at least one selected from the group consisting of melanoma, ocular melanoma, oral melanoma, intestinal melanoma, and pancreatic cancer.

11. The method of claim 1, wherein the GPER-specific agonist is formulated in a pharmaceutical composition further comprising at least one pharmaceutically acceptable carrier.

12. The method of claim 8, wherein the compound, or salt, solvate, tautomer, enantiomer, or diastereomer thereof, is formulated in a pharmaceutical composition further comprising at least one pharmaceutically acceptable carrier.

13. The method of claim 1, wherein the administering is by at least one administration route selected from the group consisting of inhalational, oral, rectal, vaginal, parenteral, topical, transdermal, pulmonary, intranasal, buccal, ophthalmic, intrathecal, intracranial, and intravenous.

14. The method of claim 8, wherein the administering is by at least one administration route selected from the group consisting of inhalational, oral, rectal, vaginal, parenteral, topical, transdermal, pulmonary, intranasal, buccal, ophthalmic, intrathecal, intracranial, and intravenous.

15. The method of claim 1, wherein the GPER-specific agonist and the PD-1 checkpoint inhibitor are co-formulated.

16. The method of claim 8, wherein the compound, or salt, solvate, tautomer, enantiomer, or diastereomer thereof, and the PD-1 checkpoint inhibitor are co-formulated.

17. The method of claim 1, wherein the cancer is at least one selected from the group consisting of melanoma, ocular melanoma, oral melanoma, intestinal melanoma, Burkitt lymphoma, leukemia, sarcoma, lymphoma, multiple myeloma, brain cancer, neuroblastoma, medulloblastoma, astrocytoma, glioblastoma, ovarian cancer, cervix cancer, uterine cancer, colorectal cancer, breast cancer, pancreatic cancer, lung cancer, stomach cancer, thyroid cancer, liver cancer, prostate cancer, esophagus cancer, kidney cancer, bladder cancer, and gall bladder cancer.

18. The method of claim 8, wherein the cancer is at least one selected from the group consisting of melanoma, ocular melanoma, oral melanoma, intestinal melanoma, Burkitt lymphoma, leukemia, sarcoma, lymphoma, multiple myeloma, brain cancer, neuroblastoma, medulloblastoma, astrocytoma, glioblastoma, ovarian cancer, cervix cancer, uterine cancer, colorectal cancer, breast cancer, pancreatic cancer, lung cancer, stomach cancer, thyroid cancer, liver cancer, prostate cancer, esophagus cancer, kidney cancer, bladder cancer, and gall bladder cancer.

* * * * *